(12) United States Patent
Genolet

(10) Patent No.: US 11,319,590 B2
(45) Date of Patent: May 3, 2022

(54) ENHANCED IMMUNE CELL RECEPTOR SEQUENCING METHODS

(71) Applicant: Ludwig Institute for Cancer Research Ltd., New York, NY (US)

(72) Inventor: Raphael Genolet, Epalinges (CH)

(73) Assignee: Ludwig Institute for Cancer Research Ltd., New York, NY (US)

( * ) Notice: Subject to any disclaimer, the term of this patent is extended or adjusted under 35 U.S.C. 154(b) by 197 days.

(21) Appl. No.: 16/481,936

(22) PCT Filed: Jan. 30, 2018

(86) PCT No.: PCT/US2018/015819
§ 371 (c)(1),
(2) Date: Jul. 30, 2019

(87) PCT Pub. No.: WO2018/144410
PCT Pub. Date: Aug. 9, 2018

(65) Prior Publication Data
US 2020/0002766 A1    Jan. 2, 2020

Related U.S. Application Data

(60) Provisional application No. 62/452,409, filed on Jan. 31, 2017.

(51) Int. Cl.
*C12P 19/34*    (2006.01)
*C12Q 1/6881*    (2018.01)
*C12Q 1/6874*    (2018.01)

(52) U.S. Cl.
CPC ......... *C12Q 1/6881* (2013.01); *C12Q 1/6874* (2013.01)

(58) Field of Classification Search
CPC ............................. C12Q 1/6881; C12Q 1/6869
See application file for complete search history.

(56) References Cited

U.S. PATENT DOCUMENTS

2014/0322716 A1* 10/2014 Robins ................ C12Q 1/6846
                                                          435/6.12
2014/0349858 A1* 11/2014 Motley ................... C12Q 1/70
                                                              506/2

(Continued)

FOREIGN PATENT DOCUMENTS

WO    WO 2013/128204 A1    9/2013
WO    WO 2013/188831 A1    12/2013
WO    WO 2014/144713 A2    9/2014

OTHER PUBLICATIONS

Boyd et al., Measurement and clinical monitoring of human lymphocyte clonality by massively parallel VDJ pyrosequencing. Sci Transl Med. Dec. 23, 2009;1(12):12ra23. doi: 10.1126/scitranslmed.3000540.

(Continued)

*Primary Examiner* — Kenneth R Horlick
(74) *Attorney, Agent, or Firm* — Wolf, Greenfield & Sacks, P.C.

(57) ABSTRACT

Disclosed are methods for sequencing immune cell receptor repertoires from immune cell populations, the methods comprising isolating RNA from immune cells, generating cDNA from the RNA, ligating adapter sequences to the cDNA, and sequencing the cDNA. Also provided are kits containing primer mixtures for the sequencing of immune cell receptor repertoires.

16 Claims, 12 Drawing Sheets

Specification includes a Sequence Listing.

(56) References Cited

U.S. PATENT DOCUMENTS

| | | | |
|---|---|---|---|
| 2015/0307874 A1 | 10/2015 | Jaitin et al. | |
| 2016/0040234 A1* | 2/2016 | Hutchins | C12Q 1/6874 506/2 |
| 2019/0194653 A1* | 6/2019 | Amit | C12N 15/1093 |

OTHER PUBLICATIONS

Linnemann et al., High-throughput identification of antigen-specific TCRs by TCR gene capture. Nat Med. Nov. 2013;19(11):1534-41. doi: 10.1038/nm.3359. Epub Oct. 13, 2013.

Mariani et al., Comprehensive assessment of the TCRBV repertoire in small T-cell samples by means of an improved and convenient multiplex PCR method. Exp Hematol. Jun. 2009; 37(6):728-38. doi: 10.1016/j.exphem.2009.03.003.

Ozawa et al., Amplification and analysis of cDNA generated from a single cell by 5'-RACE: application to isolation of antibody heavy and light chain variable gene sequences from single B cells. Biotechniques. Apr. 2006;40(4):469-70, 472, 474 passim. doi: 10.2144/000112123.

Genolet et al., Duality of the murine CD8 compartment. Proc Natl Acad Sci U S A. Mar. 18, 2014;111(11):E1007-15.doi: 10.1073/pnas.1317847111. Epub Mar. 4, 2014.

Genolet et al., Highly diverse TCRα chain repertoire of pre-immune CD8? T cells reveals new insights in gene recombination. EMBO J. Apr. 4, 2012;31(7):1666-78. doi: 10.1038/emboj.2012.48. Epub Feb. 28, 2012.

Krangel et al., Mechanics of T cell receptor gene rearrangement. Curr Opin Immunol. Apr. 2009;21(2):133-9. doi: 10.1016/j.coi.2009.03.009. Epub Apr. 9, 2009.

Robins et al., Comprehensive assessment of T-cell receptor beta-chain diversity in alphabeta T cells. Blood. Nov. 5, 2009;114(19):4099-107. doi: 10.1182/blood-2009-04-217604. Epub Aug. 25, 2009.

Rudolph et al., How TCRs bind MHCs, peptides, and coreceptors. Annu Rev Immunol. 2006;24:419-66. doi: 10.1146/annurev.immunol.23.021704.

Starr et al., Positive and negative selection of T cells. Annu Rev Immunol. 2003;21:139-76. doi: 10.1146/annurev.immunol.21.120601.141107.

Turchaninova et al., Pairing of T-cell receptor chains via emulsion PCR. Eur J Immunol. Sep. 2013;43(9):2507-15. doi: 10.1002/eji.201343453. Epub Jun. 26, 2013.

Carlson et al., Using synthetic templates to design an unbiased multiplex PCR assay. Nat Commun. 2013;4:2680. doi: 10.1038/ncomms3680.

Liu et al., Systematic Comparative Evaluation of Methods for Investigating the TCRβ Repertoire. PLoS One. Mar. 28, 2016;11(3):e0152464. doi: 10.1371/journal.pone.0152464.

Polz et al., Bias in template-to-product ratios in multitemplate PCR. Appl Environ Microbiol. Oct. 1998;64(10):3724-30. doi: 10.1128/AEM.64.10.3724-3730.1998.

Rosati et al., Overview of methodologies for T-cell receptor repertoire analysis. BMC Biotechnol. Jul. 10, 2017;17(1):61. doi: 10.1186/s12896-017-0379-9.

Wulf et al., Non-templated addition and template switching by Moloney murine leukemia virus (MMLV)-based reverse transcriptases co-occur and compete with each other. J Biol Chem. Nov. 29, 2019;294(48):18220-18231. doi: 10.1074/jbc.RA119.010676. Epub Oct. 22, 2019.

* cited by examiner

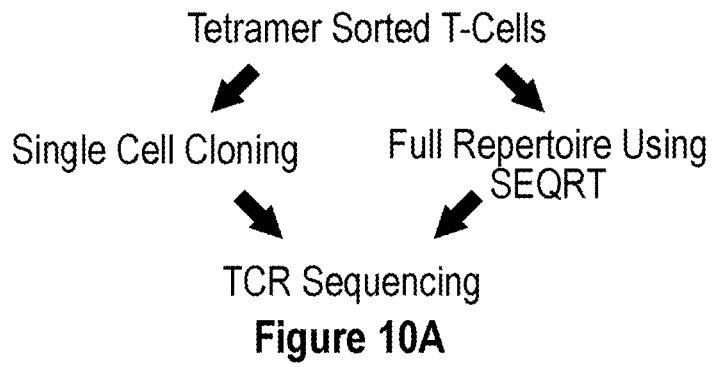

Figure 10A

Clones

| 25 | hTRBV04-1 | hTRBJ01-1 | IN | CASSRHVGGVPEAFFG |
| --- | --- | --- | --- | --- |
| 8 | hTRBV19 | hTRBJ02-7 | IN | CASSIGRGSEQYFG |
| 3 | hTRBV06-4 | hTRBJ01-1 | IN | CASSDVLSGEAFFG |
| 2 | hTRBV04-3 | hTRBJ01-1 | IN | CASQGHKNTEAFFG |
| 2 | hTRBV07-6 | hTRBJ01-4 | IN | CASSLGPGGVKTNEKLFFG |
| 2 | hTRBV07-9 | hTRBJ01-4 | IN | CASSLGPGGVKTNEKLFFG |

Repertoire

| 149038 | hTRBV06-4 | hTRBJ01-1 | IN | CASSDVLSGEAFFG |
| --- | --- | --- | --- | --- |
| 83723 | hTRBV04-3 | hTRBJ01-1 | IN | CASQGHKNTEAFFG |
| 82575 | hTRBV07-6 | hTRBJ01-4 | IN | CASSLGPGGVKTNEKLFFG |
| 35271 | hTRBV19 | hTRBJ02-7 | IN | CASSIGRGSEQYFG |
| 18022 | hTRBV04-1 | hTRBJ01-1 | IN | CASSRHVGGVPEAFFG |
| 2983 | hTRBV19 | hTRBJ01-5 | IN | CASSASKGQPQHFG |
| 974 | hTRBV04-1 | hTRBJ01-1 | IN | CASQGHKNTEAFFG |
| 780 | hTRBV07-9 | hTRBJ01-4 | IN | CASSLGPGGVKTNEKLFFG |

Figure 10C

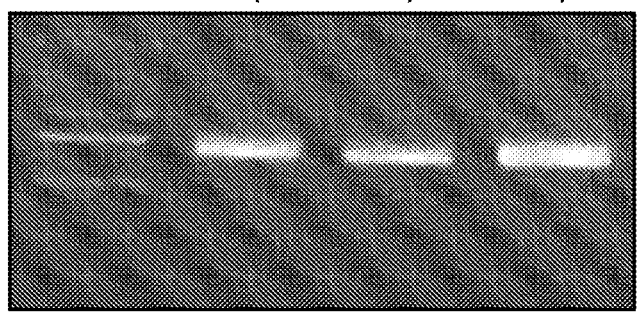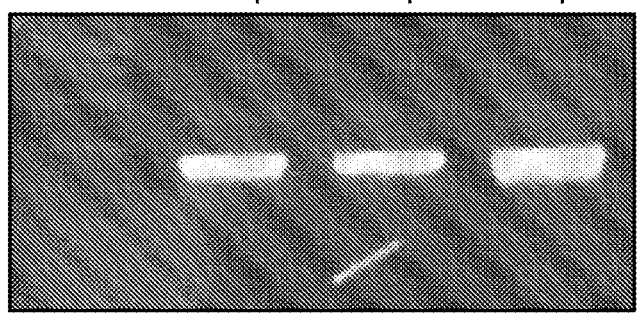
Figure 12

ENHANCED IMMUNE CELL RECEPTOR SEQUENCING METHODS

RELATED APPLICATIONS

This application is a national stage filing under 35 U.S.C. 371 of International Patent Application Serial No. PCT/US2018/015819, filed Jan. 30, 2018, which claims priority under 35 U.S.C. § 119(e) to U.S. provisional patent application Ser. No. 62/452,409, filed Jan. 31, 2017, the entire contents of each of which are incorporated herein by reference.

FIELD

The disclosure relates to methods, systems and kits for sequencing immune cell receptor repertoires from immune cells, such as T-cells or B-cells.

BACKGROUND

Immune cell repertoires, such as B- or T-cell repertoires, consists of millions of lymphocytes, each expressing a different protein complex that enables specific recognition of a single antigen. CD4 and CD8 positive T-cells express so-called T-cell receptors (TCRs). These heterodimeric receptors recognize antigen-derived peptides displayed by major histocompatibility complex (MHC) molecules on the surface of antigen presenting cells, as described in Rudolph M G, Stanfield R L, Wilson I A. How TCRs bind MHCs, peptides, and coreceptors. Annu Rev Immunol. 2006; 24:419-66. TCRs are composed of two subunits, most commonly of one α and one β chain. A less common type of TCR contains one γ and one δ chain.

Alpha (α) chains consists of a (variable) V, a joining (J) and a constant (C) region, while beta (β) chains contain an additional diversity (D) region between the V and the J region (see FIG. 1), as described in Starr T K, Jameson S C, Hogquist K A. Positive and negative selection of T cells. Annu Rev Immunol. 2003; 21:139-76. Each of these TCR regions is encoded in several pieces, so-called gene segments, which are spatially segregated in the germline. In humans, the TCR α gene locus contains 54 different V gene segments, and 61 J gene segments. The human TCR β chain locus comprises 65 V, 2 D and 14 J segments. The great structural diversity of TCRs is achieved by somatic recombination of these TCR gene segments during lymphocyte development in the thymus. During this process, several gene segments of each region type are randomly selected and joined to form a rearranged TCR locus. Additional junctional diversity is created by the addition or removal of nucleotides at the sites of recombination, as described in Krangel M S. Mechanics of T cell receptor gene rearrangement. Curr Opin Immunol. 2009 April; 21(2):133-9. The process of V(D)J joining plays a critical role in shaping the third hypervariable loops (also called complementary determining regions, CDR3s) of the TCR α and β chains. These regions bind antigens and are essential for providing the high specificity of antigen recognition that TCRs exhibit.

Similarly to the TCR αβ, TCR gamma (γ) and delta (δ) segments undergo V(D)J rearrangement during thymus development. Both loci are recombined in the double negative (DN) stage of T-cell development. Differentiation towards γδ or αβ lineage relies on the ability of the cell to produce functional γδ or αβ TCR. The δ locus is embedded within the α locus. Dδ, Jδ and Cδ segments are located in between the V and the J segment of the α locus. The Vδ segments are the same as the Vα segments but only a fraction of the Vα segments are used for the TCR δ chain.

Overall, V(D)J recombination is able to generate millions of different TCR sequences and plays a critical role in an organism's ability to eliminate infections or transformed cells. Not surprisingly, TCR repertoires affect a wide range of diseases, including malignancy, autoimmune disorders and infectious diseases. TCR sequencing has been instrumental for our understanding of how the TCR repertoire evolves during infection or following treatment (e.g. after hematopoietic stem cell transplantation, chronical viral infection, immunotherapy). Further, the identification of TCRs on tumor-infiltrating lymphocytes and other T-cells that target cancer-specific epitopes has not only furthered our knowledge of malignant disease, but has also led to novel therapies for cancer such as adoptive T-cell transfer or cancer vaccines.

Due to the large diversity of sequences, determining TCR repertoires has been challenging in praxis. In the last couple of years, next generation sequencing (NGS) has opened up new opportunities to comprehensively assess the extreme diversity of TCR repertoires, as described in Genolet R, Stevenson B J, Farinelli L, Osterås M, Luescher I F. Highly diverse TCRα chain repertoire of pre-immune CD8[+] T cells reveals new insights in gene recombination. EMBO J. 2012 Apr. 4; 31(7):1666-78; Robins H S, Campregher P V, Srivastava S K, Wacher A, Turtle C J, Kahsai O, Riddell S R, Warren E H, Carlson C S. Comprehensive assessment of T-cell receptor beta-chain diversity in alpha beta T cells. Blood. 2009 Nov. 5; 114(19):4099-107; Linnemann C, Heemskerk B, Kvistborg P, Kluin R J, Bolotin D A, Chen X, Bresser K, Nieuwland M, Schotte R, Michels S, Gomez-Eerland R, Jahn L, Hombrink P, Legrand N, Shu C J, Mamedov I Z, Velds A, Blank C U, Haanen J B, Turchaninova M A, Kerkhoven R M, Spits H, Hadrup S R, Heemskerk M H, Blankenstein T, Chudakov D M, Bendle G M, Schumacher T N. High-throughput identification of antigen-specific TCRs by TCR gene capture. Nat Med. 2013 November; 19(11):1534-41; Turchaninova M A, Britanova O V, Bolotin D A, Shugay M, Putintseva E V, Staroverov D B, Sharonov G, Shcherbo D, Zvyagin I V, Mamedov I Z, Linnemann C, Schumacher T N, Chudakov D M. Pairing of T-cell receptor chains via emulsion PCR. Eur J Immunol. 2013 September; 43(9):2507-15.

Since most current TCR sequencing techniques require enrichment of TCR genes for sequencing, the majority of methods include an amplification step, in which the nucleic acids encoding the individual TCRs are amplified. Therefore, one of the challenges of the TCR sequencing relates to the ability of the technology to maintain the proportion of each TCR during the amplification. Thus, the ways in which TCR libraries are prepared have a strong impact on the quality and the reliability of the obtained sequencing results and on the conclusions than can be drawn from the data. Several approaches have been used to amplify and sequence TCR repertoires in the past, each method with its own set of issues.

One frequently employed method for TCR sequencing is based on a multiplex PCR step, in which all the primers for the V and the J segments are mixed together to amplify all the possible V(D)J rearrangements/combinations, as described in Robins H S, Campregher P V, Srivastava S K, Wacher A, Turtle C J, Kahsai O, Riddell S R, Warren E H, Carlson C S. Comprehensive assessment of T-cell receptor beta-chain diversity in alpha beta T cells. Blood. 2009 Nov. 5; 114(19):4099-107. The main drawback of this technology is that the amplification is not quantitative: Because the efficiency of each primer pair varies, some TCR sequences are preferentially represented in the library.

Another TCR sequencing method uses a process called "DNA gene capture" to isolate TCR encoding DNA fragments, as described in Linnemann C, Heemskerk B, Kvistborg P, Kluin R J, Bolotin D A, Chen X, Bresser K, Nieuwland M, Schotte R, Michels S, Gomez-Eerland R, Jahn L, Hombrink P, Legrand N, Shu C J, Mamedov I Z, Velds A, Blank C U, Haanen J B, Turchaninova M A, Kerkhoven R M, Spits H, Hadrup S R, Heemskerk M H, Blankenstein T, Chudakov D M, Bendle G M, Schumacher T N. High-throughput identification of antigen-specific TCRs by TCR gene capture. Nat Med. 2013 November; 19(11):1534-41. However, since this method uses DNA rather than RNA, this method will also isolate V and J segments that have not yet undergone somatic rearrangement. As a consequence, many of the obtained sequencing data are uninformative for TCR gene identification as they do not contain the V(D)J region of rearranged TCR gene locus. Furthermore, using DNA instead of RNA for the TCR gene analysis may overestimate the diversity of the TCR repertoire as only one of the two β chains is expressed by the T-cells while the other gene is silenced (allelic exclusion).

A third method of TCR amplification is based on the 5'-Race PCR technology (SMARTer® Human TCR a/b Profiling Kit, Takara-Clontech). In this method, a nucleic acid adapter is added to the 5'-end of the cDNA during the reverse transcription step. As a result, TCR products can be subsequently amplified with a single primer pair, with one primer binding to the adapter at the 5'-end of the cDNA and the second primer binding to the constant region near the 3'-end of the cDNA. One of the disadvantages of this technique is that the amplification step will generate PCR fragments ranging between 500 and 600 bp. As the length of the V segment exceeds 400 bp it is actually not possible to sequence the V(D)J junction starting from the 5'-end using ILLUMINA® sequencing technology, which can generate sequencing reads of up to 300 bp only. Sequencing of the V/J junction is thus usually performed from the constant region, crossing the J segment, the CDR3 region and part of the V segment. However, sequencing errors increase with the length of the sequencing read, and are thus most frequently introduced in the V segments—the region most challenging to correctly assign due to the high homology between different V segments. Consequently, sequencing starting from the constant region may lead to a reduction in the number of V segments that can be identified unambiguously. While this caveat can be avoided by paired-end sequencing, such modification of the protocol will significantly increase the duration and cost associated with this method.

SUMMARY

With each of the current methods exhibiting significant shortcomings, there is thus a considerable need for a TCR sequencing technology that provides TCR repertoire data with high sensitivity and reliability.

Disclosed herein are methods and kits for sequencing of T-cell receptor repertoires and other immune cell repertoires, such as B-cell repertoires, with high sensitivity and reliability. In one embodiment, the methods include the steps of (1) providing RNA from T-cells, (2) transcribing RNA into complimentary RNA (cRNA), (3) reverse transcribing the cRNA into cDNA while introducing a common adapter to the 5' end of the cDNA products, (4) amplifying the cDNA using a single primer pair, (5) further amplifying with PCR products with a single primer pair which introduces adapters for next generation sequencing, wherein the first primer binds to the common adapter region, and wherein the second primer binds to the constant region of the TCR gene, and (6) sequencing the PCR products. In one embodiment, the methods include the steps of (1) providing RNA from T-cells, (2) reverse transcribing the RNA into cDNA, (3) generating second strand cDNA while introducing a common adapter to the 5' end of the cDNA products, (4) amplifying the cDNA using a single primer pair, (5) further amplifying with PCR products with a single primer pair which introduces adapters for next generation sequencing, wherein the first primer binds to the common adapter region, and wherein the second primer binds to the constant region of the TCR gene, and (6) sequencing the PCR products. These embodiments are also called SEQTR method (Sequencing T-cell Receptors). Also provided are kits containing primer mixtures for the sequencing of T-cell receptor repertoires. Similar methods and kits for sequencing of B-cell receptor repertoires are provided.

According to one aspect, methods for sequencing immune cell receptor genes are provided. The methods include (1) providing RNA from immune cells; 2)(a) optionally transcribing the RNA into complementary RNA (cRNA), followed by reverse transcribing the cRNA into complementary DNA (cDNA) using one or more primers that comprise a first adapter sequence, wherein each 5' end of the cDNA produced by reverse transcription contains the first adapter sequence; (2)(b) if step (2)(a) is not performed, reverse transcribing the RNA into complementary DNA (cDNA), followed by transcribing the cDNA into second strand cDNA using one or more primers that comprise a first adapter sequence, wherein each 5' end of the cDNA produced by transcribing the cDNA into second strand cDNA contains the first adapter sequence; (3) amplifying the cDNA to produce a first amplification product using a first primer pair comprising a first primer that hybridizes to the first adapter sequence and a second primer that hybridizes to a constant region of immune cell receptor gene; (4) amplifying the first amplification product to produce a second amplification product using a second primer pair, in which (i) a first primer of the second primer pair binds to the adapter sequence at the 5' end of the second amplification product, (ii) the second primer of the second primer pair binds to the constant region of immune cell receptor gene in the second amplification product, and (iii) the first and second primers comprise adapter sequences for sequencing; and (5) sequencing the second amplification product.

In some embodiments, the reverse transcription step results in PCR products ranging from 150-600 bp. In some embodiments, the immune cell receptor genes are T-cell receptor (TCR) genes or B-cell receptor (BCR) genes.

In some embodiments, the one or more primers used for reverse transcription (step (2)(a)) or second strand cDNA synthesis (step (2)(b)) hybridize to TCR α chain V segments. In some embodiments, the one or more primers used for reverse transcription (step (2)(a)) or second strand cDNA synthesis (step (2)(b)) comprise one or more of SEQ ID NOs: 1-50 or SEQ ID NOs: 261-310.

In some embodiments, the one or more primers used for reverse transcription (step (2)(a)) or second strand cDNA synthesis (step (2)(b)) hybridize to TCR β chain V segments. In some embodiments, the one or more primers used for reverse transcription (step (2)(a)) or second strand cDNA synthesis (step (2)(b)) comprise one or more of SEQ ID NOs: 51-100 or SEQ ID NOs: 311-360.

In some embodiments, the one or more primers used for reverse transcription (step (2)(a)) or second strand cDNA synthesis (step (2)(b)) hybridize to TCR γ chain V segments.

In some embodiments, the one or more primers used for reverse transcription (step (2)(a)) or second strand cDNA synthesis (step (2)(b)) hybridize to TCR δ chain V segments.

In some embodiments, the one or more primers used for reverse transcription (step (2)(a)) or second strand cDNA synthesis (step (2)(b)) hybridize to BCR heavy chain V segments.

In some embodiments, the one or more primers used for reverse transcription (step (2)(a)) or second strand cDNA synthesis (step (2)(b)) hybridize to BCR light chain V segments.

In some embodiments, the one or more primers used for reverse transcription (step (2)(a)) or second strand cDNA synthesis (step (2)(b)) contain a nucleotide barcode sequence. In some embodiments, the nucleotide barcode comprises 6 to 20 nucleotides. In some embodiments, the nucleotide barcode consists of 9 nucleotides. In some embodiments, the nucleotide barcode consists of the sequence NNNNTNNNN, NNNNANNNN or HHHHHNNNN.

In some embodiments, the first adapter sequence of the one or more primers used for the reverse transcription (step (2)(a)) or second strand cDNA synthesis (step (2)(b)) comprises a T7 adapter or an ILLUMINA® adapter.

In some embodiments, the immune cells are T-cells and wherein the second primer of the first pair of primers hybridizes to the constant region of a TCR gene.

In some embodiments, the immune cells are B-cells and wherein the second primer of the first pair of primers hybridizes to the constant region of a BCR gene.

In some embodiments, the sequencing is next generation sequencing.

In some embodiments, the RNA from the immune cells is obtained by mixing immune cells with carrier cells before RNA extraction.

In some embodiments, the immune cells are tumor-infiltrating lymphocytes.

In some embodiments, the immune cells are CD4 or CD8 positive T-cells.

In some embodiments, the immune cells are purified from peripheral blood mononuclear cells (PBMC) before RNA extraction.

In some embodiments, the immune cells are part of a mixture of PBMC.

In some embodiments, the immune cells are derived from a mammal. In some embodiments, the mammal is a human or a mouse.

According to another aspect, kits for sequencing of T-cell receptors are provided. The kits include at least one primer which comprises a TCR α chain V segment portion of any one of SEQ ID NOs: 1-50 or SEQ ID NOs: 261-310 and a barcode sequence. In some embodiments, the kits include at least one primer including any one of SEQ ID NOs: 1-50 or SEQ ID NOs: 261-310.

According to another aspect, kits for sequencing of T-cell receptors are provided. The kits include at least one primer which comprises a TCR τ3 chain V segment portion of any one of SEQ ID NOs: 51-100 or SEQ ID NOs: 311-360 and a barcode sequence. In some embodiments, the kits include at least one primer comprising any one of SEQ ID NOs: 51-100 or SEQ ID NOs: 311-360.

These and other features, aspects, and advantages of the present invention will become better understood with regard to the following description, appended claims and accompanying drawings.

BRIEF DESCRIPTION OF THE DRAWINGS

FIG. 9A CD8 positive T-cells were isolated from peripheral blood mononuclear cells (PBMC), FIG. 9B additionally purified using tetramers conjugated with neo-epitope TEDYMIHII (SEQ ID NO:236) or FIG. 9C additionally purified using tetramer conjugated with neo-epitope (same as in FIG. 9B) and subsequently expanded in vitro. The TCR repertoires of the respective samples were sequenced using the SEQTR method and the relative frequencies of all observed V/J rearrangements/combinations plotted.

FIGS. 10A-10C illustrate the overlap of TCRs identified using a single cell cloning method and TCRs identified using the SEQTR method. FIG. 10A: T-cells were isolated from PBMC and subjected to an additional round of purification using tetramers conjugated with neo-epitope TEDYMIHII (SEQ ID NO: 236). The resulting cell population was then sorted by fluorescence-activated cell sorting (FACS). Half of the sorted cells were subjected to the SEQTR method to sequence the TCR repertoire. For the other half of cells, individual T-cell clones were isolated and expanded in vitro (single cell cloning). Once the clones were established, the TCR genes of each T-cell clones were amplified and sequenced using classical Sanger sequencing. FIG. 10B: The table shows all six TCRs identified using the single cell cloning method. The sequences correspond to SEQ ID NOs: 237 through 242 from top to bottom, respectively. FIG. 10C: The table shows the eight most frequent TCRs identified using the SEQTR method. The sequences correspond to SEQ ID NOs: 243 through 250 from top to bottom, respectively.

FIG. 12 illustrates the amplification of TCR genes from T-cells that are part of a PBMC mixture (upper panel) or from isolated, CD4 positive T-cells (lower panel), using steps 2 to 4 of the SEQTR method.

DETAILED DESCRIPTION

Figure 1:
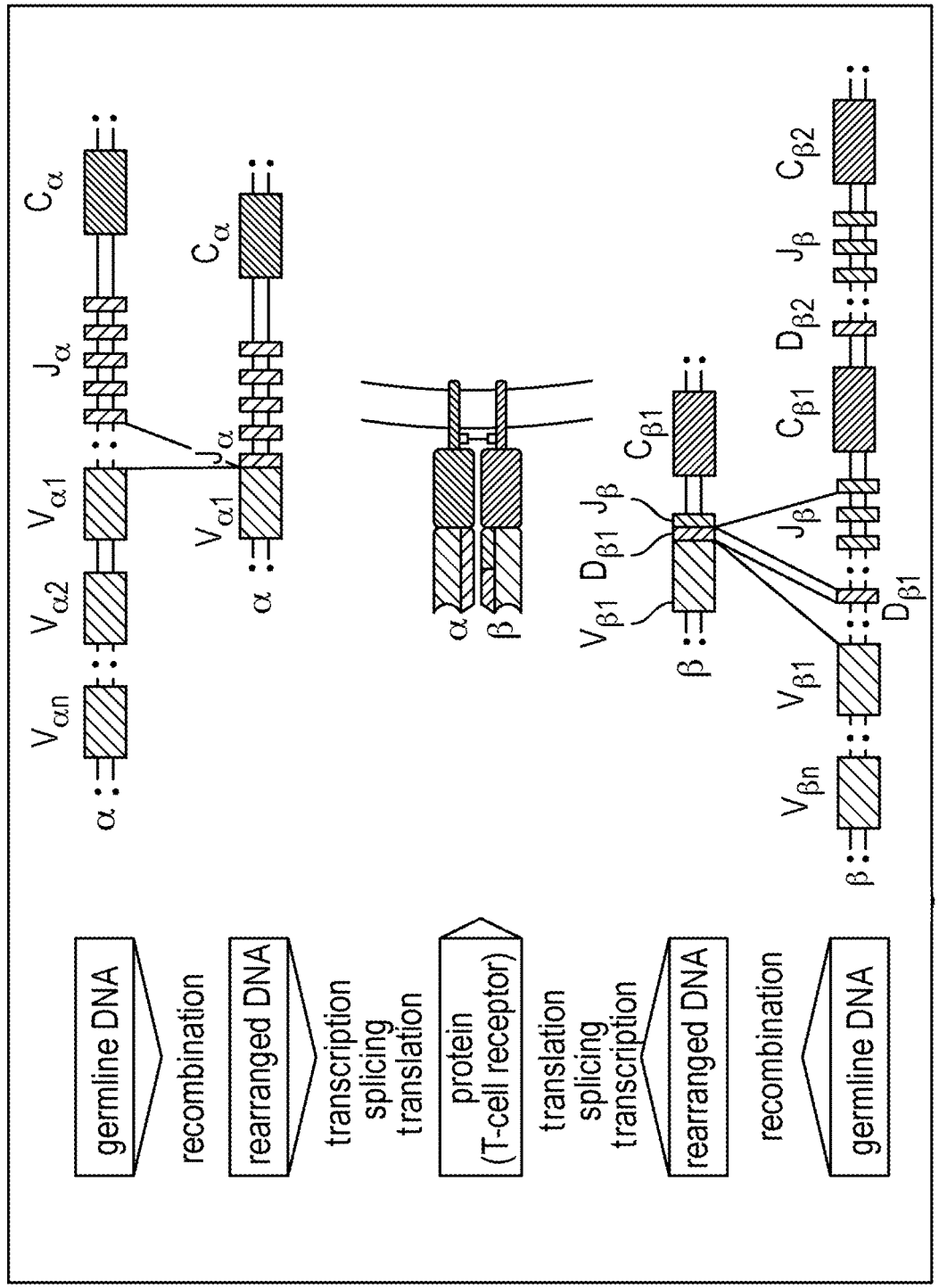
FIG. 1 shows the arrangement of (variable) V, diversity (D), joining (J) and constant (C) regions in the α and β chains of T-cell receptors. Figure taken from Murphy, K., Travers, P., Walport, M., & Janeway, C. (2012). Janeway's immunobiology. New York: Garland Science.
Figure 2:
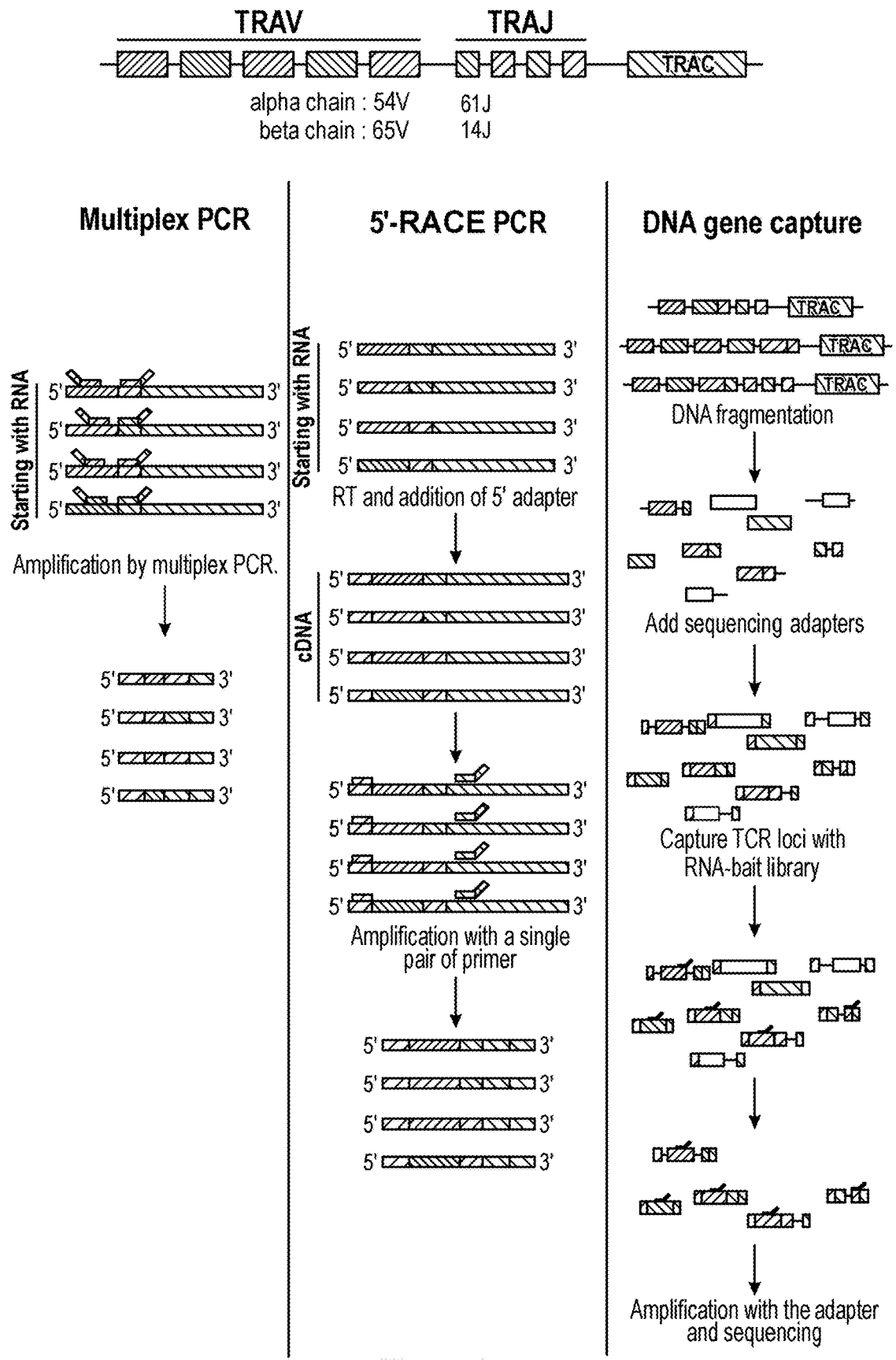
FIG. 2 is an illustration of three different TCR sequencing techniques that have been employed in the past.

In light of the shortcomings of existing techniques to sequence TCRs, it was determined that a TCR sequencing technology providing the most reliable TCR repertoire data includes the following features:
1) The amplification of TCR genes is linear and does not employ multiplex PCR, therefore avoiding artificial overrepresentation of certain TCR sequences.
2) The method is based on RNA and not DNA, thus only providing data for TCR sequences that have undergone rearrangement and that are actually expressed in T-cells.
3) TCR genes are sequenced from the 5' end, providing high quality sequencing data and therefore maximizing reliable and unambiguous identification of the highly homologous V segments.
4) Sequencing data include the highly variable CDR3 region, therefore facilitating unambiguous identification of TCR sequences.

The disclosed methods, systems and kits fulfill all these criteria. These same features are of use in sequencing receptors from other immune cells, such as B-cells.

In some embodiments, the immune cell receptor sequencing methods comprise the following steps:
(1) Providing total RNA (RNA) as the starting material;
(2)(a) Transcribing the RNA into complimentary RNA (cRNA) followed by reverse transcribing the cRNA into cDNA, using primers that introduce a common adapter to the 5' end of the cDNA products;
(2)(b) If step (2)(a) is not performed, reverse transcribing the RNA into complementary DNA (cDNA), followed by transcribing the cDNA into second strand cDNA using one or more primers that comprise a first adapter sequence, wherein each 5' end of the cDNA produced by transcribing the cDNA into second strand cDNA contains the first adapter sequence;
(3) Amplifying the cDNA products using a single primer pair;
(4) Amplifying the PCR products of step 4 using a single primer pair, in which:
  i. the primers introduce adapters for next generation sequencing, and
  ii. the first primer binds to the common adapter region at the 5' end of the PCR products, and
  iii. the second primer binds to a region of the PCR products that constitutes the constant region of the TCR to be sequenced; and
(5) Sequencing the PCR products generated in step 4.

Genetic Information to be Sequenced

The genetic information to be sequenced is immune cell receptor genes. In the some embodiments of the invention, the genetic information to be sequenced comprises T-cell receptors genes. In some embodiments, the TCR genes that are sequenced encode TCR α chains or TCR β chains. In other embodiments, TCR genes that are sequenced encode TCR δ chains or TCR γ chains.

In other embodiments of the invention, the genetic information to be sequenced comprises B-cell receptor (BCR) genes.

Starting Material (Step 1)

RNA is isolated from immune cells and used to generate complimentary RNA (cRNA) by in vitro transcription. This is in contrast to existing TCR sequencing techniques that use DNA or complementary DNA (cDNA) as their genetic starting material.

In some embodiments, the immune cells from which RNA is obtained are isolated from peripheral blood mononuclear cells before RNA extraction. The immune cells are, in some embodiments, T-cells or B-cells.

In some embodiments, T-cells from which RNA is obtained express CD4 or CD8.

Generation of cRNA Through Transcription (Step (2)(a))

Complementary RNA (cRNA) is generated by in vitro transcription. Any method for performing in vitro transcription known to those skilled in molecular biology can be used. In some embodiments, the in vitro transcription in step 2 is performed using commercially available kits, such as the AMBION™ kits available from Thermo Fisher Scientific.

Reverse Transcription (Step (2)(a))

Reverse transcription of the cRNA is performed to generate complementary DNA (cDNA). Methods known to persons skilled in molecular biology are used to reverse transcribe cRNA to cDNA. Typically, such methods include hybridization of a primer to the 3' end of the cRNA molecule and production of DNA starting at the hybridized primer using a reverse transcriptase enzyme and appropriate nucleotides, salts and buffers.

The choice of primers used in the reverse transcription reaction is important for the ability to differentiate between homologous, yet distinct, immune cell receptor sequences with high degrees of certainty and allows shortening of the V segments from the 5' end, generating PCR products with a size of 250-300 bp. Such a size range of PCR products is optimal for next generation sequencing.

Figure 3:
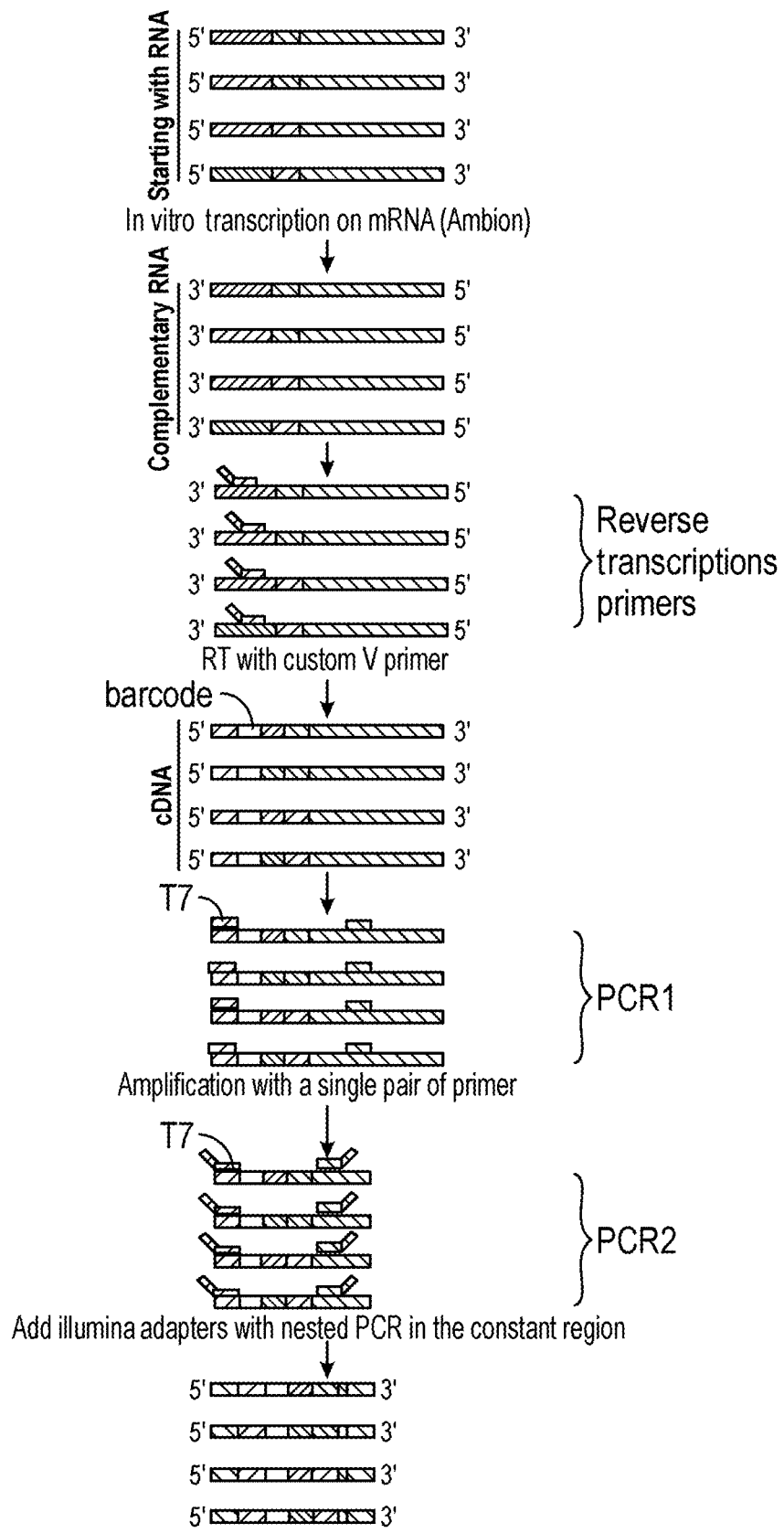
FIG. 3 provides an overview of the SEQTR method, using TCR α chains as an example. Each bar represents a TCR α chain gene. In RNA and cRNA molecules, the order of the segments is, left to right: V segments, J segments, and the constant region. Barcode regions are added in cDNA molecule to the left of V segments; and T7 adapter regions are added to the left of the barcodes (also indicated by T7 primer amplification in PCR1 and PCR2 steps). ILLUMINA® sequencing adapters are added in the PCR2 step to the 5' and 3' ends of the molecules, as shown in the last set of molecules.

In some embodiments, the primers used for the reverse transcription are designed to bind within the V segments of the TCR genes (see FIG. 3). For example, the reverse transcription primers are designed to bind close enough to the V(D)J junction so that the resulting sequencing data cover the CDR3 of the V segment and the J segment, but far enough from the V(D)J junction to still allow differentiation between different V regions.

In some embodiments of the invention, a set of preferred primers is used (see, e.g., the sequences in Table 2 and Table 4, and Table 8 and Table 9). Due to the high degree of homology between different V segments, some of the primers described in Table 2 and Table 4 (and Table 8 and Table 9) bind to more than one V segment (see Table 3 and Table 5; the binding sites in their respective V segments for primers SEQ ID NOs: 1-100 and SEQ ID NOs: 261-360 are indicated in Table 15 and Table 16). However, the design of the primers presented in Table 2 and Table 4 (likewise Table 8 and Table 9) still allows the unambiguous assignment/identification of the respective V segments based on differences between the V segments downstream of the primer-binding site. In an alternative embodiment of the invention, only a subset of the preferred primers SEQ ID NOs: 1-100 and SEQ ID NOs: 261-360 may be used for the reverse transcription.

In yet another embodiment of the invention, primer sets may be used that bind to different regions in the V segments when compared to the primers having SEQ ID NOs: 1-100 and SEQ ID NOs: 261-360. For instance, the binding site of one or more primers may be moved towards the CDR3 region of the TCR gene. Due to the high degree of homology between V segments, the further the primer binding site is moved in the direction of the CDR3 region of the TCR gene, the larger the likelihood that the resulting sequencing data are consistent with the presence of more than one V segment. While, in these cases, the respective V segments cannot be assigned or identified unambiguously, the number of V/J segments possibly present in the sample can often be narrowed down to a small subset. Depending on the application, such limited information can already be of value to the experimenter.

In another embodiment of the invention, the binding site of one or more primers may be moved towards the 5' end of the V segment as compared to the binding sites of primers SEQ ID NOs: 1-100 and SEQ ID NOs: 261-360. Many next generation sequencing technologies generate sequencing reads that are 150 bp long. Therefore, the further the primer binding site is moved towards the 5' end of the V segment, the larger is the probability that the respective J segment (which can be found at the 3' end of the resulting sequencing read) cannot be identified unambiguously. However, this problem can be circumvented by using alternative sequencing technologies that generate reads >150 bp.

In some embodiments, the primers used in step (2)(a) additionally contain a unique bar code. Such barcoding of each RNA molecule before the amplification can be used to correct the obtained sequencing results for PCR and sequencing errors.

In some embodiments, the primers for this reverse transcription step introduce a common T7 adapter at the 5' end of the resulting PCR products. However, alternative adapter sequences are possible, including, but not limited to ILLUMINA® adapters and sequences presented in Table 1.

TABLE 1

Examples for alternative nucleotide adapters that can be used instead of a T7 adapter sequence

| SEQ ID NO | Primer name | Primer sequence (5' to 3') |
| --- | --- | --- |
| 251 | Original Eberwine T7 | AAACGACGGCCAGTGAATTGTAATACGACTCACTATAGGCGCT |
| 252 | Affymetrix T7 | GGCCAGTGAATTGTAATACGACTCACTATAGGGAGGCGGT |
| 253 | Invitrogen T7 | TAATACGACTCACTATAGGGAGGCGGT |
| 254 | Ambion T7 | GGTAATACGACTCACTATAGGGAGAAGAGT |
| 255 | Agilent T7 | AATTAATACGACTCACTATAGGGAGAT |

Reverse Transcription (Step (2)(b))

Reverse transcription of the RNA is performed to generate complementary DNA (cDNA). Methods known to persons skilled in molecular biology are used to reverse transcribe RNA to cDNA. Typically, such methods include hybridization of a primer to the 3' end of the RNA molecule and production of DNA starting at the hybridized primer using a reverse transcriptase enzyme and appropriate nucleotides, salts and buffers.

Transcribing the cDNA into Second Strand cDNA (Step (2)(b))

Following generation of cDNA, second strand cDNA is synthesized using methods known to persons skilled in molecular biology. Typically, such methods include hybridization of a primer to the 3' end of the cDNA molecule and production of second strand cDNA starting at the hybridized primer using a polymerase enzyme and appropriate nucleotides, salts and buffers.

The choice of primers used in the second strand synthesis reaction is step (2)(b) is as described above for reverse transcription in step (2)(a). The choice of primers is important for the ability to differentiate between homologous, yet distinct, immune cell receptor sequences with high degrees of certainty and allows shortening of the V segments from the 5' end, generating PCR products with a size of 250-300 bp. Such a size range of PCR products is optimal for next generation sequencing.

Amplification (Step 3)

Amplification of the cDNA is performed by any of the well-known amplification reactions, such as polymerase chain reaction (PCR). Methods known to persons skilled in the molecular biology art are used to amplify the cDNA or a portion thereof (e.g., as depicted in FIG. 3). Typically, such methods include hybridization of a pair of primers to the cDNA molecule and amplification of the DNA sequence between the hybridized primers using a polymerase enzyme and appropriate nucleotides, salts and buffers.

In some embodiments, the first primer of a primer pair used in an amplification step binds to the common adapter region of the cDNA products produced in step 3 and the second primer of the primer pair binds to a region of the cDNA products that constitutes the constant region of the TCR to be sequenced (see FIG. 3).

Of note, not all reverse primers designed to target the constant region of the TCR gene perform equally well in this reaction. For example, the primers listed in Table 7 all failed to provide good amplification with the selected T7 5' adapter. Therefore, in certain embodiments, the primers listed in are Table 6 used in this amplification step.

Amplification (Step 4)

A second amplification step is performed to add additional sequences to the amplified molecules, such as sequences that are useful in downstream DNA sequencing reactions. In some embodiments of the present invention, the primers used in this step add appropriate adapters for ILLUMINA® sequencing.

Sequencing (Step 5)

Various suitable sequencing methods described herein or known in the art are used to obtain sequence information from the amplified sequences from the nucleic acid molecules within a sample. For example, sequencing methodologies that can be used in the methods disclosed herein include: classic Sanger sequencing, massively parallel sequencing, next generation sequencing, polony sequencing, 454 pyrosequencing, ILLUMINA® sequencing, SOLEXA® sequencing, SOLID™ sequencing (sequencing by oligonucleotide ligation and detection), ion semiconductor sequencing, DNA nanoball sequencing, heliscope single molecule sequencing, single molecule real time sequencing, nanopore DNA sequencing, tunneling currents DNA sequencing, sequencing by hybridization, sequencing with mass spectrometry, microfluidic Sanger sequencing, microscopy-based sequencing, RNA polymerase sequencing, in vitro virus high-throughput sequencing, Maxam-Gilbert sequencing, single-end sequencing, paired-end sequencing, deep sequencing, and/or ultra-deep sequencing.

Definitions

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

As used herein, a "primer" is a nucleic acid molecule that hybridizes with a complementary (including partially complementary) polynucleotide strand. Primers can be DNA molecules, RNA molecules, or DNA or RNA analogs. DNA or RNA analogs can be synthesized from nucleotide analogs.

EXAMPLES

Example 1: Exemplary Protocol for the SEQTR Method Using T7 and TrueSeq Adapters TCR α and β chain genes were sequenced in two independent reactions.

1) Starting material and RNA extraction

To obtain sufficient amounts of RNA in the extraction, a minimum of 500,000 T-cells were used as starting material. Alternatively, and especially in instances where fewer T-cells were available, T-cells were mixed with 50,000 mouse 3T3 cells that served as carrier. T-cell RNA was extracted using the RNeasy® Micro Kit from Qiagen Inc. according the manufacturer's instruction with the following modification: Elution was performed with 20 µl of water preheated to 50° C. RNA quality and quantity was verified using a fragment analyzer.

2) cRNA synthesis by in vitro transcription (IVT):

In vitro transcription of isolated RNA was performed using the MessageAmp™ II aRNA Amplification Kit from Ambion® (Thermo Fisher Scientific), which contains enzymes, buffers and nucleotides required to perform the first and second strand cDNA and the in vitro transcription. The kit also provides all columns and reagents needed for the cDNA and cRNA purifications. RNA amplification was performed according to the manufacturer's instructions with the following modifications: 1) Between 0.5 and 1 µg of total RNA as was used as starting material. 2) The IVT was performed in a final volume of 40 µl, and incubated at 37° C. for 16 h. Purified cRNA was quantified by absorbance using a NanoDrop™ spectrophotometer (Thermo Fisher Scientific).

3) cDNA synthesis by reverse transcription:

The reverse transcription of the cRNA was performed with the SuperScript® III from Invitrogen (Thermo Fisher Scientific). The kit provides the enzyme, the buffer and the dithiothreitol (DTT) needed for the reaction. Deoxynucleotides (dNTPs) and RNAsin® Ribonuclease inhibitor were purchased from Promega. The sequences for the primers used for the reverse transcription can be found in Table 2 (primers for sequencing TCR α chain genes) and Table 4 (primers for sequencing TCR β chain genes).

500 ng of cRNA were used as starting material for the reverse transcription. cRNA was mixed with 1 µl hTRAV or hTRBV primers mix (2 µM each) and 1 µl dNTP (25 mM) in a final volume of 13 µl. The mix was first incubated at 70° C. for 10 min, then at 50° C. for 30 s. 4 µl 5× buffer, 1 µl DTT (100 mM), 1 µl SuperScript III and 1 μl RNAsin® were added to the mix. The samples were subsequently incubated for at 55° C. 1 h and then at 85° C. for 5 min. After the cDNA synthesis, 1 μg DNase-free RNase (Roche) was added to the cDNA and incubated at 37° C. for 30 min to remove the cRNA.

4) TCR gene amplification:
TCR gene amplification was performed using a Phusion® High-Fidelity DNA polymerase (New England Biolabs) under the following conditions:
PCR mix: 1 μl cDNA from step 3, 1 μl dNTPs (25 mM), 1 μl primer mix (10 μM each, see Table 5), 5 μl 5× buffer and 0.2 μl Phusion® enzyme in a total volume of 25 μl.
PCR conditions:
  94° C. for 5 min
  20 to 30 cycles of
    98° C. for 10 s
    55° C. for 30 s
    72° C. for 30 s
  72° C. for 2 min
PCR products were purified either from agarose gels (using a Qiaquick Gel Extraction Kit from Qiagen) or using an ExoSAP-IT® PCR Product Cleanup Kit (Affymetrix) according to the manufacturer's instructions.

5) Addition of Next Generation Sequencing adapters:
ILLUMINA® sequencing adapters were added by PCR using a Phusion® High-Fidelity DNA polymerase (New England Biolabs). One third of the purified PCR product obtained in step 4 was mixed with 0.5 μl dNTPs (25 mM), 1 μl primer mix (10 μM each, see Table 8), 5 μl 5× buffer and 0.2 μl Phusion® enzyme in a total volume of 25 μl.
PCR conditions:
  94° C. for 5 min
  perform 12 cycles of:
    98° C. for 10 s
    55° C. for 30 s
    72° C. for 30 s
  72° C. for 2 min 6) TCR library purification:
10 μl of the PCR product from step 5 were purified using an ExoSAP-IT® PCR Product Cleanup Kit (Affymetrix) or Ampure XP beads (Beckman Coulter) according to the manufacturer's instruction. Samples could then directly be used for ILLUMINA® sequencing.

TABLE 2

Preferred primer sequences for amplification of TCR α chain V segments. N can be any nucleotide. The sequences for primers presented in this table consist of three parts (listed from 5' to 3'): T7 adapter, barcode and TCR α chain V segment.

| SEQ ID NO | Primer name | Sequence T7 adapter portion of the primer | Sequence barcode portion of the primer | Sequence TCR α chain V segment portion of the primer |
|---|---|---|---|---|
| 1 | hTRAV1-1 | TGTAATACGACTCACTATAG | NNNNTNNNN | CTTCTACAGGAGCTCCAGATGAAAG |
| 2 | hTRAV1-2 | TGTAATACGACTCACTATAG | NNNNTNNNN | CTTTTGAAGGAGCTCCAGATGAAAG |
| 3 | hTRAV2 | TGTAATACGACTCACTATAG | NNNNTNNNN | TGCTCATCCTCCAGGTGCGGGA |
| 4 | hTRAV3 | TGTAATACGACTCACTATAG | NNNNTNNNN | GAAGAAACCATCTGCCCTTGTGA |
| 5 | hTRAV4 | TGTAATACGACTCACTATAG | NNNNTNNNN | CCTGCCCCGGGTTTCCCTGAGCGAC |
| 6 | hTRAV5 | TGTAATACGACTCACTATAG | NNNNTNNNN | TCTCTGCGCATTGCAGACACCCA |
| 7 | hTRAV6 | TGTAATACGACTCACTATAG | NNNNTNNNN | TTGTTTCATATCACAGCCTCCCA |
| 8 | hTRAV7 | TGTAATACGACTCACTATAG | NNNNTNNNN | GCTTGTACATTACAGCCGTGCA |
| 9 | hTRAV8-1/8-3 | TGTAATACGACTCACTATAG | NNNNTNNNN | ATCTGAGGAAACCCTCTGTGCA |
| 10 | hTRAV8-2/8-4 | TGTAATACGACTCACTATAG | NNNNTNNNN | ACCTGACGAAACCCTCAGCCCAT |
| 11 | hTRAV8-5 | TGTAATACGACTCACTATAG | NNNNTNNNN | CCTATGCCTGTCTTTACTTTAATC |
| 12 | hTRAV8-6 | TGTAATACGACTCACTATAG | NNNNTNNNN | CTTGAGGAAACCCTCAGTCCATAT |
| 13 | hTRAV8-7 | TGTAATACGACTCACTATAG | NNNNTNNNN | GAAACCATCAACCCATGTGAGTGA |
| 14 | hTRAV9-1 | TGTAATACGACTCACTATAG | NNNNTNNNN | ACTTGGAGAAAGACTCAGTTCAA |
| 15 | hTRAV9-2 | TGTAATACGACTCACTATAG | NNNNTNNNN | ACTTGGAGAAAGGCTCAGTTCAA |
| 16 | hTRAV10 | TGTAATACGACTCACTATAG | NNNNTNNNN | CTGCACATCACAGCCTCCCA |
| 17 | hTRAV11 | TGTAATACGACTCACTATAG | NNNNTNNNN | GTTTGGAATATCGCAGCCTCTCAT |
| 18 | hTRAV12-1 | TGTAATACGACTCACTATAG | NNNNTNNNN | CCCTGCTCATCAGAGACTCCAAG |
| 19 | hTRAV12-2 | TGTAATACGACTCACTATAG | NNNNTNNNN | CTCTGCTCATCAGAGACTCCAG |
| 20 | hTRAV12-3 | TGTAATACGACTCACTATAG | NNNNTNNNN | CCTTGTTCATCAGAGACTCACAG |
| 21 | hTRAV13-1 | TGTAATACGACTCACTATAG | NNNNTNNNN | TCCCTGCACATCACAGAGACCCAA |

TABLE 2-continued

Preferred primer sequences for amplification of TCR α chain V segments. N can be any nucleotide. The sequences for primers presented in this table consist of three parts (listed from 5' to 3'): T7 adapter, barcode and TCR α chain V segment.

| SEQ ID NO | Primer name | Sequence T7 adapter portion of the primer | Sequence barcode portion of the primer | Sequence TCR α chain V segment portion of the primer |
|---|---|---|---|---|
| 22 | hTRAV13-2 | TGTAATACGACTCACTATAG | NNNNTNNNN | TCTCTGCAAATTGCAGCTACTCAA |
| 23 | hTRAV14 | TGTAATACGACTCACTATAG | NNNNTNNNN | TTGTCATCTCCGCTTCACAACTGG |
| 24 | hTRAV15 | TGTAATACGACTCACTATAG | NNNNTNNNN | GTTTTGAATATGCTGGTCTCTCAT |
| 25 | hTRAV16 | TGTAATACGACTCACTATAG | NNNNTNNNN | CCTGAAGAAACCATTTGCTCAAGA |
| 26 | hTRAV17 | TGTAATACGACTCACTATAG | NNNNTNNNN | TCCTTGTTGATCACGGCTTCCCGG |
| 27 | hTRAV18 | TGTAATACGACTCACTATAG | NNNNTNNNN | ACCTGGAGAAGCCCTCGGTGCA |
| 28 | hTRAV19 | TGTAATACGACTCACTATAG | NNNNTNNNN | CACCATCACAGCCTCACAAGTCGT |
| 29 | hTRAV20 | TGTAATACGACTCACTATAG | NNNNTNNNN | TTTCTGCACATCACAGCCCCTA |
| 30 | hTRAV21 | TGTAATACGACTCACTATAG | NNNNTNNNN | CTTTATACATTGCAGCTTCTCAGCC |
| 31 | hTRAV22 | TGTAATACGACTCACTATAG | NNNNTNNNN | GTACATTTCCTCTTCCCAGACCAC |
| 32 | hTRAV23 | TGTAATACGACTCACTATAG | NNNNTNNNN | CATTGCATATCATGGATTCCCAGC |
| 33 | hTRAV24 | TGTAATACGACTCACTATAG | NNNNTNNNN | GCTATTTGTACATCAAAGGATCCC |
| 34 | hTRAV25 | TGTAATACGACTCACTATAG | NNNNTNNNN | CAGCTCCCTGCACATCACAGCCA |
| 35 | hTRAV26-1 | TGTAATACGACTCACTATAG | NNNNTNNNN | TTGATCCTGCCCCACGCTACGCTGA |
| 36 | hTRAV26-2 | TGTAATACGACTCACTATAG | NNNNTNNNN | TTGATCCTGCACCGTGCTACCTTGA |
| 37 | hTRAV27 | TGTAATACGACTCACTATAG | NNNNTNNNN | GTTCTCTCCACATCACTGCAGCC |
| 38 | hTRAV28 | TGTAATACGACTCACTATAG | NNNNTNNNN | GCCACCTATACATCAGATTCCCA |
| 39 | hTRAV29 | TGTAATACGACTCACTATAG | NNNNTNNNN | TCTCTGCACATTGTGCCCTCCCA |
| 40 | hTRAV30 | TGTAATACGACTCACTATAG | NNNNTNNNN | CCCTGTACCTTACGGCCTCCCAGCT |
| 41 | hTRAV31 | TGTAATACGACTCACTATAG | NNNNTNNNN | CTTATCATATCATCATCACAGCCA |
| 42 | hTRAV32 | TGTAATACGACTCACTATAG | NNNNTNNNN | TCCCTGCATATTACAGCCACCCAA |
| 43 | hTRAV33 | TGTAATACGACTCACTATAG | NNNNTNNNN | ACCTCACCATCAATTCCTTAAAAC |
| 44 | hTRAV34 | TGTAATACGACTCACTATAG | NNNNTNNNN | TCCCTGCATATCACAGCCTCCCAG |
| 45 | hTRAV35 | TGTAATACGACTCACTATAG | NNNNTNNNN | CTTCCTGAATATCTCAGCATCCAT |
| 46 | hTRAV36 | TGTAATACGACTCACTATAG | NNNNTNNNN | TCCTGAACATCACAGCCACCCAG |
| 47 | hTRAV37 | TGTAATACGACTCACTATAG | NNNNTNNNN | TCCCTGCACATACAGGATTCCCAG |
| 48 | hTRAV38 | TGTAATACGACTCACTATAG | NNNNTNNNN | CAAGATCTCAGACTCACAGCTGG |
| 49 | hTRAV39 | TGTAATACGACTCACTATAG | NNNNTNNNN | CCGTCTCAGCACCCTCCACATCA |
| 50 | hTRAV40 | TGTAATACGACTCACTATAG | NNNNTNNNN | CCATTGTGAAATATTCAGTCCAGG |

TABLE 3

V segments targeted by each primer used for the amplification of TCR α chain V segments.

| SEQ ID NO | Primer | Targeted V segment(s) |
|---|---|---|
| 1 | hTRAV1-1 | hTRAV01-1 |
| 2 | hTRAV1-2 | hTRAV01-2 |
| 3 | hTRAV2 | hTRAV02 |
| 4 | hTRAV3 | hTRAV03 |
| 5 | hTRAV4 | hTRAV04 |
| 6 | hTRAV5 | hTRAV05 |

TABLE 3-continued

V segments targeted by each primer used for the amplification of TCR α chain V segments.

| SEQ ID NO | Primer | Targeted V segment(s) |
|---|---|---|
| 7 | hTRAV6 | hTRAV06 |
| 8 | hTRAV7 | hTRAV07 |
| 9 | hTRAV8-1/8-3 | hTRAV08-1, hTRAV08-3 |
| 10 | hTRAV8-2/8-4 | hTRAV08-2, hTRAV08-4 |
| 11 | hTRAV8-5 | hTRAV08-5 |
| 12 | hTRAV8-6 | hTRAV08-6 |
| 13 | hTRAV8-7 | hTRAV08-7 |
| 14 | hTRAV9-1 | hTRAV09-1 |
| 15 | hTRAV9-2 | hTRAV09-2 |
| 16 | hTRAV10 | hTRAV10, hTRAV41 |
| 17 | hTRAV11 | hTRAV11 |
| 18 | hTRAV12-1 | hTRAV12-1 |
| 19 | hTRAV12-2 | hTRAV12-2 |
| 20 | hTRAV12-3 | hTRAV12-3 |
| 21 | hTRAV13-1 | hTRAV13-1 |
| 22 | hTRAV13-2 | hTRAV13-2 |
| 23 | hTRAV14 | hTRAV14 |
| 24 | hTRAV15 | hTRAV15 |
| 25 | hTRAV16 | hTRAV16 |
| 26 | hTRAV17 | hTRAV17 |
| 27 | hTRAV18 | hTRAV18 |
| 28 | hTRAV19 | hTRAV19 |
| 29 | hTRAV20 | hTRAV20 |
| 30 | hTRAV21 | hTRAV21 |
| 31 | hTRAV22 | hTRAV22 |
| 32 | hTRAV23 | hTRAV23 |
| 33 | hTRAV24 | hTRAV24 |
| 34 | hTRAV25 | hTRAV25 |
| 35 | hTRAV26-1 | hTRAV26-1 |
| 36 | hTRAV26-2 | hTRAV26-2 |
| 37 | hTRAV27 | hTRAV27 |
| 38 | hTRAV28 | hTRAV28 |
| 39 | hTRAV29 | hTRAV29 |
| 40 | hTRAV30 | hTRAV30 |
| 41 | hTRAV31 | hTRAV31 |
| 42 | hTRAV32 | hTRAV32 |
| 43 | hTRAV33 | hTRAV33 |
| 44 | hTRAV34 | hTRAV34 |
| 45 | hTRAV35 | hTRAV35 |
| 46 | hTRAV36 | hTRAV36 |
| 47 | hTRAV37 | hTRAV37 |
| 48 | hTRAV38 | hTRAV38-1, hTRAV38-2 |
| 49 | hTRAV39 | hTRAV39 |
| 50 | hTRAV40 | hTRAV40 |

TABLE 4

Preferred primer sequences for amplification of TCR β chain V segments. N can be any nucleotide. The sequences for primers presented in this table consist of three parts (listed from 5' to 3'): T7 adapter, barcode and TCR β chain V segment.

| SEQ ID NO | Primer name | Sequence T7 adapter portion of the primer | Sequence barcode portion of the primer | Sequence TCR β chain V segment portion of the primer |
|---|---|---|---|---|
| 51 | hTRBV1 | TGTAATACGACTCACTATAG | NNNNANNNN | GTGGTCGCACTGCAGCAAGAAGA |
| 52 | hTRBV2 | TGTAATACGACTCACTATAG | NNNNANNNN | GATCCGGTCCACAAAGCTGGAGGA |
| 53 | hTRBV3-1 | TGTAATACGACTCACTATAG | NNNNANNNN | CATCAATTCCCTGGAGCTTGGTGA |
| 54 | hTRBV4-1 | TGTAATACGACTCACTATAG | NNNNANNNN | TTCACCTACACGCCCTGCAGCCAG |
| 55 | hTRBV4-2 | TGTAATACGACTCACTATAG | NNNNANNNN | TTCACCTACACACCCTGCAGCCAG |
| 56 | hTRBV5-1 | TGTAATACGACTCACTATAG | NNNNANNNN | GAATGTGAGCACCTTGGAGCTGG |
| 57 | hTRBV5-2 | TGTAATACGACTCACTATAG | NNNNANNNN | TACTGAGTCAAACACGGAGCTAGG |
| 58 | hTRBV5-3 | TGTAATACGACTCACTATAG | NNNNANNNN | GCTCTGAGATGAATGTGAGTGCCT |
| 59 | hTRBV5-4 | TGTAATACGACTCACTATAG | NNNNANNNN | CTGAGCTGAATGTGAACGCCTT |
| 60 | hTRBV6-1 | TGTAATACGACTCACTATAG | NNNNANNNN | GAGTTCTCGCTCAGGCTGGAGT |
| 61 | hTRBV6-2 | TGTAATACGACTCACTATAG | NNNNANNNN | CTGGGGTTGGAGTCGGCTGCTC |
| 62 | hTRBV6-4 | TGTAATACGACTCACTATAG | NNNNANNNN | CCCCTCACGTTGGCGTCTGCTG |
| 63 | hTRBV6-5 | TGTAATACGACTCACTATAG | NNNNANNNN | TCCCGCTCAGGCTGCTGTCGGC |
| 64 | hTRBV6-6 | TGTAATACGACTCACTATAG | NNNNANNNN | GATTTCCCGCTCAGGCTGGAGT |
| 65 | hTRBV6-7 | TGTAATACGACTCACTATAG | NNNNANNNN | TCCCCCTCAAGCTGGAGTCAGCT |
| 66 | hTRBV6-8 | TGTAATACGACTCACTATAG | NNNNANNNN | TCCCACTCAGGCTGGTGTCGGC |
| 67 | hTRBV7-1 | TGTAATACGACTCACTATAG | NNNNANNNN | CTCTGAAGTTCCAGCGCACACA |
| 68 | hTRBV7-2 | TGTAATACGACTCACTATAG | NNNNANNNN | GATCCAGCGCACACAGCAGGAG |
| 69 | hTRBV7-3 | TGTAATACGACTCACTATAG | NNNNANNNN | ACTCTGAAGATCCAGCGCACAGA |
| 70 | hTRBV7-5 | TGTAATACGACTCACTATAG | NNNNANNNN | AGATCCAGCGCACAGAGCAAGG |

TABLE 4-continued

Preferred primer sequences for amplification of TCR β chain V segments. N can be any nucleotide. The sequences for primers presented in this table consist of three parts (listed from 5' to 3'): T7 adapter, barcode and TCR β chain V segment.

| SEQ ID NO | Primer name | Sequence T7 adapter portion of the primer | Sequence barcode portion of the primer | Sequence TCR β chain V segment portion of the primer |
|---|---|---|---|---|
| 71 | hTRBV7-6 | TGTAATACGACTCACTATAG | NNNNANNNN | CAGCGCACAGAGCAGCGGGACT |
| 72 | hTRBV7-9 | TGTAATACGACTCACTATAG | NNNNANNNN | GAGATCCAGCGCACAGAGCAGG |
| 73 | hTRBV8-1 | TGTAATACGACTCACTATAG | NNNNANNNN | CCCTCAACCCTGGAGTCTACTA |
| 74 | hTRBV8-2 | TGTAATACGACTCACTATAG | NNNNANNNN | TCCCCAATCCTGGCATCCACCA |
| 75 | hTRBV9 | TGTAATACGACTCACTATAG | NNNNANNNN | CTAAACCTGAGCTCTCTGGAGCT |
| 76 | hTRBV10-1 | TGTAATACGACTCACTATAG | NNNNANNNN | CCCTCACTCTGGAGTCTGCTGC |
| 77 | hTRBV10-2 | TGTAATACGACTCACTATAG | NNNNANNNN | CCCTCACTCTGGAGTCAGCTAC |
| 78 | hTRBV10-3 | TGTAATACGACTCACTATAG | NNNNANNNN | TCCTCACTCTGGAGTCCGCTAC |
| 79 | hTRBV11-1 | TGTAATACGACTCACTATAG | NNNNANNNN | CCACTCTCAAGATCCAGCCTGCA |
| 80 | hTRBV12-1 | TGTAATACGACTCACTATAG | NNNNANNNN | GAGGATCCAGCCCATGGAACCCA |
| 81 | hTRBV12-2 | TGTAATACGACTCACTATAG | NNNNANNNN | CTGAAGATCCAGCCTGCAGAGC |
| 82 | hTRBV12-3 | TGTAATACGACTCACTATAG | NNNNANNNN | CAGCCCTCAGAACCCAGGGACT |
| 83 | hTRBV13 | TGTAATACGACTCACTATAG | NNNNANNNN | GAGCTCCTTGGAGCTGGGGGACT |
| 84 | hTRBV14 | TGTAATACGACTCACTATAG | NNNNANNNN | GGTGCAGCCTGCAGAACTGGAG |
| 85 | hTRBV15 | TGTAATACGACTCACTATAG | NNNNANNNN | GACATCCGCTCACCAGGCCTGG |
| 86 | hTRBV16 | TGTAATACGACTCACTATAG | NNNNANNNN | TGAGATCCAGGCTACGAAGCTT |
| 87 | hTRBV17 | TGTAATACGACTCACTATAG | NNNNANNNN | GAAGATCCATCCCGCAGAGCCG |
| 88 | hTRBV18 | TGTAATACGACTCACTATAG | NNNNANNNN | GGATCCAGCAGGTAGTGCGAGG |
| 89 | hTRBV19 | TGTAATACGACTCACTATAG | NNNNANNNN | CACTGTGACATCGGCCCAAAAG |
| 90 | hTRBV20 | TGTAATACGACTCACTATAG | NNNNANNNN | CTGACAGTGACCAGTGCCCATC |
| 91 | hTRBV21 | TGTAATACGACTCACTATAG | NNNNANNNN | GAGATCCAGTCCACGGAGTCAG |
| 92 | hTRBV22 | TGTAATACGACTCACTATAG | NNNNANNNN | GTGAAGTTGGCCCACACCAGCCA |
| 93 | hTRBV23 | TGTAATACGACTCACTATAG | NNNNANNNN | CCTGGCAATCCTGTCCTCAGAA |
| 94 | hTRBV24 | TGTAATACGACTCACTATAG | NNNNANNNN | GAGTCTGCCATCCCCAACCAGA |
| 95 | hTRBV25 | TGTAATACGACTCACTATAG | NNNNANNNN | GGAGTCTGCCAGGCCCTCACA |
| 96 | hTRBV26 | TGTAATACGACTCACTATAG | NNNNANNNN | GAAGTCTGCCAGCACCAACCAG |
| 97 | hTRBV27 | TGTAATACGACTCACTATAG | NNNNANNNN | GGAGTCGCCCAGCCCCAACCAG |
| 98 | hTRBV28 | TGTAATACGACTCACTATAG | NNNNANNNN | GGAGTCCGCCAGCACCAACCAG |
| 99 | hTRBV29 | TGTAATACGACTCACTATAG | NNNNANNNN | GTGAGCAACATGAGCCCTGAAGA |
| 100 | hTRBV30 | TGTAATACGACTCACTATAG | NNNNANNNN | GAGTTCTAAGAAGCTCCTTCTCA |

TABLE 5

V segments targeted by each primer used for
the amplification of TCR β chain V segments.

| SEQ ID NO | TCR b chain V segment name | Targeted V segment(s) |
|---|---|---|
| 51 | hTRBV1 | hTRBV01 |
| 52 | hTRBV2 | hTRBV02 |
| 53 | hTRBV3-1 | hTRBV03-1, hTRBV03-2 |
| 54 | hTRBV4-1 | hTRBV04-1 |
| 55 | hTRBV4-2 | hTRBV04-2, hTRBV04-3 |
| 56 | hTRBV5-1 | hTRBV05-1 |
| 57 | hTRBV5-2 | hTRBV05-2 |
| 58 | hTRBV5-3 | hTRBV05-3 |
| 59 | hTRBV5-4 | hTRBV05-4, hTRBV05-5, hTRBV05-6, hTRBV05-7, hTRBV05-8 |
| 60 | hTRBV6-1 | hTRBV06-1 |
| 61 | hTRBV6-2 | hTRBV06-2, hTRBV06-3 |
| 62 | hTRBV6-4 | hTRBV06-4 |
| 63 | hTRBV6-5 | hTRBV06-5 |
| 64 | hTRBV6-6 | hTRBV06-6, hTRBV06-9 |
| 65 | hTRBV6-7 | hTRBV06-7 |
| 66 | hTRBV6-8 | hTRBV06-8 |
| 67 | hTRBV7-1 | hTRBV07-1 |
| 68 | hTRBV7-2 | hTRBV07-2, hTRBV07-8 |
| 69 | hTRBV7-3 | hTRBV07-3, hTRBV07-4 |
| 70 | hTRBV7-5 | hTRBV07-5 |
| 71 | hTRBV7-6 | hTRBV07-6, hTRBV07-7 |
| 72 | hTRBV7-9 | hTRBV07-9 |
| 73 | hTRBV8-1 | hTRBV08-1 |
| 74 | hTRBV8-2 | hTRBV08-2 |
| 75 | hTRBV9 | hTRBV09 |
| 76 | hTRBV10-1 | hTRBV10-1 |
| 77 | hTRBV10-2 | hTRBV10-2 |
| 78 | hTRBV10-3 | hTRBV10-3 |
| 79 | hTRBV11-1 | hTRBV11-1, hTRBV11-2, hTRBV11-3 |
| 80 | hTRBV12-1 | hTRBV12-1 |
| 81 | hTRBV12-2 | hTRBV12-2 |
| 82 | hTRBV12-3 | hTRBV12-3, hTRBV12-4, hTRBV12-5 |
| 83 | hTRBV13 | hTRBV13 |
| 84 | hTRBV14 | hTRBV14 |
| 85 | hTRBV15 | hTRBV15 |
| 86 | hTRBV16 | hTRBV16 |
| 87 | hTRBV17 | hTRBV17 |
| 88 | hTRBV18 | hTRBV18 |
| 89 | hTRBV19 | hTRBV19 |
| 90 | hTRBV20 | hTRBV20 |
| 91 | hTRBV21 | hTRBV21 |
| 92 | hTRBV22 | hTRBV22 |
| 93 | hTRBV23 | hTRBV23 |
| 94 | hTRBV24 | hTRBV24 |
| 95 | hTRBV25 | hTRBV25 |
| 96 | hTRBV26 | hTRBV26 |
| 97 | hTRBV27 | hTRBV27 |
| 98 | hTRBV28 | hTRBV28 |
| 99 | hTRBV29 | hTRBV29 |
| 100 | hTRBV30 | hTRBV30 |

TABLE 6

Primers for TCR gene amplification. Primer pair for sequencing of TCR α genes: SEQ ID NO 101 and 102. Primer pair for sequencing of TCR β genes: SEQ ID NO 101 and 103.

| SEQ ID NO | Primer name | Primer sequence | TCR chain |
|---|---|---|---|
| 101 | Forward primer T7 TRAV/TRBV | TGTAATACGACTCACTATAG | α and β |
| 102 | Reverse primer PCR 1 TRAV | GGCCACAGCACTGTTGCTCTTGAAG | α |
| 103 | Reverse primer PCR 1 TRABV | CCACTGTGCACCTCCTTCCCATTC | β |

TABLE 7

Reverse primers for TCR gene amplification that did not result in successful amplification of PCR products.

| SEQ ID NO | Primer sequence | TCR chain |
|---|---|---|
| 104 | TCGACCAGCTTGACATCACAGG | α |
| 105 | CAGATTTGTTGCTCCAGGCCACAG | α |
| 106 | TCTGTGATATACACATCAGAATC | α |
| 107 | GAATCAAAATCGGTGAATAGGCAG | α |
| 108 | GGCAGACAGACTTGTCACTGGATT | α |
| 109 | TAGGACACCGAGGTAAAGCCAC | β |
| 110 | CTGGGTGACGGGTTTGGCCCTAT | β |
| 111 | TTGACAGCGGAAGTGGTTGC | β |
| 112 | GGCTGCTCAGGCAGTATCTGGAGTC | β |
| 113 | GCCAGGCACACCAGTGTGGCCTTTT | β |

TABLE 8

Primers for addition of Next Generation Sequencing adapters. The primer portion corresponding to the Illumina ® adapters (forward and reverse) is underlined in forward and reverse primers shown below. Primer pair for sequencing of TCR α genes: SEQ ID NOS: 114 and 115. Primer pair for sequencing of TCR β genes: SEQ ID NOS: 114 and 116.

| SEQ ID NO | Primer name | Primer sequence | TCR chain |
|---|---|---|---|
| 114 | Forward primer Illumina_T7 TRAV/TRBV | AATGATACGGCGACCACCGAGATCTACACTCTTTCCCTACACGACGCT CTTCCGATCTTGTAATACGACTCACTATAG | α and β |
| 115 | Reverse primer PCR 2 TRAC | CAAGCAGAAGACGGCATACGAGATGCCTAAGTGACTGGAGTTCAGAC GTGTGCTCTTCCGATCCTCAGCTGGTACACGGCAGGGTCA | α |
| 116 | Reverse primer PCR 2 TRBC | CAAGCAGAAGACGGCATACGAGATGCCTAAGTGACTGGAGTTCAGAC GTGTGCTCTTCCGATCAAACACAGCGACCTCGGGTGGGAAC | β |

Example 2: Exemplary Protocol for the SEQTR Method Using Nextera Adapters

TCR α and β chain genes were sequenced in two independent reactions.

1) Starting material and RNA extraction
   To obtain sufficient amounts of RNA in the extraction, a minimum of 500,000 T-cells were used as starting material. Alternatively, and especially in instances where fewer T-cells were available, T-cells were mixed with 50,000 mouse 3T3 cells that served as carrier. T-cell RNA was extracted using the RNeasy® Micro Kit from Qiagen Inc. according to the manufacturer's instruction with the following modification: Elution was performed with 20 µl of water preheated to 50° C. RNA quality and quantity was verified using a fragment analyzer.

2) cRNA synthesis by in vitro transcription (IVT):
   In vitro transcription of isolated RNA was performed using the MessageAmp™ II aRNA Amplification Kit from Ambion® (Thermo Fisher Scientific), which contains enzymes, buffers and nucleotides required to perform the first and second strand cDNA and the in vitro transcription. The kit also provides all columns and reagents needed for the cDNA and cRNA purifications. RNA amplification was performed according to the manufacturer's instructions with the following modifications: 1) Between 0.5 and 1 µg of total RNA as was used as starting material. 2) The IVT was performed in a final volume of 40 µl, and incubated at 37° C. for 16 h. Purified cRNA was quantified by absorbance using a NanoDrop™ spectrophotometer (Thermo Fisher Scientific).

3) cDNA synthesis by reverse transcription:
   The reverse transcription of the cRNA was performed with the SuperScript® III from Invitrogen (Thermo Fisher Scientific). The kit provides the enzyme, the buffer and the dithiothreitol (DTT) needed for the reaction. Deoxynucleotides (dNTPs) and RNAsin® Ribonuclease inhibitor were purchased from Promega. The sequences for the primers used for the reverse transcription can be found in Table 9 (primers for sequencing TCR α chain genes) and Table 10 (primers for sequencing TCR β chain genes).

500 ng of cRNA were used as starting material for the reverse transcription. cRNA was mixed with 1 µl hTRAV or hTRBV primers mix (2 µM each) and 1 µl dNTP (25 mM) in a final volume of 13 µl. The mix was first incubated at 70° C. for 10 min, then at 50° C. for 30 s. 4 µl 5× buffer, 1 µl DTT (100 mM), 1 µl SuperScript III and 1 µl RNAsin® were added to the mix. The samples were subsequently incubated for at 55° C. 1 h and then at 85° C. for 5 min. After the cDNA synthesis, 1 µg DNase-free RNase (Roche) was added to the cDNA and incubated at 37° C. for 30 min to remove the cRNA.

4) TCR gene amplification:
  TCR gene amplification was performed using a Phusion® High-Fidelity DNA polymerase (New England Biolabs) under the following conditions:
  PCR mix: 1 μl cDNA from step 3, 0.4 μl dNTPs (10 mM), 0.4 μl primer mix (20 μM Nextera5', 10 μM Reverse primer PCR 1 TRAV or 2.5 μM Reverse primer PCR1 TRBV, see Table 11), 2 μl 5× buffer and 0.2 μl Phusion® enzyme in a total volume of 10 μl.
  PCR conditions:
    94° C. for 5 min
    20 cycles of
      98° C. for 10 s
      55° C. for 30 s
      72° C. for 30 s
    72° C. for 2 min
  PCR products were purified using 1 μl of ExoSAP-IT® PCR Product Cleanup Kit (Affymetrix) according to the manufacturer's instructions.

5) Addition of Next Generation Sequencing adapters:
  ILLUMINA® sequencing adapters were added by PCR using a Phusion® High-Fidelity DNA polymerase (New England Biolabs). The following mix was added to the 11 μl of PCR1: 1 μl dNTPs (10 mM), 1 μl primer mix (1.25 μM each, see Table 12), 3 μl 5× buffer and 0.2 μl Phusion® enzyme and 9.8 μl of H$_2$O.
  PCR conditions:
    94° C. for 5 min
    perform 25 cycles of:
      98° C. for 10 s
      55° C. for 30 s
      72° C. for 30 s
    72° C. for 2 min 6) TCR library purification:
  10 μl of the PCR product from step 5 were purified using an AMPURE XP beads (Beckman Coulter) according to the manufacturer's instruction. Samples could then directly be used for ILLUMINA® sequencing.

TABLE 9

Preferred primer sequences for amplification of TCR α chain V segments. N can be any nucleotide. The sequences for primers presented in this table consist of three parts (listed from 5' to 3'): T7 adapter, barcode and TCR α chain V segment.

| SEQ ID NO | Primer name | Sequence Nextera adapter portion of the primer | Sequence barcode portion of the primer | Sequence TCR α chain V segment portion of the primer |
|---|---|---|---|---|
| 261 | hTRAV1-1 | TCGTCGGCAGCGTCAGATGTGTATAAGAGACAG | HHHHHNNNN | CTTCTACAGGAGCTCCAGATGAAAG |
| 262 | hTRAV1-2 | TCGTCGGCAGCGTCAGATGTGTATAAGAGACAG | HHHHHNNNN | CTTTTGAAGGAGCTCCAGATGAAAG |
| 263 | hTRAV2 | TCGTCGGCAGCGTCAGATGTGTATAAGAGACAG | HHHHHNNNN | TGCTCATCCTCCAGGTGCGGGA |
| 264 | hTRAV3 | TCGTCGGCAGCGTCAGATGTGTATAAGAGACAG | HHHHHNNNN | GAAGAAACCATCTGCCCTTGTGA |
| 265 | hTRAV4 | TCGTCGGCAGCGTCAGATGTGTATAAGAGACAG | HHHHHNNNN | CCTGCCCCGGGTTTCCCTGAGCGAC |
| 266 | hTRAV5 | TCGTCGGCAGCGTCAGATGTGTATAAGAGACAG | HHHHHNNNN | TCTCTGCGCATTGCAGACACCCA |
| 267 | hTRAV6 | TCGTCGGCAGCGTCAGATGTGTATAAGAGACAG | HHHHHNNNN | TTGTTTCATATCACAGCCTCCCA |
| 268 | hTRAV7 | TCGTCGGCAGCGTCAGATGTGTATAAGAGACAG | HHHHHNNNN | GCTTGTACATTACAGCCGTGCA |
| 269 | hTRAV8-1/8-3 | TCGTCGGCAGCGTCAGATGTGTATAAGAGACAG | HHHHHNNNN | ATCTGAGGAAACCCTCTGTGCA |
| 270 | hTRAV8-2/8-4 | TCGTCGGCAGCGTCAGATGTGTATAAGAGACAG | HHHHHNNNN | ACCTGACGAAACCCTCAGCCCAT |
| 271 | hTRAV8-5 | TCGTCGGCAGCGTCAGATGTGTATAAGAGACAG | HHHHHNNNN | CCTATGCCTGTCTTTACTTTAATC |
| 272 | hTRAV8-6 | TCGTCGGCAGCGTCAGATGTGTATAAGAGACAG | HHHHHNNNN | CTTGAGGAAACCCTCAGTCCATAT |
| 273 | hTRAV8-7 | TCGTCGGCAGCGTCAGATGTGTATAAGAGACAG | HHHHHNNNN | GAAACCATCAACCCATGTGAGTGA |
| 274 | hTRAV9-1 | TCGTCGGCAGCGTCAGATGTGTATAAGAGACAG | HHHHHNNNN | ACTTGGAGAAAGACTCAGTTCAA |
| 275 | hTRAV9-2 | TCGTCGGCAGCGTCAGATGTGTATAAGAGACAG | HHHHHNNNN | ACTTGGAGAAAGGCTCAGTTCAA |

TABLE 9-continued

Preferred primer sequences for amplification of TCR α chain V segments. N can be any nucleotide. The sequences for primers presented in this table consist of three parts (listed from 5' to 3'): T7 adapter, barcode and TCR α chain V segment.

| SEQ ID NO | Primer name | Sequence Nextera adapter portion of the primer | Sequence barcode portion of the primer | Sequence TCR α chain V segment portion of the primer |
|---|---|---|---|---|
| 276 | hTRAV10 | TCGTCGGCAGCGTCAGATGTGTATAAGAGACAG | HHHHHNNNN | CTGCACATCACAGCCTCCCA |
| 277 | hTRAV11 | TCGTCGGCAGCGTCAGATGTGTATAAGAGACAG | HHHHHNNNN | GTTTGGAATATCGCAGCCTCTCAT |
| 278 | hTRAV12-1 | TCGTCGGCAGCGTCAGATGTGTATAAGAGACAG | HHHHHNNNN | CCCTGCTCATCAGAGACTCCAAG |
| 279 | hTRAV12-2 | TCGTCGGCAGCGTCAGATGTGTATAAGAGACAG | HHHHHNNNN | CTCTGCTCATCAGAGACTCCCAG |
| 280 | hTRAV12-3 | TCGTCGGCAGCGTCAGATGTGTATAAGAGACAG | HHHHHNNNN | CCTTGTTCATCAGAGACTCACAG |
| 281 | hTRAV13-1 | TCGTCGGCAGCGTCAGATGTGTATAAGAGACAG | HHHHHNNNN | TCCCTGCACATCACAGAGACCCAA |
| 282 | hTRAV13-2 | TCGTCGGCAGCGTCAGATGTGTATAAGAGACAG | HHHHHNNNN | TCTCTGCAAATTGCAGCTACTCAA |
| 283 | hTRAV14 | TCGTCGGCAGCGTCAGATGTGTATAAGAGACAG | HHHHHNNNN | TTGTCATCTCCGCTTCACAACTGG |
| 284 | hTRAV15 | TCGTCGGCAGCGTCAGATGTGTATAAGAGACAG | HHHHHNNNN | GTTTTGAATATGCTGGTCTCTCAT |
| 285 | hTRAV16 | TCGTCGGCAGCGTCAGATGTGTATAAGAGACAG | HHHHHNNNN | CCTGAAGAAACCATTTGCTCAAGA |
| 286 | hTRAV17 | TCGTCGGCAGCGTCAGATGTGTATAAGAGACAG | HHHHHNNNN | TCCTTGTTGATCACGGCTTCCCGG |
| 287 | hTRAV18 | TCGTCGGCAGCGTCAGATGTGTATAAGAGACAG | HHHHHNNNN | ACCTGGAGAAGCCCTCGGTGCA |
| 288 | hTRAV19 | TCGTCGGCAGCGTCAGATGTGTATAAGAGACAG | HHHHHNNNN | CACCATCACAGCCTCACAAGTCGT |
| 289 | hTRAV20 | TCGTCGGCAGCGTCAGATGTGTATAAGAGACAG | HHHHHNNNN | TTTCTGCACATCACAGCCCCTA |
| 290 | hTRAV21 | TCGTCGGCAGCGTCAGATGTGTATAAGAGACAG | HHHHHNNNN | CTTTATACATTGCAGCTTCTCAGCC |
| 291 | hTRAV22 | TCGTCGGCAGCGTCAGATGTGTATAAGAGACAG | HHHHHNNNN | GTACATTTCCTCTTCCCAGACCAC |
| 292 | hTRAV23 | TCGTCGGCAGCGTCAGATGTGTATAAGAGACAG | HHHHHNNNN | CATTGCATATCATGGATTCCCAGC |
| 293 | hTRAV24 | TCGTCGGCAGCGTCAGATGTGTATAAGAGACAG | HHHHHNNNN | GCTATTTGTACATCAAAGGATCCC |
| 294 | hTRAV25 | TCGTCGGCAGCGTCAGATGTGTATAAGAGACAG | HHHHHNNNN | CAGCTCCCTGCACATCACAGCCA |
| 295 | hTRAV26-1 | TCGTCGGCAGCGTCAGATGTGTATAAGAGACAG | HHHHHNNNN | TTGATCCTGCCCCACGCTACGCTGA |
| 296 | hTRAV26-2 | TCGTCGGCAGCGTCAGATGTGTATAAGAGACAG | HHHHHNNNN | TTGATCCTGCACCGTGCTACCTTGA |
| 297 | hTRAV27 | TCGTCGGCAGCGTCAGATGTGTATAAGAGACAG | HHHHHNNNN | GTTCTCTCCACATCACTGCAGCC |
| 298 | hTRAV28 | TCGTCGGCAGCGTCAGATGTGTATAAGAGACAG | HHHHHNNNN | GCCACCTATACATCAGATTCCCA |
| 299 | hTRAV29 | TCGTCGGCAGCGTCAGATGTGTATAAGAGACAG | HHHHHNNNN | TCTCTGCACATTGTGCCCTCCCA |

TABLE 9-continued

Preferred primer sequences for amplification of TCR α chain V segments. N can be any nucleotide. The sequences for primers presented in this table consist of three parts (listed from 5' to 3'): T7 adapter, barcode and TCR α chain V segment.

| SEQ ID NO | Primer name | Sequence Nextera adapter portion of the primer | Sequence barcode portion of the primer | Sequence TCR α chain V segment portion of the primer |
|---|---|---|---|---|
| 300 | hTRAV30 | TCGTCGGCAGCGTCAGATGTGTATAAGAGACAG | HHHHHNNNN | CCCTGTACCTTACGGCCTCCCAGCT |
| 301 | hTRAV31 | TCGTCGGCAGCGTCAGATGTGTATAAGAGACAG | HHHHHNNNN | CTTATCATATCATCATCACAGCCA |
| 302 | hTRAV32 | TCGTCGGCAGCGTCAGATGTGTATAAGAGACAG | HHHHHNNNN | TCCCTGCATATTACAGCCACCCAA |
| 303 | hTRAV33 | TCGTCGGCAGCGTCAGATGTGTATAAGAGACAG | HHHHHNNNN | ACCTCACCATCAATTCCTTAAAAC |
| 304 | hTRAV34 | TCGTCGGCAGCGTCAGATGTGTATAAGAGACAG | HHHHHNNNN | TCCCTGCATATCACAGCCTCCCAG |
| 305 | hTRAV35 | TCGTCGGCAGCGTCAGATGTGTATAAGAGACAG | HHHHHNNNN | CTTCCTGAATATCTCAGCATCCAT |
| 306 | hTRAV36 | TCGTCGGCAGCGTCAGATGTGTATAAGAGACAG | HHHHHNNNN | TCCTGAACATCACAGCCACCCAG |
| 307 | hTRAV37 | TCGTCGGCAGCGTCAGATGTGTATAAGAGACAG | HHHHHNNNN | TCCCTGCACATACAGGATTCCCAG |
| 308 | hTRAV38 | TCGTCGGCAGCGTCAGATGTGTATAAGAGACAG | HHHHHNNNN | CAAGATCTCAGACTCACAGCTGG |
| 309 | hTRAV39 | TCGTCGGCAGCGTCAGATGTGTATAAGAGACAG | HHHHHNNNN | CCGTCTCAGCACCCTCCACATCA |
| 310 | hTRAV40 | TCGTCGGCAGCGTCAGATGTGTATAAGAGACAG | HHHHHNNNN | CCATTGTGAAATATTCAGTCCAGG |

TABLE 10

Preferred primer sequences for amplification of TCR β chain V segments. N can be any nucleotide. The sequences for primers presented in this table consist of three parts (listed from 5' to 3'): T7 adapter, barcode and TCR β chain V segment.

| SEQ ID NO | Primer name | Sequence T7 adapter portion of the primer | Sequence barcode portion of the primer | Sequence TCR β chain V segment portion of the primer |
|---|---|---|---|---|
| 311 | hTRBV1 | TCGTCGGCAGCGTCAGATGTGTATAAGAGACAG | HHHHHNNNN | GTGGTCGCACTGCAGCAAGAAGA |
| 312 | hTRBV2 | TCGTCGGCAGCGTCAGATGTGTATAAGAGACAG | HHHHHNNNN | GATCCGGTCCACAAAGCTGGAGGA |
| 313 | hTRBV3-1 | TCGTCGGCAGCGTCAGATGTGTATAAGAGACAG | HHHHHNNNN | CATCAATTCCCTGGAGCTTGGTGA |
| 314 | hTRBV4-1 | TCGTCGGCAGCGTCAGATGTGTATAAGAGACAG | HHHHHNNNN | TTCACCTACACGCCCTGCAGCCAG |
| 315 | hTRBV4-2 | TCGTCGGCAGCGTCAGATGTGTATAAGAGACAG | HHHHHNNNN | TTCACCTACACACCCTGCAGCCAG |
| 316 | hTRBV5-1 | TCGTCGGCAGCGTCAGATGTGTATAAGAGACAG | HHHHHNNNN | GAATGTGAGCACCTTGGAGCTGG |
| 317 | hTRBV5-2 | TCGTCGGCAGCGTCAGATGTGTATAAGAGACAG | HHHHHNNNN | TACTGAGTCAAACACGGAGCTAGG |
| 318 | hTRBV5-3 | TCGTCGGCAGCGTCAGATGTGTATAAGAGACAG | HHHHHNNNN | GCTCTGAGATGAATGTGAGTGCCT |

TABLE 10-continued

Preferred primer sequences for amplification of TCR β chain V segments. N can be any nucleotide. The sequences for primers presented in this table consist of three parts (listed from 5' to 3'): T7 adapter, barcode and TCR β chain V segment.

| SEQ ID NO | Primer name | Sequence T7 adapter portion of the primer | Sequence barcode portion of the primer | Sequence TCR β chain V segment portion of the primer |
|---|---|---|---|---|
| 319 | hTRBV5-4 | TCGTCGGCAGCGTCAGATGTGTATAAGAGACAG | HHHHHNNNN | CTGAGCTGAATGTGAACGCCTT |
| 320 | hTRBV6-1 | TCGTCGGCAGCGTCAGATGTGTATAAGAGACAG | HHHHHNNNN | GAGTTCTCGCTCAGGCTGGAGT |
| 321 | hTRBV6-2 | TCGTCGGCAGCGTCAGATGTGTATAAGAGACAG | HHHHHNNNN | CTGGGGTTGGAGTCGGCTGCTC |
| 322 | hTRBV6-4 | TCGTCGGCAGCGTCAGATGTGTATAAGAGACAG | HHHHHNNNN | CCCCTCACGTTGGCGTCTGCTG |
| 323 | hTRBV6-5 | TCGTCGGCAGCGTCAGATGTGTATAAGAGACAG | HHHHHNNNN | TCCCGCTCAGGCTGCTGTCGGC |
| 324 | hTRBV6-6 | TCGTCGGCAGCGTCAGATGTGTATAAGAGACAG | HHHHHNNNN | GATTTCCCGCTCAGGCTGGAGT |
| 325 | hTRBV6-7 | TCGTCGGCAGCGTCAGATGTGTATAAGAGACAG | HHHHHNNNN | TCCCCCTCAAGCTGGAGTCAGCT |
| 326 | hTRBV6-8 | TCGTCGGCAGCGTCAGATGTGTATAAGAGACAG | HHHHHNNNN | TCCCACTCAGGCTGGTGTCGGC |
| 327 | hTRBV7-1 | TCGTCGGCAGCGTCAGATGTGTATAAGAGACAG | HHHHHNNNN | CTCTGAAGTTCCAGCGCACACA |
| 328 | hTRBV7-2 | TCGTCGGCAGCGTCAGATGTGTATAAGAGACAG | HHHHHNNNN | GATCCAGCGCACACAGCAGGAG |
| 329 | hTRBV7-3 | TCGTCGGCAGCGTCAGATGTGTATAAGAGACAG | HHHHHNNNN | ACTCTGAAGATCCAGCGCACAGA |
| 330 | hTRBV7-5 | TCGTCGGCAGCGTCAGATGTGTATAAGAGACAG | HHHHHNNNN | AGATCCAGCGCACAGAGCAAGG |
| 331 | hTRBV7-6 | TCGTCGGCAGCGTCAGATGTGTATAAGAGACAG | HHHHHNNNN | CAGCGCACAGAGCAGCGGGACT |
| 332 | hTRBV7-9 | TCGTCGGCAGCGTCAGATGTGTATAAGAGACAG | HHHHHNNNN | GAGATCCAGCGCACAGAGCAGG |
| 333 | hTRBV8-1 | TCGTCGGCAGCGTCAGATGTGTATAAGAGACAG | HHHHHNNNN | CCCTCAACCCTGGAGTCTACTA |
| 334 | hTRBV8-2 | TCGTCGGCAGCGTCAGATGTGTATAAGAGACAG | HHHHHNNNN | TCCCCAATCCTGGCATCCACCA |
| 335 | hTRBV9 | TCGTCGGCAGCGTCAGATGTGTATAAGAGACAG | HHHHHNNNN | CTAAACCTGAGCTCTCTGGAGCT |
| 336 | hTRBV10-1 | TCGTCGGCAGCGTCAGATGTGTATAAGAGACAG | HHHHHNNNN | CCCTCACTCTGGAGTCTGCTGC |
| 337 | hTRBV10-2 | TCGTCGGCAGCGTCAGATGTGTATAAGAGACAG | HHHHHNNNN | CCCTCACTCTGGAGTCAGCTAC |
| 338 | hTRBV10-3 | TCGTCGGCAGCGTCAGATGTGTATAAGAGACAG | HHHHHNNNN | TCCTCACTCTGGAGTCCGCTAC |
| 339 | hTRBV11-1 | TCGTCGGCAGCGTCAGATGTGTATAAGAGACAG | HHHHHNNNN | CCACTCTCAAGATCCAGCCTGCA |
| 340 | hTRBV12-1 | TCGTCGGCAGCGTCAGATGTGTATAAGAGACAG | HHHHHNNNN | GAGGATCCAGCCCATGGAACCCA |
| 341 | hTRBV12-2 | TCGTCGGCAGCGTCAGATGTGTATAAGAGACAG | HHHHHNNNN | CTGAAGATCCAGCCTGCAGAGC |
| 342 | hTRBV12-3 | TCGTCGGCAGCGTCAGATGTGTATAAGAGACAG | HHHHHNNNN | CAGCCCTCAGAACCCAGGGACT |

TABLE 10-continued

Preferred primer sequences for amplification of TCR β chain V segments. N can be any nucleotide. The sequences for primers presented in this table consist of three parts (listed from 5' to 3'): T7 adapter, barcode and TCR β chain V segment.

| SEQ ID NO | Primer name | Sequence T7 adapter portion of the primer | Sequence barcode portion of the primer | Sequence TCR β chain V segment portion of the primer |
| --- | --- | --- | --- | --- |
| 343 | hTRBV13 | TCGTCGGCAGCGTCAGATGTGTATAAGAGACAG | HHHHHNNNN | GAGCTCCTTGGAGCTGGGGGACT |
| 344 | hTRBV14 | TCGTCGGCAGCGTCAGATGTGTATAAGAGACAG | HHHHHNNNN | GGTGCAGCCTGCAGAACTGGAG |
| 345 | hTRBV15 | TCGTCGGCAGCGTCAGATGTGTATAAGAGACAG | HHHHHNNNN | GACATCCGCTCACCAGGCCTGG |
| 346 | hTRBV16 | TCGTCGGCAGCGTCAGATGTGTATAAGAGACAG | HHHHHNNNN | TGAGATCCAGGCTACGAAGCTT |
| 347 | hTRBV17 | TCGTCGGCAGCGTCAGATGTGTATAAGAGACAG | HHHHHNNNN | GAAGATCCATCCCGCAGAGCCG |
| 348 | hTRBV18 | TCGTCGGCAGCGTCAGATGTGTATAAGAGACAG | HHHHHNNNN | GGATCCAGCAGGTAGTGCGAGG |
| 349 | hTRBV19 | TCGTCGGCAGCGTCAGATGTGTATAAGAGACAG | HHHHHNNNN | CACTGTGACATCGGCCCAAAAG |
| 350 | hTRBV20 | TCGTCGGCAGCGTCAGATGTGTATAAGAGACAG | HHHHHNNNN | CTGACAGTGACCAGTGCCCATC |
| 351 | hTRBV21 | TCGTCGGCAGCGTCAGATGTGTATAAGAGACAG | HHHHHNNNN | GAGATCCAGTCCACGGAGTCAG |
| 352 | hTRBV22 | TCGTCGGCAGCGTCAGATGTGTATAAGAGACAG | HHHHHNNNN | GTGAAGTTGGCCCACACCAGCCA |
| 353 | hTRBV23 | TCGTCGGCAGCGTCAGATGTGTATAAGAGACAG | HHHHHNNNN | CCTGGCAATCCTGTCCTCAGAA |
| 354 | hTRBV24 | TCGTCGGCAGCGTCAGATGTGTATAAGAGACAG | HHHHHNNNN | GAGTCTGCCATCCCCAACCAGA |
| 355 | hTRBV25 | TCGTCGGCAGCGTCAGATGTGTATAAGAGACAG | HHHHHNNNN | GGAGTCTGCCAGGCCCTCACA |
| 356 | hTRBV26 | TCGTCGGCAGCGTCAGATGTGTATAAGAGACAG | HHHHHNNNN | GAAGTCTGCCAGCACCAACCAG |
| 357 | hTRBV27 | TCGTCGGCAGCGTCAGATGTGTATAAGAGACAG | HHHHHNNNN | GGAGTCGCCCAGCCCCAACCAG |
| 358 | hTRBV28 | TCGTCGGCAGCGTCAGATGTGTATAAGAGACAG | HHHHHNNNN | GGAGTCCGCCAGCACCAACCAG |
| 359 | hTRBV29 | TCGTCGGCAGCGTCAGATGTGTATAAGAGACAG | HHHHHNNNN | GTGAGCAACATGAGCCCTGAAGA |
| 360 | hTRBV30 | TCGTCGGCAGCGTCAGATGTGTATAAGAGACAG | HHHHHNNNN | GAGTTCTAAGAAGCTCCTTCTCA |

TABLE 11

Primers for TCR gene amplification. Primer pair for sequencing of TCR α genes: SEQ ID NOs: 256 and 257. Primer pair for sequencing of TCR β genes: SEQ ID NOs: 256 and 258. The primer portion corresponding to the Illumina ® adapters (forward and reverse) is underlined in reverse primers shown below.

| SEQ ID NO | Primer name | Primer sequence | TCR chain |
|---|---|---|---|
| 256 | Forward primer Nextera 5' | TCGTCGGCAGCGTC | α and β |
| 257 | Reverse primer PCR 1 TRAV | <u>GTCTCGTGGGCTCGGAGATGTGTATAA GAGACAG</u>GAATCAAAATCGGTGAATA GGCAG | α |
| 258 | Reverse primer PCR 1 TRBV | <u>GTCTCGTGGGCTCGGAGATGTGTATAA GAGACAG</u>GCCAGGCACACCAGTGTGG CCTTTT | β |

TABLE 12

Primers used to add the full Nextera sequence to both TCRα and TCRβ.

| SEQ ID NO | Primer name | Primer sequence | TCR chain |
|---|---|---|---|
| 259 | Index Read 1 | CAAGCAGAAGACGGCATACGAGAT[i7]GTCTCGTGGGCTC | α and β |
| 260 | Index Read 2 | AATGATACGGCGACCACCGAGATCTACAC[i5]TCGTCGGCAGCG | α |

Example 3: Exemplary Protocol for the SEQTR Method without In Vitro Transcription TCR α and β chain genes were sequenced in two independent reactions.

1) Starting material and RNA extraction
   To obtain sufficient amounts of RNA in the extraction, a minimum of 500,000 T-cells were used as starting material. Alternatively, and especially in instances where fewer T-cells were available, T-cells were mixed with 50,000 mouse 3T3 cells that served as carrier. T-cell RNA was extracted using the RNeasy® Micro Kit from Qiagen Inc. according the manufacturer's instruction with the following modification: Elution was performed with 20 μl of water preheated to 50° C. RNA quality and quantity was verified using a fragment analyzer.

2) cDNA synthesis by reverse transcription:
   The reverse transcription of the RNA was performed with the SuperScript® III from Invitrogen (Thermo Fisher Scientific) and oligo d(T). The kit provides the enzyme, the buffer and the dithiothreitol (DTT) needed for the reaction. Deoxynucleotides (dNTPs), oligo d(T) and RNAsin® Ribonuclease inhibitor were purchased from Promega. 500 ng of RNA were used as starting material for the reverse transcription. RNA was mixed with 1 μl of oligo d(T) and 1 μl dNTP (25 mM) in a final volume of 13 μl. The mix was first incubated at 70° C. for 10 min, then at 50° C. for 30 s. 4 μl 5× buffer, 1 μl DTT (100 mM), 1 μl SuperScript III and 1 μl RNAsin® were added to the mix. The samples were subsequently incubated for at 55° C. 1 h and then at 85° C. for 5 min.

3) Second strand cDNA synthesis:
   cDNA was then used to synthesize the second strand, performed using the Phusion® High-Fidelity DNA polymerase (New England Biolabs) under the following conditions:
   Mix: 20 μl cDNA from step 2, 4 μl dNTPs (10 mM), 2 μl TRAV primer mix (Table 9), 2 μl TRBV primers mix (Table 10), 20 μl 5× buffer, 1 μl Phusion® enzyme in a total volume of 100 μl.
   Synthesis conditions:
   98° C. for 5 min
   40° C. for 30 s
   72° C. for 5 min 4) cDNA purification:
   100 μl of the cDNA product from step 3 were purified using an AMPURE XP beads (Beckman Coulter) according to the manufacturer's instruction.

5) TCR gene amplification:
   TCR gene amplification was performed using a Phusion® High-Fidelity DNA polymerase (New England Biolabs) under the following conditions:
   PCR mix: 7 μl cDNA from step 4, 0.4 μl dNTPs (10 mM), 0.4 μl primer mix (20 μM Nextera5', 10 μM Reverse primer PCR 1 TRAV or 2.5 μM Reverse primer PCR1 TRBV, see Table 11), 2 μl 5× buffer and 0.2 μl Phusion® enzyme in a total volume of 10 μl.
   PCR conditions:
   94° C. for 5 min
   20 cycles of
   98° C. for 10 s
   55° C. for 30 s
   72° C. for 30 s
   72° C. for 2 min PCR products were purified using 1 µl of ExoSAP-IT® PCR Product Cleanup Kit (Affymetrix) according to the manufacturer's instructions.

6) Addition of Next Generation Sequencing adapters:
ILLUMINA® sequencing adapters were added by PCR using a Phusion® High-Fidelity DNA polymerase (New England Biolabs). The following mix was added to the 11 µl of PCR1: 1 µl dNTPs (10 mM), 1 µl primer mix (1.25 µM each, see Table 12), 3 µl 5× buffer and 0.2 µl Phusion® enzyme and 9.8 µl of $H_2O$.

PCR conditions:
94° C. for 5 min
perform 25 cycles of:
98° C. for 10 s
55° C. for 30 s
72° C. for 30 s
72° C. for 2 min 7) TCR library purification:
10 µl of the PCR product from step 5 were purified using an AMPURE XP beads (Beckman Coulter) according to the manufacturer's instruction. Samples could then directly be used for ILLUMINA® sequencing.

Example 4: Sensitivity of the TCR Sequencing Method

One of the challenges of TCR sequencing are the small amounts of genetic material for each T-cell clone. In many cases, the number of T-cells that can be recovered from a given experiment is too small for researchers to directly extract sufficient amounts of RNA for a subsequent amplification of the TCR genes. In such instances, the T-cells of interest can be mixed with 3T3 mouse cells, which serve as a carrier.

$5 \times 10^4$ 3T3 cells were mixed with $10^6$, $10^5$, $10^4$, $10^3$ or 0 CD8 positive T-cells, respectively. The RNA of each mixture was isolated and subjected to steps 2 to 4 of the SEQTR method outlined above (see Detailed Description of the Invention). PCR products were separated on an agarose gel and visualized.

Figure 4:
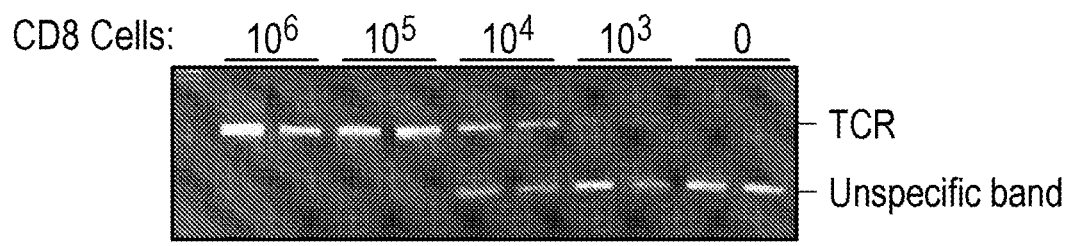
FIG. 4 illustrates the sensitivity of the SEQTR method. $10^{\wedge}6$, $10^{\wedge}5$, $10^{\wedge}4$, $10^{\wedge}3$ or 0 CD8 positive T-cells, respectively, were mixed with $5 \times 10^{\wedge}4$ 3T3 cells. The RNA was extracted and subjected to transcription, reverse transcription and one round of amplification (steps 2-4, see Detailed Description). The resulting PCR products were separated on an agarose gels and visualized with ethidium bromide.
Figure 5:
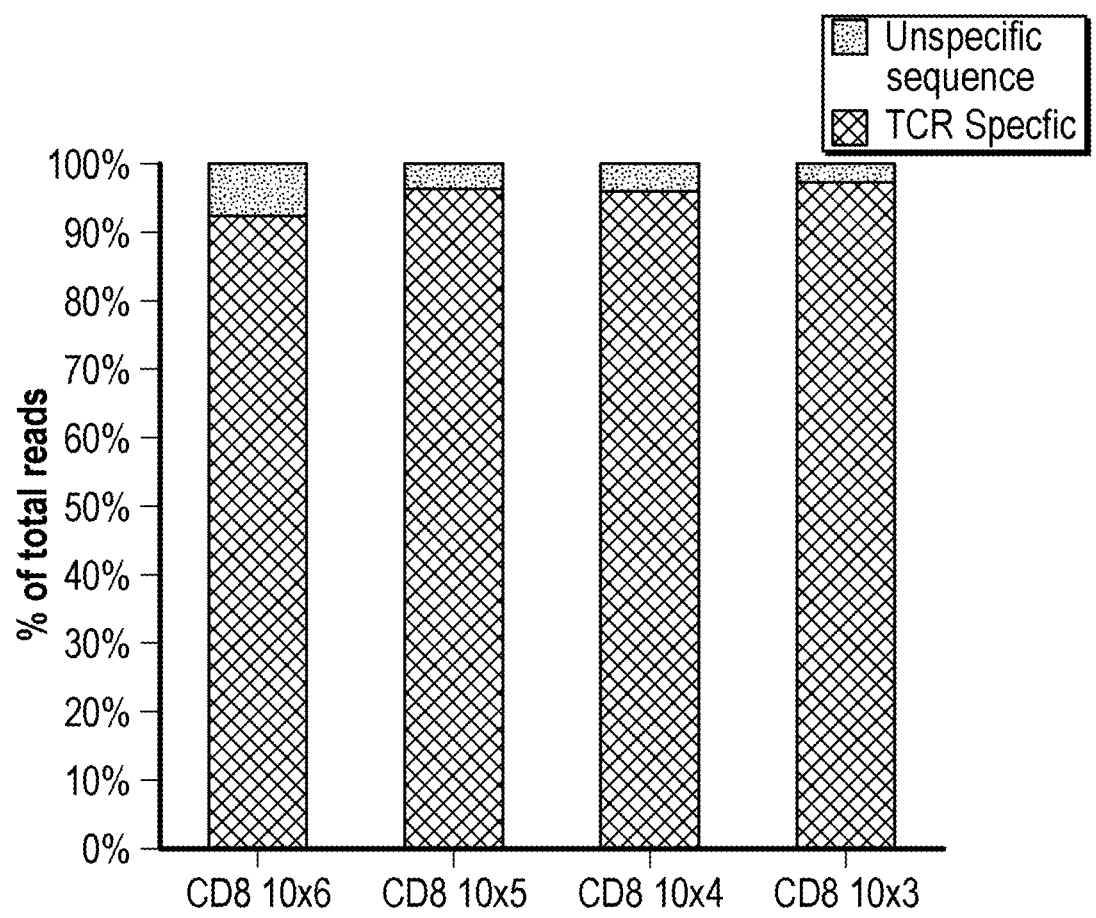
FIG. 5 illustrates the specificity of the SEQTR method. $10^{\wedge}6$, $10^{\wedge}5$, $10^{\wedge}4$, $10^{\wedge}3$ or 0 CD8 positive T-cells, respectively, were mixed with $5 \times 10^{\wedge}4$ 3T3 cells. The RNA was extracted and subjected to the SEQTR method. The percentages of sequencing reads that were or were not, respectively, associated with actual TCR genes are indicated.

No TCR-specific PCR products were observed in samples that only contained 3T3 cells (see FIG. 4). However, TCR-specific bands were detected in all other samples: Increasing amounts of CD8 positive T-cells in the samples were correlated with increasing amounts of TCR-specific PCR products and decreasing intensity of the unspecific dimer primer band. These data demonstrate that the SEQTR method is sensitive enough to amplify TCR genes from as little as 1,000 T-cells, with no detectable background signal from the 3T3 carrier cells.

Example 5: Specificity of the SEQTR Method

Another challenge of TCR sequencing is the lack of specific amplification of TCR genes from complex samples. Competing TCR sequencing technologies such as services offered by Adaptive Biotechnology are characterized by up to 90% unspecific amplification. As a result, only as little as 10% of all sequencing data are informative for TCR repertoire determination, increasing cost and duration of any project aiming to sequence TCR repertoires.

$5 \times 10^4$ 3T3 cells were mixed with $10^6$, $10^5$, $10^4$, $10^3$ or 0 CD8 positive T-cells, respectively. TCR repertoires for the individual samples were sequenced using the SEQTR method, and the percentage of reads that corresponded to TCR or non-TCR sequences, respectively, was determined. As shown in FIG. 5, 93-97% of all sequencing reads indeed corresponded to TCR genes, independent of the amount of T-cells used as starting material. In summary, these data show that TCR amplification using the SEQTR method is highly specific even when as little as 1,000 T-cells are used as starting material.

Example 6: Unambiguous Identification of TCR Genes

In humans, the TCR locus comprises 54 different V segments for the TCR α chain and 65 different V segments for the TCR β chain. However, many of these V segments are highly homologous. Consequently, one of the big challenges of TCR sequencing is to successfully differentiate between two or more TCR gene segments with high degrees of homology. For instance, depending on the choice of primer used in the amplification of the TCR gene and the length of the generated PCR product, the resulting sequencing data might be compatible with more than one V or J segment (in other words, two or more TCR V or J segments show 100% homology in the sequenced region). In these cases, the TCR gene for a specific read cannot be unambiguously assigned/identified.

Figure 6:
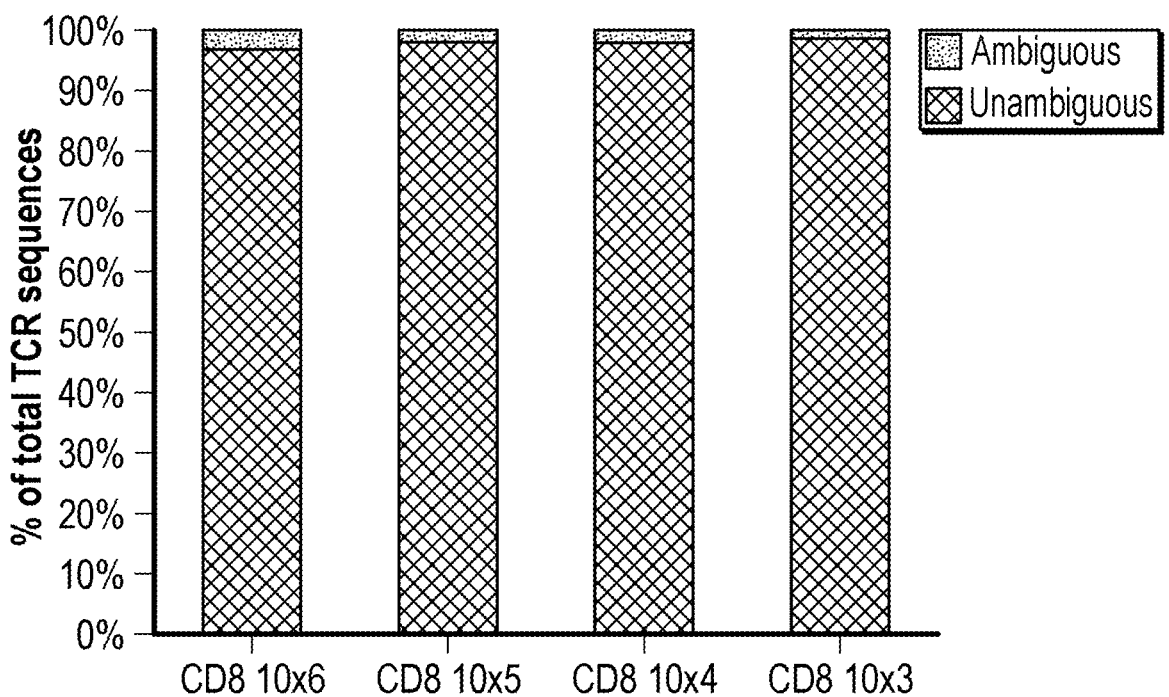
FIG. 6 illustrates the unambiguous identification of TCR genes as a feature of the SEQTR method. $5 \times 10^{\wedge}4$ 3T3 cells were mixed with $10^{\wedge}6$, $10^{\wedge}5$, $10^{\wedge}4$, $10^{\wedge}3$ or 0 CD8 positive T-cells, respectively. The RNA of each mixture was isolated and subjected to the SEQTR method. Reads that were not associated with TCR genes were removed from the data set. For the remaining reads, the percentages of reads that could or could not, respectively, be unambiguously assigned to specific V or J segments are indicated.

$5 \times 10^4$ 3T3 cells were mixed with $10^6$, $10^5$, $10^4$, $10^3$ or 0 CD8 positive T-cells, respectively. The RNA of each mixture was isolated and subjected to the TCR sequencing method. Out of all the sequencing reads that were identified as TCR genes, it was assessed if the V or J segments could be identified unambiguously. The data show that between 95% and 97% of all TCR sequencing reads could be assigned to a specific TCR segment, even when using as little as 1,000 T-cells as genetic starting material (see FIG. 6). In summary, the data demonstrate the robustness of the SEQTR method as 90 to 93% of all reads can be used to identify TCR sequences once unspecific sequences and ambiguous TCR sequences have been removed.

Due to the homology between V segments, it can be sometimes difficult to clearly identify the TCR sequence. hTRBV6-2 and hTRBV6-3 cannot be differentiated as they have 100% homology and thus will code for the same TCR. Due to their sequences, hTRBV12-3 and hTRBV12-4 cannot be differentiated with the method disclosed herein. Only paired-end sequencing that will catch the 5'-end of the V segment can discriminate these two sequences. Thus the hTRBV12-3 and hTRBV12-4 were considered as a unique sequence for the analysis of the repertoire.

Example 7: Linearity of TCR Gene Amplification

Because non-linear amplification of individual TCR sequences can lead to an incorrect over- or underrepresentation of the affected TCR genes in the final TCR repertoire, linearity of amplification is a critical determinant of the reliability and quality of the TCR sequencing data.

To test linearity of TCR gene amplification in our system, a fixed amount of DNA encoding a known TCR sequence was diluted at different concentrations into a DNA pool representing a naïve CD8 repertoire. Subsequently, the TCR repertoire of each sample was analyzed with SEQTR.

Figure 7:
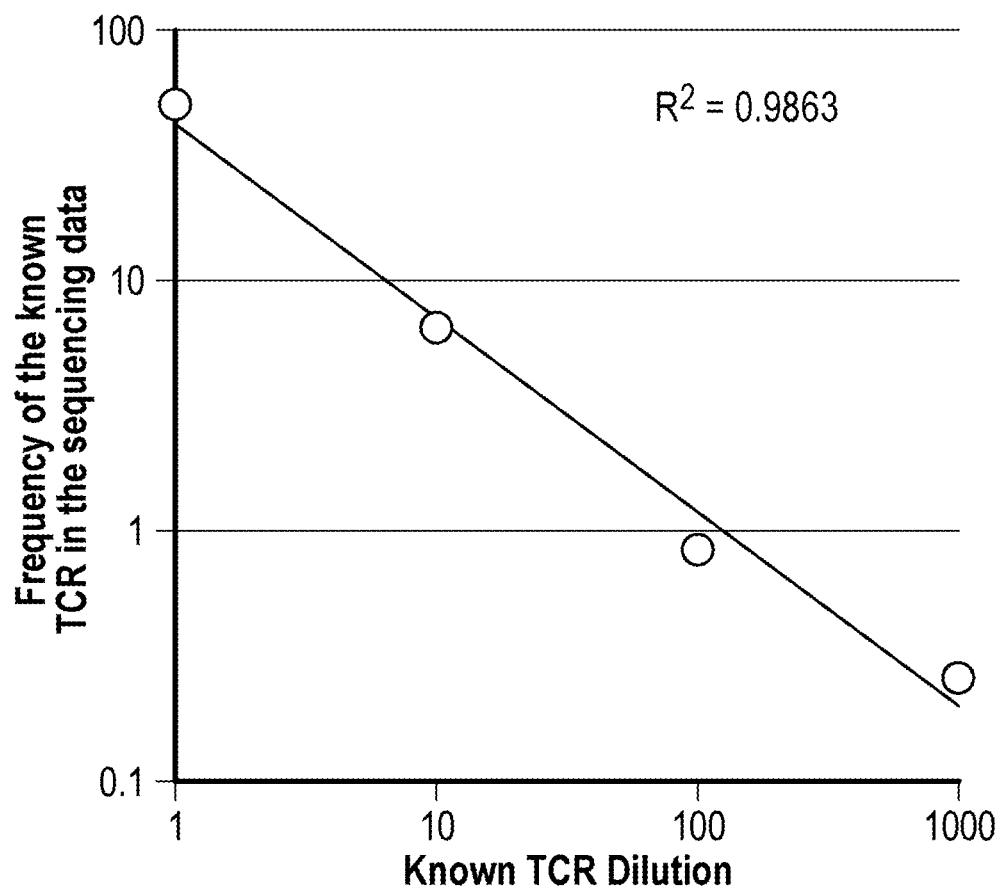
FIG. 7 illustrates the linearity of the SEQTR method. A fixed amount of DNA encoding a known TCR sequence was diluted at different concentrations into a DNA mixture representing a naïve CD8 T-cell repertoire. TCR repertoires of the individual mixtures were sequenced using the SEQTR method. The observed frequency of the known TCR sequence in the entire repertoire was plotted against the respective TCR gene dilution.

The observed frequency of the known TCR sequence in the entire TCR repertoire was then sequenced for each dilution and compared to the expected frequency. The scatter plot in FIG. 7 shows an excellent correlation ($R^2=0.99$) between the dilution and the frequency of the known TCR sequence in the repertoire observed after sequencing. These data confirm the linearity of the amplification and suggest that results obtained using the SEQTR technique are quantitative.

Example 8: Reproducibility of the SEQTR Method

Figure 8:
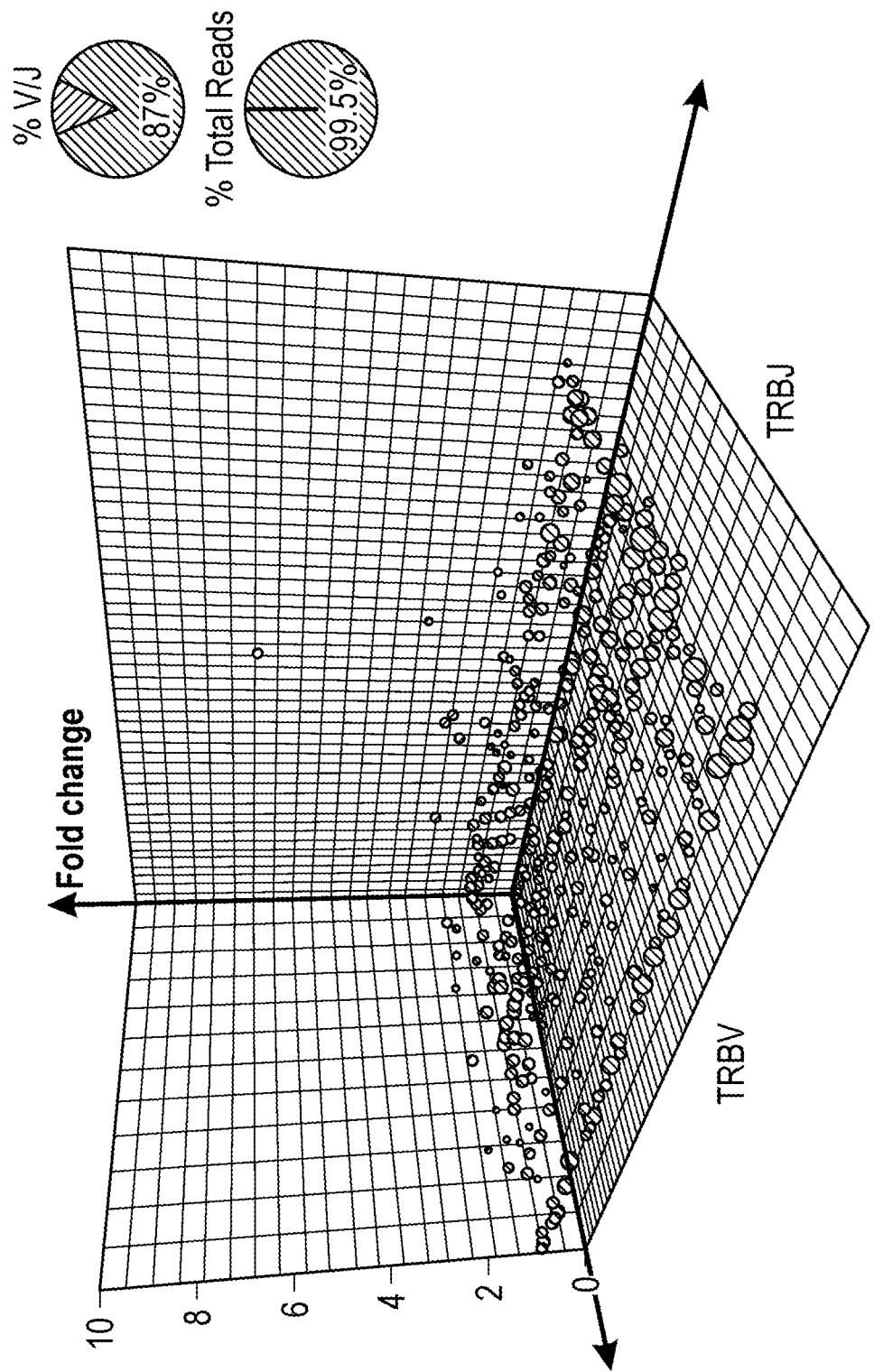
FIG. 8 illustrates the reproducibility of the SEQTR method. TCR repertoires were sequenced using the SEQTR method from one biological sample in two independent technical replicates. The frequencies for each V-J rearrangement/combination in TCR β chains were determined and compared between the two replicates. Each sphere represents a single V-J rearrangement with the size of a sphere indicating the relative frequency of the specific V-J recombination. Grey spheres represent rearrangements for which the relative frequencies detected in the two replicates differed by less than two-fold. Black spheres represent rearrangements for which the relative frequencies detected in the two replicates differed by more than two-fold.

The reproducibility of the method was tested by performing two independent technical replicates starting from the same sample. The frequencies for each V-J rearrangement in the TCR β chains were determined and compared between the two replicates, as illustrated in FIG. 8. Each sphere represents a single V-J rearrangement that was detected in both replicates. Each sphere represents a single V-J rearrangement with the size of a sphere indicating the relative frequency of the specific V-J recombination. Grey spheres represent rearrangements for which the relative frequencies detected in the two replicates differed by less than two-fold. Black spheres represent rearrangements for which the relative frequencies detected in the two replicates differed by more than two-fold. Consistent with common practice in the analysis of gene expression data, differences between replaces of less than 2-fold are not considered significant.

The data show that only 13% of all V-J rearrangements showed a significant frequency difference of more than two-fold between the two technical replicates (see FIG. 8 upper inset). However, as illustrated in FIG. 8, V-J recombinations that were significantly different between the technical replicates were rather poorly expressed, as indicated by the small sizes of the black spheres. Therefore, if the frequencies of the individual V-J rearrangement are taken into consideration, only 0.5% of the sequences showed more than a two-fold difference between the replicates (see FIG. 8 lower inset), demonstrating that the SEQTR method is very reproducible.

Example 9: Sequencing of Example Repertoires Using the SEQTR Method

The SEQTR method was tested on three different type of CD8 positive T-cells:
(1) T-cell population 1: CD8 positive T-cells isolated from peripheral blood mononuclear cells (PBMCs).
(2) T-cell population 2: CD8 positive T-cells as in population 1 were FACS sorted using tetramers. Tetramers are MHC molecules presenting a specific peptide, linked to fluorescent dye. Tetramers bind T-cell expressing a TCR that specifically recognizes the peptide. The fluorescent dye allows sorting of the desired T-cells by FACS.
(3) T-cell population 3: CD8 positive T-cells as in population 2 that were subsequently expanded in vitro.

Figure 9A:
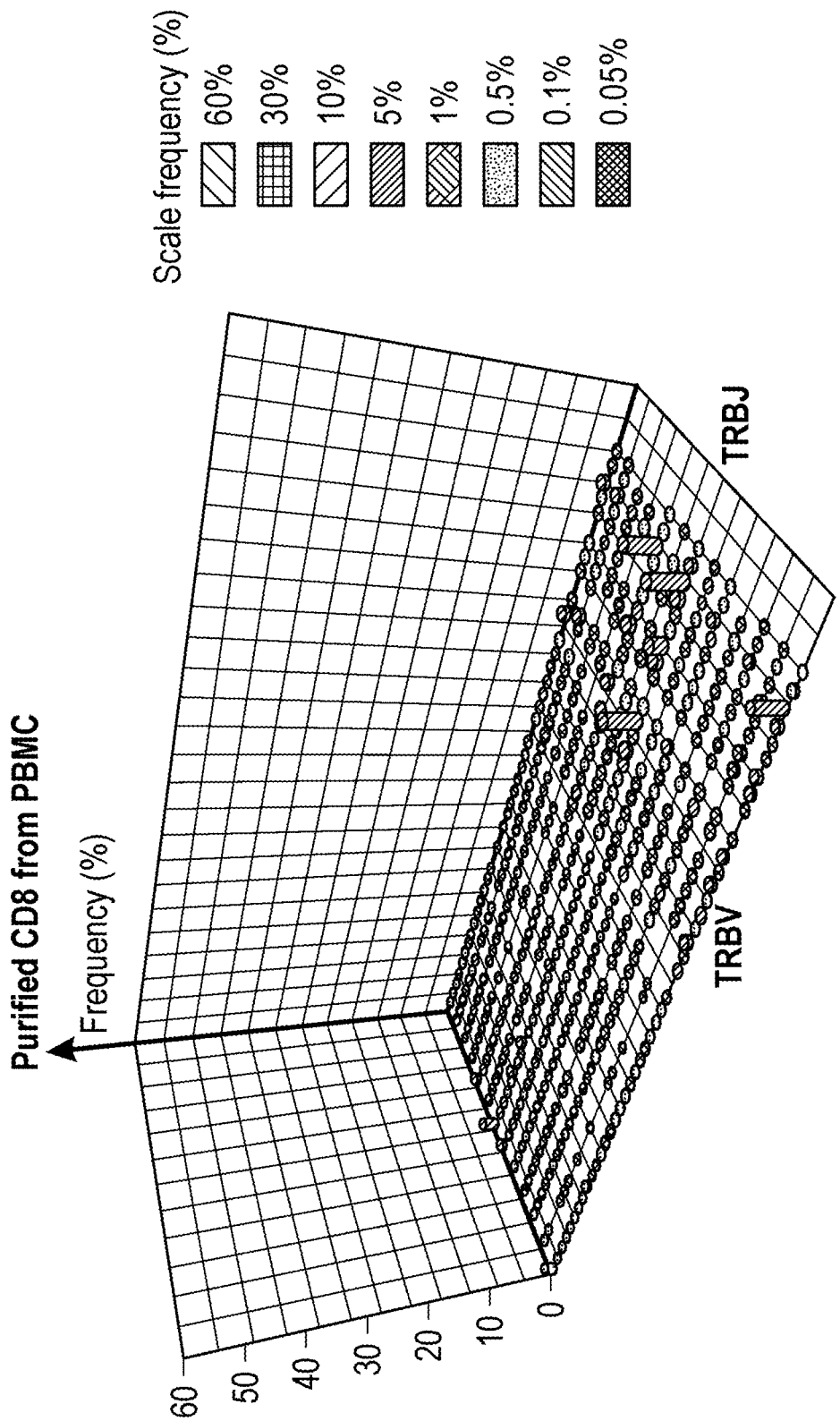
FIGS. 9A-9C illustrates the diversity of three different TCR repertoire sequencing data set using the SEQTR method.
Figure 9B:
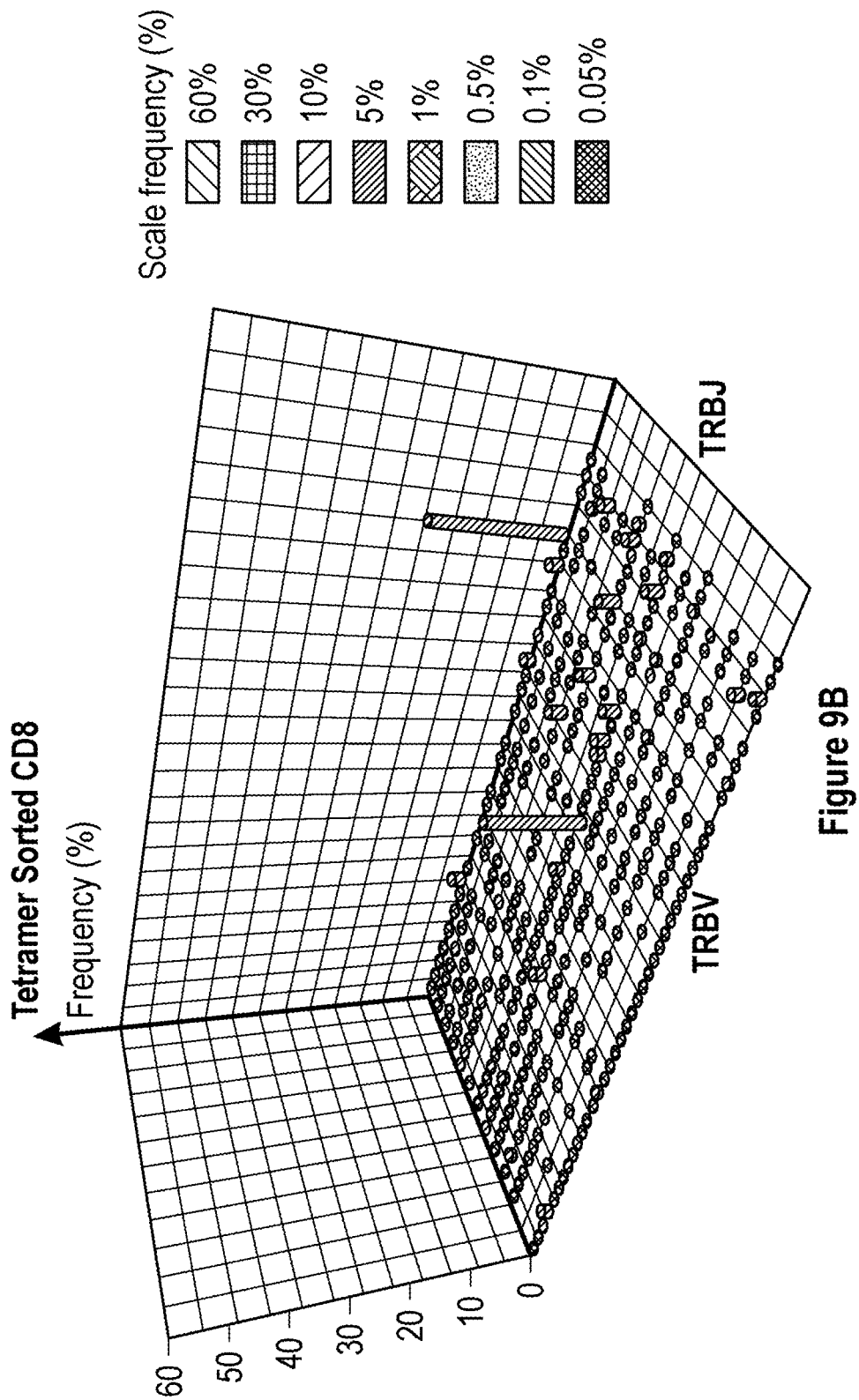
Figure 9C:
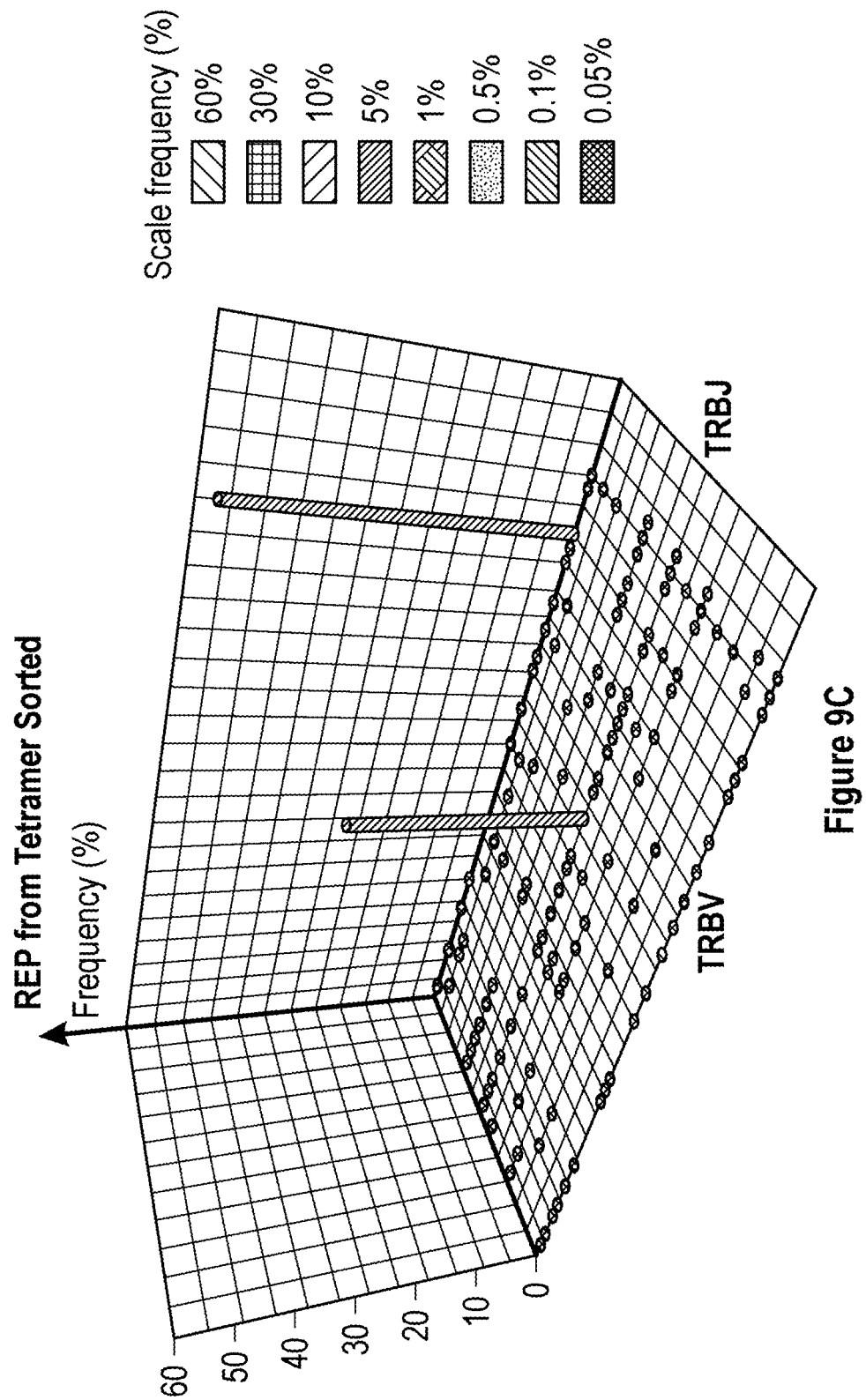
Figure 11:
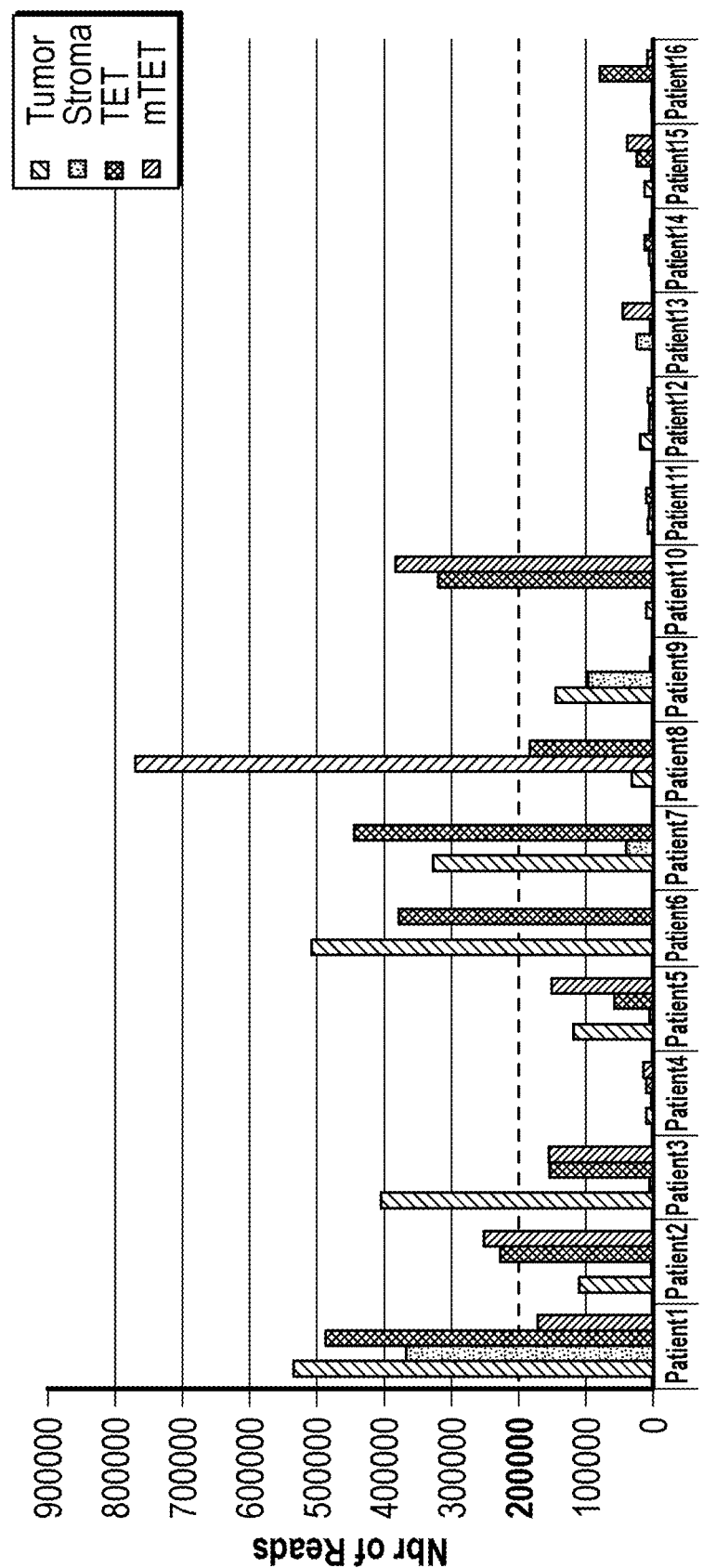
FIG. 11 illustrates the number of reads for different samples obtained using the TCR sequencing service "immunoSEQ®" offered by Adaptive Biotechnology. The requested number of reads per sample was 200,000 reads. The number on the x axis represent analysis of samples from 16 different patients. Columns, left to right, for each sample represent number of reads from: the tumor; the stroma (tissue surrounding the tumor); epitope specific TIL (Tumor Infiltrating Lymphocyte) stained with tetramer and sorted by FACS from the tumor sample (TET); and tetramer sorted TIL from a piece of the tumor that has been engrafted in a mice (mTET).

The relative frequencies of each V-J rearrangement were determined using the SEQTR method (see FIG. 9). As expected, the naïve TCR repertoire derived from PBMC (population 1) is highly diverse (see FIG. 9A). Almost all the possible V-J rearrangements are represented in the sample, with no single V-J rearrangement exhibiting a frequency of over 11% The repertoire of the tetramer sorted CD8 positive T-cell subset 2 (see FIG. 9B) is less diverse as compared to the naïve one. Not only are fewer V-J rearrangements present in the repertoire overall. Moreover, two V-J rearrangements are clearly dominant, exhibiting frequencies of over 20%. These V-J rearrangements represent the few T-cells that recognize the epitope TEDYMIHII (SEQ ID NO: 236) conjugated to the tetramer and that were enriched during the tetramer purification step. Finally, the rapid clonal expansion (population 3) of the tetramer-purified T-cells enhances the bias of the TCR repertoire towards the T-cell clones already dominating subset 2. Consequently, part of the low frequency V-J rearrangements are lost and not detected anymore (see FIG. 9C). In summary, these data illustrate that the SEQTR method is well suited to differentiate between TCR repertoires with different degrees of diversities.

Example 10: Comparison of the SEQTR Method with Low-Throughput Single Cell Cloning In order to determine how accurate the TCR repertoire data obtained using the SEQTR method were as compared to the true TCR repertoire present in a given T-cell population, we compared our results to data obtained by single cell sequencing.

Tetramer-specific CD8 were sorted from PBMC by FACS. The recovered cell population was split in two. Half of the cells were subjected to the SEQTR method to sequence the TCR repertoire. For the other half of the cells, individual T-cell clones were isolated and expanded in vitro (single cell cloning). Once the clones were established, the TCR genes of each T-cell clones were amplified and sequenced using classical Sanger sequencing (see FIG. 10A).

Among the 42 individual clones tested using the single cell method, six different TCRs were identified (see FIG. 10B). Using the SEQTR method, 116 different TCR genes were found (the eight most frequently observed V-J rearrangements are shown in FIG. 10C, also see Table 13 and Table 14). Indeed, the five TCRs most frequently observed with the single cell cloning technique also correspond to the five clones most frequently observed when applying the SEQTR method. Overall, all six TCR clones identified with single cell sequencing are represented among the eight TCRs with the highest frequencies observed in the SEQTR method. In summary, these data suggest that the SEQTR method produces a true representation of the actual TCR repertoire of a given T-cell population.

TABLE 13

CDR3 regions of TCR clones identified using the single cell sequencing method.

| SEQ ID NO | CDR3 region |
| --- | --- |
| 237 | CASSRHVGGVPEAFFG |
| 238 | CASSIGRGSEQYFG |
| 239 | CASSDVLSGEAFFG |
| 240 | CASQGHKNTEAFFG |
| 241 | CASSLGPGGVKTNEKLFFG |
| 242 | CASSLGPGGVKTNEKLFFG |

TABLE 14

Eight most frequently observed V-J rearrangements of the 116 different TCR genes identified using the SEQTR method.

| SEQ ID NO | CDR3 region |
| --- | --- |
| 243 | CASSDVLSGEAFFG |
| 244 | CASQGHKNTEAFFG |

TABLE 14-continued

Eight most frequently observed V-J rearrangements of the 116 different TCR genes identified using the SEQTR method.

| SEQ ID NO | CDR3 region |
| --- | --- |
| 245 | CASSLGPGGVKTNEKLFFG |
| 246 | CASSIGRGSEQYFG |
| 247 | CASSRHVGGVPEAFFG |
| 248 | CASSASKGQPQHFG |
| 249 | CASQGHKNTEAFFG |
| 250 | CASSLGPGGVKTNEKLFFG |

Example 11: TCR Sequencing Services Offered by Adaptive Biotechnology Provide Sequencing Data that May Reflect Up to 90% Unspecific TCR Amplification Tumor samples from 16 patients were collected and the tumor cells were separated from the surrounding tissue (stroma). In addition, epitope-specific TIL were sorted by FACS from the tumor samples using tetramer staining (TET). Finally, the tumor cells were engrafted into humanized mice. After some time, the tumor was collected and epitope specific TIL were sorted by FACS.

DNA extraction was performed for each sample. DNA was sent to Adaptive Biotechnology for TCR sequencing (immunoSEQ® method, survey protocol 200,000-300,000 reads per sample).

In 80% of the samples, the immunoSEQ® method failed to generate 200,000 reads per samples, suggesting that the immunoSEQ® method fails to generate TCR repertoires with significant reliability.

Example 12: Amplification of TCR Genes from PBMC and CD4 Positive T-Cells

RNA was isolated from $10^6$ PBMC or $10^6$ CD4 positive T-cells, respectively, from three independent samples, The RNA was then subjected to steps 2 to 4 of the SEQTR method outlined above (see Detailed Description of the Invention). PCR products were separated on an agarose gel and visualized (see FIG. 12). Only TCR-specific bands are observed, suggesting that the SEQTR method cannot only be used for CD8 positive T-cells (see Example 7), but also for CD4 positive T-cells and even for T-cells that are part of a complex mixture of other PBMCs.

The foregoing examples and description of the embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference herein in their entireties.

As described and claimed herein, including in the accompanying drawings, reference is made to particular features, including method steps. It is to be understood that the disclosure of the invention in this specification includes all possible combinations of such particular features. For example, where a particular feature is disclosed in the context of a particular aspect or embodiment, or a particular claim, that feature can also be used, to the extent possible, in combination with and/or in the context of other particular aspects and embodiments, and in the disclosed methods, systems and kits generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

TABLE 15

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV01-1 | hTRAV01-1 | 117 | ATGTGGGGAGCTTTCTTCTCTTATGTTTCCATGAAGATGGGAGGCACTGCAGGACAAAGCTTGAGCAGCCCTCTGAAGTGACAGCTGTGGAAGGACAACCATTGTCCAGATAAACTGCACGTACCAGACATCTGGGTTTTATGGCTGTCCTGGTACCAGCAACATGATGCGGAGCGACCCCACCATTCTTCTTCTTACAATGCTCTGATGGTTTGGAGGAGACAGGTCGTTTTTCTTCATTCCTTAGTCGCTCTGATAGTTATGGTTACCTC | CTTCTACAGGAGCTCCAGATGAAAG | ACTCTGCCTCTTACTTCTCGCTGTGAGAGA |
| hTRAV01-2 | hTRAV01-2 | 118 | ATGTGGGGAGTTTTCCTTCTCTTTATGTTTCCATGAAGATGGGAGGCACTACAGGACACAAAACATTGACCAGCCCACTGAGATACAGCTGCACGGAAGGTGCCATTGTCCAGATCAACTGGACGTACCAGACATCTGGTTCAACGGGCTGTTCTGGTACCAGCAACATGCTGGCGAAGCAACATCTGTCTTACAATGTTCTGGATGTTCTGGAGAGAAAGGTCGTTTTTCTTCATTCCTTAGTCGGTCTAAAGGGTACAGTTACCTC | CTTTTGAAGGAGCTCCAGATGAAAG | ACTCTGCCTCTTACCTCTGTGCTGTGAGAGA |
| hTRAV02 | hTRAV02 | 119 | ATGGCTTTGCTGAGACACTCTGGGGGCGGTGTTGGCTAGGGCTTTCTCTCAACTCTCTGAAGGTTGCAGAAAGCAAGGACCAAGTGTTTCAGCCTTCACAGGAGCTTCAGAGGGAGCTTGTGGTGGAAATCTTCTGTAATCACTCTGTGTCCAATGCTTACAACTTCTCTGTTCTGGTACTTCCTCCCGGATGTGCACCAAGACTCCTTGTTAAAGGCTCAAAGCCTTCTCAGCAGGACGATACAACATGACCTATGAACGGTTCTCTTCATCGC | TGCTCATCCTCCAGTTGCGGGA | GGCAGATGCTGCTGTTTACTACTGTGCTGTGGAGGA |
| hTRAV03 | hTRAV03 | 120 | ATGGCCTCTGCACCCATCTGCTTGCATGCTCTTCACATTGAGTGGGCTGAGAGCTCAGTGGCTCAGCCGGAAGATGCTCAAGCTGTGAAGGAATCCTCTGACGTGAAATGCACCTATTCAGTCTCTGGAAACCCTATCTTTTTTGTATGTTCAATACCCCAGAGGCCTCCAGTTCCTTCTGAAATACATCACAGGGGATAACCTGGTTAAAGGCAGCTATGCCTTTGAAGCTGAATTTAACAAGAGCCAAACCTCCTTCCACCT | GAAGAAACCATCTGCCCTTGTGA | GCGACTCCGCTTTGTACTTCTGTGCTGTGAGAACA |
| hTRAV04 | hTRAV04 | 121 | ATGAGGCAAGTGGCGAGAGTGATCGTGTTCCTGACCCTGAGTACTTTGAGCCTTGCTAAGACCACCCAGCCATCTCCATGAGACTCATATGAAGGACAAGAAGTGAACATAACCTGTAGCCACAACAAAATTACAAATGATTATATCACGTGGTACCAACAGTTTCCCAGCCAAGAACCACGATTATTATTCAAGGATACAAGACAAAAGTTACAAACGAAGTGGCCTCCCTGTTTATCCCTGCCAACAGTCCAGCACTCTGAG | CCTGCCCCGGGTTTCCTGAGCGAC | ACTGCTGTGTACTACTGCTCCTGGGTGACA |
| hTRAV05 | hTRAV05 | 122 | ATGAAGACACATTTGCTGATTTTGTTCCTGCTGAGTTTCTGGTCGTGCTGACTGTATGAGTGAGGAGGATGTGGAGCAGAGTCTTTTCCTGAGTGTCCAGAAGGAGACAGCTCCTGTTATAAACTGCACTTACACAGACAGCTCCTCCACCTACTTATACTGGTATAAGCAAGAACCTGGAGAAGGTCCACAGTTCCTCATTTCAACATATATTTTCAAATATGGACATGAAACAAGACCAAAGATCAACTGTTCTATTGAATAAAAGGGATAAAACATCTG | TCTCTGCGCATTGCAGACACCCA | GACTGGGACTCAGCTATCTACTTCTGTGCAGAGAGTA |
| hTRAV06 | hTRAV06 | 123 | ATGGAGTCATTCCTGGGAGTGTTTTGCTGATTTTGTGGCTTCAAGTGGACTGGGTGAACTACAGCCAAAAGATAGAACAGAATTCCGAGGCCCTGAACATTCAGGAGGGTAAAACGGCCACCCTGAACTGCAGCTACACACAAAACTATTCCCAGCATACTTACAGTGGTACAAGCAGGAGGCCCTGTTTTCTTGCTACAGCGTGAAAATGAAAGAAGGACTTAACGTGCACCCTTGTGATACCACCCTTAAACAGAGT | TTGTTTCATATCACAGCCTCCCA | GCCTGCAGACTCAGCTACCTACTCGTGCTCTAGACA |
| hTRAV07 | hTRAV07 | 124 | ATGGAGAAGATGCGAAGCAGCCCTCATTTTCTGGACCCTCAGCAGGAGACCTTGTCTATGTCTTGGCTGGCAAATGGAGAAAACCAGGTGGAGCACAGCCCTCATTTCTGTACTCCTACGGCTAGTTTAACAATTTGCAGTTGGTACAGTGAAAGATCCAGCAAAGGTCTCCATGAGCTTCCATGAGCTGCACGTACCTGTCAGTCGTTTAACAATTTGCAGTTGGTACAGTGAAAGATCCAGCAAAATACCAGCTATTACCATGTGAAGATCCAGTGCTGGAATATGAGAGAAGCAGAAGAAAAGGAAGACTAAATGCTACATTACTGAAGAATGAAGCA | GCTTGTACATTACAGCCGTGCA | GCCTGAAGATTCAGCCACCTATTTCTGTGCTGTAGATG |
| hTRAV08-1 | hTRAV08-1/08-3 | 125 | ATGCTCCTGCTTGCTCATACCAGTGCTGGGATGATTTTTGCCCTGAGCAGATGCCAGAGATGCCCAGTGTGCTGTGAGCCAGCATAAACCACCACGTAATTCTCTGAAGCACTAATGCTACATTACTGAGAATGAAGCA | ATCTGAGGAAACCCTCTG | GTGGAGTGACACAGCTGAGTACTTT |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV08-2 | | | AATCTCTTCTGGTATGCTCAGTACCCTGGTCAACACCCTTGCTCAGCTTCTCCTCAAGTACTTTTCAGGGATCCACTGG TTAAAGGCATCAAGGGCTTTGAGGCTGAATTTATAAAGAGTAAATTCTCCTTA | TGCA | CTGTGCCGTGAA TGC |
| hTRAV08-2 | hTRAV08-2/08-4 | 126 | ATGCTCCTGCTCTCCCAGTGCTCGAGTGCTTCTGAGGTGATTTTACTCTGGGAGGAACCAGAGCCCAGTCGGTGACCCAG CTTGACAGCCACGTCTCTGTCTTGAAGGAACCCCGGCTTGCTGAGGTGCAACTACTACTTCTTATTCACCAT CTCTCTTCTGTATGTGCAACACCCCAAAAGGACTCCAGCTTCTCGAAGTACACATCAGCGGCCACCCTGG TTAAAGGCATCAACGGTTTTGAGGCTGAATTTAAGAAGAGTGAAACCTCCTTCC | ACCTGACGA AACCCTCAG CCCAT | ATGAGCGACCGC GCTGAGTACTTC TGTGTTGTGAGT GA |
| hTRAV08-3 | hTRAV08-3 | 127 | ATGCTCCTGGAGCTTATCCCACTGCTTGGGGATACATTTTGTCCAGAGCCCAGTCAGTGACCCAG CCTGACATCCACATCACTGTTCTGAAGGAGGCTCACTGAGGTGATGAACTATTCCTATGGGGCAACACCT TATCTCTTCTTCCAGTCCCCCCGGGCCCAAGGCCTCCAGCTGTCCTGAAGTACTTTTCAGGAGACACTCTGG TTCAAGGCATTAAAGGCTTTGAGGCTGAATTTAAGAGGAGTCAATCTTCTTCA | ATCTGAGGA AACCCTG TGCA | TTGGAGTGATGC TGCTGAGTACTT CTGTGCTGTGGG TGC |
| hTRAV08-4 | hTRAV08-4 | 128 | ATGCTCCTGCTCTCCCAGTGCTCGAGTGCTTCTGAGGTGATTTTACCCTGGGAGGAACCAGAGCCCAGTCGGTGACCCAG CTTGGCAGCCACGTCTCTGTCTCTGAATACCCCAACCAAGGACTCCAGCTTCTCCTGAGGTGCAACTACTCATCGTCTGTTCCACCAT ATCTCTTCTGTATGTGCAATACCAAGGACTCCAGCTTCTCCTGAAGTACACATCAGCGGCCACCCTGG TTAAAGGCATCAACGGTTTTGAGGCTGAATTTAAGAAGAGTGAAACCTCCTTCC | ACCTGACGA AACCCTCAG CCCAT | ATGAGCGACCGC GCTGAGTACTTC TGTGCTGTGAGT GACACA |
| hTRAV08-5 | hTRAV08-5 | 129 | ATGCTCCTGTTGCTCTCTGGTGCTCATCCCACTGCTGGGGATACATTTTGTCCTGAGTGAGAACTGTCAGAGCCCAGTCAGTGAC CCAGCCTGACATCCGCATCACTGTCTCTGAAGGAGCCCACTGGAGTGTGAGATGTGAACTATTCCTATGGGCGAT GTTGTGGAAGTCAGGACCCCCAAGGAGGACCCGCTGAAGCCATGGCAAGGAATGTGAATGTCTTCTTCTCTTATCCTCCTTTACTGCAATCTCTAAACA TAAATTGTAAAGATTTCATGGACACTTATCTCACTTCCCAATCAATACCCCTGATTT | CCTATGCCT GTCTTTACT TTAATC | TCTTAATCCTGTC AGCTGAGGAGGA TGTATGTCACC |
| hTRAV08-6 | hTRAV08-6 | 130 | ATGCTCCTGCTGCTCTCCCAGCGTTCCAGGTTGATTTTACCCTGGGAGGAACCAGAGCCCAGTCTGTGACCCAG CTTGACAGCCAAGTCCCTGCTTGTTCTTGAAGAAGCCCTGTGAGTGCAACTACTACTTCTGTCTTTCAGTG TATCTCTTCTGTATGTGCAATACCCCAACCAAGGACTCCAGCTTCTCCTGAAGTATTATCAGGATCCACCCTGG TTAAAGGCATCAACGGTTTTGAGGCTGAATTTAACAAGAGTCAAACTTCCTTCCA | CTTGAGGAA ACCCTCAGT CCATAT | AAGCGACACGGC TGAGTACTTCTG TGCTGTGAGTGA |
| hTRAV08-7 | hTRAV08-7 | 131 | ATGCTCTTCAGTGGTCATTCTGCCTTGCTTGGAATGTTCTTCACACTACTGAAGTGCAACTATTCCTATGGTGACCCAGTT GATGGCCACATCACTGTCTCTGAAGAGGCCCCTCTGAAGTGCAACTATTCCTATGGAGTTCCTTCT CTCTTCTGGTATGTCCAATATCTAGCCAAGACCCAAAGCTTCTCCTCAGCTTCTCCTCAAAGACCTAACAGAGGCCACCCAGGTT AAAGGCATCACGAGGTTTTGAGGCTGAATTTAAGAAGAGCGAAACCTCCTTCTACTTCTGAG | GAAACCATC AACCCATGT GAGTGA | TGCTGCTGAGTA CTTCTGTGCTGTG GGTGACAGG |
| hTRAV09-1 | hTRAV09-1 | 132 | ATGAATTCTTCTCCAGGACCACCAGCGATTCACTATTCTTAATGTTTGGGGGAATCAATGAGGATTCAGTGGTCCAG ACAGAAGCCCCAAGTGCTCCCCTTGAAGGGGATTCCTGAGTTGTGAACTGCTCTATGAAGGCCATGAAGCCACACAGTACCT TCCCTTTTTGGTATGTCCAATATCCTGGAGAAGGTTCCACCTGAAAGGCCATGAAGGCCAATGACAAG GGAAGGAACAAAGGTTTTGAAGCATGTACCGTAAAGAAACCACTTCTTTCC | ACTTGGAGA AAGACTCAG TTCAA | GAGTCAGACTCC GCTGTGTACTTCT GTGCTCTGAGTG A |
| hTRAV09-2 | hTRAV09-2 | 133 | ATGAACTATTCTCCAGGCTTAGTATCTCTGATATCTTACTGCTTGGAAGAACCCGTGGAAATTCAGTGACCCAG ATGGAAGGGCCAGTGACTCTCCTGAGAAGAGGCCTTCGACTATAAACTGCACGTACAGCACCACAGGATACCC TTCCCTTTTCTGGTATGTCCAATATCCCAATGCTCCAGCTCCTCCTGAAAGCCACGAAGGCTGAATGACAA GGGAAGCAACAAAGGTTTTGAAGCCACATACCGTAAAGAAACCACTTCTTCC | ACTTGGAGA AAGGCTCAG TTCAA | GTGTCAGACTCA GCGGTGTACTTC TGTGCTCTGAGT GA |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV10 | hTRAV10 | 134 | ATGAAAAAGCATCTGACGACCTTCTGGTGATTTGTGGCTTTATTTTATAGGGGAATGCAAAAACCAAGTGGAGCAGAGTCCTCCAGTCCCTGATCATCTGGAAGCAACTTCGGAGGGAAAGAACTGCACTCTTCAATGCAATATACAGTGAGCCCCTTCAGCAACTTAAGGTGTATAAGCAAGATACTGGGAGAGTTCCTGTTCCCTGACAATCATGACTTTCAGTGAGAACACAAAGTCGAACGGAAGATATACAGCAACTCTGATGCAGAACACAAAGCAAAGCTCT | CTGCACATCACAGCCTCCCA | GCTCAGCGATTCAGCTCCTACATCTGTGTGGTGAGCG |
| hTRAV11 | hTRAV11 | 135 | ACGGAGAGAGCCCTTGGAGTTTCATTCTTGATTCCTCCTGCAGCTGTGCTGGGTGAATAGACTACATACACTGGAGCAGAGTCCTTCATTCCTGAATATTCAGGAGGAGCATGCCGTTCTTAATTGTACTTATCAGGAGAACACTCTTCAATTTCCACTGGTTCCGGAGATCCGGGAGAAGAACTTGTGTCTTTGACCTTAATTCAATCAAGCCAGAAGGAGCAGGAGACAAATATTTTAAAGAACTGCTTGGAAAAGAAAATTTTATAGT | GTTTGAATATCGCAGCCTCTCAT | CTGGAGATTCAGCCACCTACTTCTGTGCTTTGC |
| hTRAV12-1 | hTRAV12-1 | 136 | ATGATATCCTTGAGAGTTTACTGGTGATCCTGCCTTCAGTTAAGCTGGGTTTGGAGCCAACGAAGGAGGTGGAGCAGGATCCTGGACCCTTCAATGTTCCAGGAGGAGCCACTGTCGCTGCTTCAACTGTACTTACAGCAACAGTGCTCCCAGTCCTTTCTTCTTGGTACAGACAGGATTGCAGGAAAAGAACCTAAGTTGCTGATGTCCGTATACTCCAGTGGTAATGAAGATGAAGGTTTACAGCACAGTCAATAGAGCCAGCCAGTATATTT | CCCTGCTCATCAGAGACTCCAAG | CTCAGTGATTCAGCCACCTACTCTGTGTGGTGAACA |
| hTRAV12-2 | hTRAV12-2 | 137 | ATGAAAATCCTTGAGAGTTTTACTAGTGATCCTGTGCTTCAGTTGAGCTGGTTTGAGCCAACAGAAGGAGGTGGAGCAGAATTCGGACCCCTCAGTGTTCCAGGAGCCATTGCCTCTCCAACTGCACTTACAGTGACCGAGGTTCCCAGTCCCTTCTTCTTGGTACAGACAATATTCTGGGAAAAGCCCTGAGTTGATAATGTTCATATCTCAATGGTGACAAAGAAGATGGAAGGTTTACAGCACAGTCAATAAAGCCAGCCAGTATGTTT | CTCTGCTCATCAGAGACTCCCAG | CCCAGTGATTCAGCCACCTACTCTGTGCCGTGAA |
| hTRAV12-3 | hTRAV12-3 | 138 | ATGAAAATCCTTGAGAGTTTTACTGGTGATCCTGTGCTTCAGTTAAGCTGGGTTTGAGCCAACAGAAGGAGGTGGAGCAGGATCCTGGACCCAGTGTTCCAGGAGCCATTGTTTCTTCTCAACTGCACTTACAGCACTACTCCAGTGGTTTTCAATACTTCATGTGTACAGACAGTATTCAGAAAAGCCCTGAGTTGCTGATGTACACATACTCCAGTGGTAACAAAGAGATGAAGGTTTACAGCACAGTCGATAATCCAGCAGTATATCT | CCTTGTTCATCAGAGACTCACAG | CCCAGTGATTCAGCCACCTACTGTGCAATGAGCGCACAG |
| hTRAV13-1 | hTRAV13-1 | 139 | ATGACATCCATTCGAGCTCGAGTCTGTATTATTATTCCTGTGCTGCACAGCCGTGTTATCAGCAACTGTCTTATTCATTATAGACATTCGTTCAAATGTGGGCGAACATCCTTCAACCCTGAGTGCCAGGAGGAGCAGCGTGTTATCAGCAACTGTCTTATTCATTATAGACATTCGTTCAAATGTGGGCGAATACTTCCCTTGGTATAAGCAAGAACCTGGAAAAGAACCTAAGCTGTTTACAGCAAGACCAACAGCCAAACATTTC | TCCCTGCACATCACAGAGACCCAA | CCTGAAGACTCGGCTGTCTACTTCTGTGCAGCAAGTA |
| hTRAV13-2 | hTRAV13-2 | 140 | ATGGCAGGCATTCGAGCTTTCAGCCCTACCCCTGAGTGTCCAGGAGGGTGACAACTTCATTATCAACATGTGCTTATTCAAACAGCCCTCAGACTACTTCATTTGGTACAGCAAGAATCTGGAAAAGAGCTGCTAATCATTATAGACATTCGTTCAAATATGGACAAAATGTCAAGGCCAAAAGTCACCCGTTTATTGAATAAGACAGTGAAAACATCTC | TCTCTGCAAATTGCAGCTACTCAA | CCTGGAGACTCAGCTGTCTACTTTTGTGCAGAGAATA |
| hTRAV14 | hTRAV14 | 141 | ATGTCACTTTCTAGCCTCTGCTGAAGGTGGTCACAGCTTCACTGTGGCTAGGACCTGGCATTGCCAGGAAGATAACTCAAACCCAACCAGGAATGTTCGTGAGAAGAGGCTTGTCGACTGCACATATGACACCAGTGATCAAGTTATGGGTCTATTCTTGGTACAGCAAGCAGCCCAGCAGTGGGAAATGATTTTTCTTATTATCAGGGGTCTTATGACGAGCAAAATGCAACGAAGGCGCTACTCAGTATTGAATTTCCAGAAGGCAAGAAAATCCGCCAACC | TTGTCATCTCCGCTTCACAACTGG | GGGACTCAGCAATGTATTTCTGTGCAATGAGAGAGGG |
| hTRAV15 | hTRAV15 | 142 | ATGTATACGTATGTAACAAACCTGCGCGTTGCGCAATGTACCCTAGAACCTGTGAACAGCCTCCATATTCTGAAGGACTGCCTTTGGAATATCCCGGAGGGAATGCACACATTCACTTATGAGGAGGAACGTTGCTTCTTACTTCATCCTCTACTGGTTCTGCCAGGGTCTGAAAGGACTGTCTGTCTTTGACCTTAATTCAATCAAGCCAGATGGAGGAGGAGACAAACATTTAAGAGACGCCTTGGAAAGAGAAGTTTATAGT | GTTTTGAATATGCTGGTCTCTCAT | CCTGAGATTCAGGACCTACTTCTGTGCTTTGAGG |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV16 | hTRAV16 | 143 | ATGAAGCCACCCTCATCTCAGTGCTTGTGATAATATTATACTCAGAGGAACAAGAGCCCAGAGAGTGACTCAGCCCGAGAAGCTCCCTCTGTCTTTAAAGGGGCCCCAGTGGAGCTGAAGTGCAACTATTCCTATTCTGGAGTCCTGAACTCTTCTGGTATGTCCAGTACTCCAGACAACGCCTCCAGTTACTCTTGAGACACATCTCTAGAGAGCATCAAAGGCTTCACTGCTGACCTTAACAAAGGCGAGACATCTTTCCA | CCTGAAGAAACCATTTGCTCAAGA | GGAAGACTCAGCCATGTATTACTGTGCTCTTAAGTGG |
| hTRAV17 | hTRAV17 | 144 | ATGGAAACTCTCCTGGGAGTGTCTTTTGTGATTCATATGGCTTCAACTGGCTAGGGTGAACAGTCAACAGGGAGAAGAGGATCCTCAGGCCTTGAGCATCCAGGAGGGTGAAAATGCCACATGAACTGCAGTTACAAAACTAGTATAAACAATTTACAGTGGTATAGACAAATTCAGTAGAGGCCTTGTCCACCTAATTTAATGCGTTCAAATGAAAGAGAGAAACACAGTGGAAGATTAAGACTCACGCTTGACACTTCCAAGAAAGCAGT | TCCTTGTTGATCACGGCTTCCCGG | GCAGCAGACACTGCTTCTTACTTCTGTGCTACGGACG |
| hTRAV18 | hTRAV18 | 145 | ATGCTGTCTGCTTCTCTGCTCAGGACTTGTGATCTCTGTTGATATTCAGAAGGACCCAGTGGAGAACTGGTTACCCAGACAGAAGGCCCAGTTACCCCTCCCTGAGAGGGCAGCTCTGACATTAAACTGCACTTATCAGTCCAGCTATTCAACTTTTCTATTCTGTATGTCCAGTATCCAAAAGAGCCTCCTCCGAGTCCTCCTGAAAAGTTCAGAAAACCAGGAGACGGACAGCAGAGAGTTTTCAGGCCAGTCCTATCAAGAGTGACAGTTCCTTCC | ACCTGAGAAGCCCTTCGGTGCA | GCTGTCGGACTCTGCCGTGTACTACTGCGCTCTGAGA |
| hTRAV19 | hTRAV19 | 146 | ATGCTGACTGCCAGCCTGTTGAGGGCAGTCAGTCATAGCCTCCATCTGTGTATCCAGCATCTGTGTGTATCCAGCTGTGCAGAAGGTAACTCAAGGGCTGCTGAAATTCTGTGGTGGAGAAGGAACACCAACCAAGTGGAGATGGGACCTGGACTGTGTGATAATGACCCGTGATACTACTTATTACTTATTCTGCTAGATCAACCTAGTCAACTTGTTTTCTTATTCGTCGGAACTCTTTTGATGAGCAAAATGAAATAAGTAAGAACTTCTTGGAACTTCCAGAAATTCCACCAGTTCCTTCAACTT | CACCATCACAGCCTCACAAGTCGT | GGACTCAGCAGTATACTTCTGTGCTCTGAGTGAGGC |
| hTRAV20 | hTRAV20 | 147 | ATGGAGAAAATGTTGGAGTGTGCATTCATAGTCTTATAGTCTTCAGCTTGCTTGAGTGGAGAGACAGGGTGACGCAGAGTCCGAGCAGCTCTGAGTGTCCCAGAAGATAGTCAGTACGCAGTCGAGACGACGAGTCAGCGTTTAAGAGGGCTGCTGTTCGGTAGCAAGATCCTCGGGAGAAAGGTCCATATCTGTGCTTATTCGTCGGAACTCTCTCACCCGTATTCAGCTGGGAAGAAGAAGAGAGCTAAAAGCCACACATTAACAAGAAGAAGAAGC | TTTCTGCACATCACAGCCCCTA | AACCTGAAGACTCAGCCACTTATCTCTGTGCTGTGCAGG |
| hTRAV21 | hTRAV21 | 148 | ATGGAGACCCCTCTGGCCTCTACTCTTTGGCTCGAGCTGCAATGGGTGAGCAGCAAACAGGAGGCTGACGCAGATTCCTGCAGCTCTGAGTGTCCAGAAGAGCCTGGTCTTCAACTGGTTCTCACATCTCTGTTCTTATTCAGTCAAGTCAGAGACGCTATTTACAACCTCCAGTGGTTTAGGCAGGACTTGGGAAAAGGCCTCTATATTGTTGCTCATCTGTTGCTTATTCAGTCAAGTCAGAAGACGTAGTA | CTTTATACATTGCAGCTTCTCAGCC | TGGTGACTCAGCCACCTACCCTGTGCTGTGAGG |
| hTRAV22 | hTRAV22 | 149 | ATGAAGAGGATATTGGGAGCTCTGCTGCTCTGCTCGCCTCTGCAGACGCTAAGTTGGAGAGAATTCAGTGGAGCAGAGTCCTCCAGACCTGATTCTCCAGGAGGAGGAGCCAATTCCACGCGCGTCCAATTTCTGACTCTGTGAACAATTTGCCAGTGGTTTCATCAAAACCCTTGGGGACAACCTGTTTACATTCCCTCAGGGACAAATACAGAATTGGAAGATTAAGCGCCACGAGTGCGCTACGGAACGCTACAGCTTATT | GTACATTTCCTCTTCCCAGACCAC | AGACTCAGGCGTTTATTTCTGTGCTGTGGAGC |
| hTRAV23 | hTRAV23 | 150 | ATGGACAAGATCTTAGGAGCATCATTTTAGTTCTCTGGCTTCAACTATGCTTCAACTATTTGATAGTCCAAGGAGGAGGATTTCAATTATAAAAAAAGTGACCAGCAGCAGGTGAAACAAGTCCTCAATCTTTGATACAATCCCTGGACAATTCCCTGGACAAGTTCAATTAATTTCATTAATTCCTCGTGCTTATGAAGAACACCTGCGTTTGACTACTTCCACATGGAACAATTCCCTCAATAAAAGTGCCAAGCGATAGCCATACCGTCCAGATGTGAGTAGTGAAAAAGAAGAGATTCACAAATCCTCCTTCAATAAAAGTGCCAAGC | CATTGCATATCATGATTCCCAGC | CTGGAGACTCAGCCACTTACTTCTGTGCAGCAAGCA |
| hTRAV24 | hTRAV24 | 151 | ATGGAAGAAGAATCCTTTGGAGCAGCCCCATTACTAATCCTCTGGTTTCATCTTGACTCGTGAGCAGCATAACTGAACGTGGAACAAAGTCCTCAGTCACTCAGTTCAGGAGGAGGAGACAGCACCAATTTCACCTGCAGCTTCCTCGAGCAGCTTCCCTTCCAGC | GCTATTTGTACATCAAAG | AGCCTGAAGACTCAGCCACCATACC |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV25 | hTRAV25 | 152 | AATTTTATGCCTTACACTGGTACAGATGGGAAGATGCAAAAAGCCCCGAGGCCCTTGTTGTTGTAATGACTTTAAAT GGGGATGAAAAAGAAGTGCCACTCTTAATACCAAGGAGGTTACA | GATCCC | TCTGTGCCTTTA |
| hTRAV26-1 | hTRAV26-1 | 153 | ATGCTACTCATCACATCAATGTTGGTCTTATGGATGCAATTGTCACAGGTGAATGACAACAGGTAATGCAAATT CCTCAGTACCAGCATGTGACAAGGAGGAGAGACTTCACAACGTCCTGCAATTCCTCAACTACTTTAAGCAATATA CAGTGGTATAAGCAAGGCCTGGTGGACATCCGTTTTTTTGATACAGTTAGTGAAGAGTGGAGAAGTGAAGAA GCAGAAAAGACTGACATTTCAGTTTGAGAAGCAAAAAGAA | CAGCTCCCT GCACATCAC AGCCA | CCCAGACTACAG ATGTAGGAACCT ACTTCTGTGCAG GG |
| hTRAV26-2 | hTRAV26-2 | 154 | ATGAGGCTGGTGGCAAGATAACTGTTGTTTCAGCAGTAACTATAATTGATGCTAAGACCACCAGCCTGC TCCATGATGTGCGTGAAGAGGAGAGTCCAAACCTGCCTTGTAATCACTCTACCATCAGTGGGAAATGAGTATGTG TATTGGTATCGACAGATTCACTCCCAGGGCCACAGTATATCATTCATGGTCTAAAAAACAATGAAACCAATGA AATGGCCTCTCTGATCATCACAGAAGACAGAAAGTCCAGACC | TTGATCCTG CCCCACGCT ACGCTGA | GAGACACTGCTG TGTACTATTGCA TCGTCAGAGTCG |
| hTRAV27 | hTRAV27 | 155 | ATGAAGTTGGTGACAAGCATTACTGTACTCCTATCTTTGGGTATTATGGGTGATGCTAAGACCACACAGCCAAAT TCAATGGAGAGTAACGAAGAAGAGCTTCCCTCCCAGGGTCCAGAGTACGTGATTCATGGTCTTACAAGCAATGTGAACACAGA CATTGGTATCGACAGCTTCCCTCCCAGGGTCCAGAGTACGTGATTCATGGTCTTACAAGCAATGTGAACACAGA ATGGCCTCTCTGGCAATCGCTGAAGACAGAAAGTCCAGTACC | TTGATCCTG CACCGTGCT ACCTTGA | GAGATGCTGCTG TGTACTACTGCA TCCTGAGAGAC |
| hTRAV28 | hTRAV28 | 156 | ATGGTCCTGAAATTCTCCGTGTCCATTCTTTGGATTCAGTTGGCATGGGTGAGCACCCAGTGCTGCTGGAGCAGAGC CCTCAGTTTCTAAGCATCCAAGAGGGAGAAAATCCACTGTGTACTGCAACTCCTCAAGTGTTTTTTCCAGTTAC AATGGTACAGACAGGACCTGGGGAAGGTCCTGTCCTCTGTGACAGTAGTTACGGTGAGAAGTGAAGAAG CTGAAGAGACTAACCTTCAGTTTGGTGATGCAAGAAGGACA | GTTCTCTCC ACATCACTG CAGCC | CAGCCTGGTGAT ACAGGCCTCTAC CTCTGTGCAGGA G |
| hTRAV29 | hTRAV29 | 157 | ATGGAAGGCATTAATAAGGAAATCTGTGGGCTTCCTGGGCTTGTGGCTTCAGCCAGACTCTGTGGCTTCAGCCAGACTGGGTAAACAGTCAACAGAGAA TCCTCAGGTCCTGATCCTCCAAGAGGGAAGATCATTCTCGGTGTGCAGTTGTTCTATTTACATGATCCGTGTG CAGTGGTTTCATCAAAAGCCTGGAGGACCCCTCATGTCCTTATTTAACATTAATTCAGGAATACAGCAAAAAAGA AGACTAAAATCCGCAGTCAAGCTGAGGAACTTTATG | GCCACCTAT ACATCAGAT TCCCA | GCCTGAGGACTC AGCTATTACTTC TGTGCTGTGGGG A |
| hTRAV30 | hTRAV30 | 158 | ATGGCCATGCTCCTGGGGCATCAGTGCTGATTCTGTGGCTTCAGCCAGACTGGAGCTGTAAACAGTCAACAGAGAA TGATGACCAGCAAGTTAAGCAAGTTTTCACCATCTCTGAGCCTCCAGGAAGGAAGAGAATTCTATTCTGAACTGTG ACTATACTAACACATGTTTGATTATTTCCTATGGTACAAAAAATACCTGCTGAAGGTCCTACATTCCTATATC TATAAGTTCCATTAAGGATAAAAATGAAGATCGAAGATTCACTGTCTTCTTAAACAAAGTGCCAAGCACCTC | TCTCTGCAC ATTGTGCCC TCCCA | GCCTGAGACTC TGCAGTGTACTT CTGTGCAGCAAG CG |
| hTRAV31 | hTRAV31 | 159 | ATGGCCATGCTCCTGGGGCATCAGTGCTCTTTCAGGCACCTTGTGTGCCAGTTGAAGCCAACAACCAGTG CAGAGTCCTCAACTGCACCTACCAACACAGAGGGAAGATGCTGTCATCAACAGTCAGTTCTCCAAGGCTTTATAT TCTGTACACTGGTACAGCAGACATGTGAAGCACCCGTCTTCCTGATGATATTACTGAAGGGTGGAGAACA GAAGGGTCATGAGAAAATATCTGCTTCATTTAATGAAGAAGCAGCAAAGCT | CCCTGTACC TTACGGCCT CCCAGCT | CAGTTACTCAGG AACTACTTCTG CGGCACAGAGA |
| hTRAV32 | hTRAV32 | | | | |
| hTRAV31 | hTRAV31 | 159 | ATGACTGTTGCAGCATAATTACGGGCACTCATGGCCTCTTCCTTCTCGATGTCACAGAGGGTCATTCAATCC AACCAGCAATATCTACGCAGGAGGTGAGACCGTGAACTGACTGCATACAAAACTAATATTGTATATAC ATATTGTATTGGTACAAAAGGTCTCCCAATGGGAAGATTATTTTCCTCATTATTCAGCAAACAGATGCAAAAACC AATGCGACACAGGGTCAATATTCTGTGAGCTTCCAGAAAACAACTAAAACTATTCAG | CTTATCATA TCATCATCA CAGCCA | GAAGACCTGCAA CATATTTCTGTTG TCTCAAAGAGCC |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV32 | hTRAV32 | 160 | ATGGCAAGAAGAATGAAAAGTCCCTGGGACTTTATTCAAATTCAGCTGAAGCTGCCAAGAAAAGGATGTGATACAGAGTTATTCAAATCTAAATGTCTAGGAGAGAAGAAATGCCGTTATTAATGACAGTTATACAGATGAGCTTTGAATTATTTCTGTTGGTACAAGAAGAAACGGGAAGGCCCTAATATCTTAATGGAGATTCATTCAAATGTGATAGAAAACAGGACAGAAGGCTCACTGTTGAATAAAAATGCTAAACATGTC | TCCCTGCATATTACAGCCACCCAA | CCAAGAGACTCATTCCTGTACTTCTGTGCAGTGAGAACACA |
| hTRAV33 | hTRAV33 | 161 | ATGCTCTGCCCTGGCCTGCTGTGGGCATTCGTGTCTCCCCTTTGGCTTCAGATCCAGCATGGCTCAGAAAGTAACCCAAGTTCAGACCACCAGTAACTAGGCAGAAAGGAGTAGCTGTGACTTGGACGTGTGTTTGAAACCAGATAGAATTCGTACACTTTATACGGTACAAGCAACAACCTCCCAGTGAAGAGATGGTTTTCCTTATTCATCAGGGTTATTCTAAGTCAAATGCCAAGCCTGTGAACTTTGAAAAAAACAGAAAAAGTTCATCA | ACCTCACCATCAATTCCTTAAAAC | TGACTCAGCCAAGTACTTCTGTGCTCTCAGGAATCC |
| hTRAV34 | hTRAV34 | 162 | ATGGAGACTGTTCTCGAAGTACTCCTAGGGATATTGGGGTTCCAAGCAGCCTGGGTTCAGTAGCCAAGAACTGGAGCAGAGTCCCTGAGTCCAGTCCTTGATCGTCCAAGAGGAAAGAATCTCACCATAAACTGCACGTTCATCAAAGACGTTATATGGCTTATACGTGGTATAAGCAAAATATGTGAAGGTCTTATCTTCTTGATGATGCTACAGAAAGGTGGGAAGAGAAAGTCATGAAAAGATAACTGCCAAGTTGGATGAGAAAAGCAGCAAAGT | TCCCTGCATATCAAGACCTCCCAG | CCCAGCCATGCAGGCATCTACCTCTGTGGAGCAGACA |
| hTRAV35 | hTRAV35 | 163 | ATGCTCCTTGAACATTTATTAATAATCTTGTGGATGCAGCTGACATGGGTCAGTGTCAGTGTGAATACAGAGTCCTCAATCTATGTTTATCCAGGAAGGAAGAATGTCTCCATGAACTGCACCTTCTTCCAAGCATATTAACACCTGGCTATGGTACAAGCAGGAACCTGGGAAGGTCCTGTCGTTGATAGCCTTATATAGGCTGGTGAATTGACCTCAAATGGAAGACTGACTGCTCAGTTTGGTATAACCAGAAAGGACAG | CTTCCTGAATATCTCAGCATCCAT | ACCTAGTGATGTAGGCATCTACTTCTGTGCTGGGCAG |
| hTRAV36 | hTRAV36 | 164 | ATGATGAAGTTCCAAGCCTTTACTAGCTATCTTTTGGCTTCTACTAGCTGGGTGGGTGGAGCAGTGAAGACAAGGTGGTACAAAGCCCCTCTATCTCTGTTGTCCACGAGGAAGCACCGTAACTCTCAATTGCAGTATGAAGTGACTAACTTTCGAAGCCTACTATGGTACAAGCAGGATCCAGGAAAAGAAAGCTCCCACATTTCTATTTATGCTAACTTCAAGTGGAATTGAAAAGAAGTCAGGAGATCAGGAGACTAAGTAGCACATATTAGAATAAGAAGAACTTTCCAGCA | TCCTGAACATCAACAGCCACCCAG | ACCGAGACTCGGCCATCTACCTCTGTGCTGTGGAGG |
| hTRAV37 | hTRAV37 | 165 | ATGGAAACTCCACTGAGCACTCTGCTCTGCTCCTCTGTGCAGCTGACCTGGTCAAATGACAACTGCCAGTGGAACAGAATGCTCCTTCCCTGGAGAAGTCAAGGAAGGTGACAGCGTCACACTGAACTGCAGTTACGAGACAGCCCTTCAGATTCTTCAGTGGTTCAGGCAGGATCCTGAGGAAGGCCTCATTTCCCTGATACAAATGCTATCAACTGTGAGAGAAGATCAGTGGAAGATTCACAGCCACCAGGCTTAAAAAAGGAGACCAGCACATT | TCCCTGCACATACAGGATTCCCAG | CTCCATGACTCAACCACATTCTTCTGCGCAGCAAGCA |
| hTRAV38-1 | hTRAV38 | 166 | ATGACACGAGTTAGCTTGCTCTGTGGGCAGTCGTGCTTGGCTCTCCACCTGTCTTCACCCTGTCTTCTTGAATCCGGCATGGCCCAGACAGTCACTCAGTCTCAACCAGAGATGTCTGTGCAGGAGGCAGAGAGCTGTGAGACTGTGACCCTGAGTTGCACATATGACACCAGTGAGAATAATTATTATTTGTTCTGGTACAAGCAGCCTCCCAGCAGGCAGATGATTCTCGTTATTCGCCAAGAAGCTTATAAGCAACATGCAACGGAGAATCGTTTCTCTGAACTTCCAGAAAGCAGCCAAATCCTTCAGTCT | CAAGATCTCAGACTCCACAGCTGG | GGGACTGCCATGTATTTCTGTGCTTTCATGAAGCA |
| hTRAV38-2 | hTRAV38 | 167 | ATGGCATGCCCTGGCTTCCTGTGGGCACTGTGATCCTGTGGGCACTCTCCACCTGTCTCTTGAATTTAGCATGCCCAGACAGTCACTCAGTCTCAACCAGAGATGTCTGTGCAGGAGGCAGAGACCCTGAGCCTGAGCTGACCCTGAGCTGCACCTATGACACCAGTGAGAGTGATTATTATTTCTGGTACAAGCAGCCTCCTTCGCCAAGAAGCTTATAAGCAACAGATGCAACAGAGAATCGTTTTCTCTGAACTTCCGTAATCGCCGTTATTCGCCAAGAAGCAGCCAAATCCTTCAGTCT | CAAGATCTCAGACTCCACAGCTGG | GGGATGCCGGCATGTATTTCTGTGCTTATAGGAGCG |

TABLE 15-continued

TCR α chain V segments and binding sites for primers presented in Table 2 and Table 9. The sequence for each V segment presented in this table consists of three parts (listed from 5' to 3'): Sequence upstream of primer binding site, sequence of the primer binding site, sequence downstream of the primer binding site.

| V segment name | Primer name | SEQ ID NO | hTRAV sequence upstream of primer binding site | Primer binding site within hTRAV | hTRAV sequence downstream of primer binding site |
|---|---|---|---|---|---|
| hTRAV39 | hTRAV39 | 168 | ATGAAGAAGCTACTAGCAATGATTCTGTGGCTTCAACTAGACCGGTTAAGTGGAGAGCTGAAAGTGAACAAAACCCTCTGTTCCTGAGCATGCAGGAGGGAAAAAAACTATACCATCTACTGCAATTATTCAACCACTTCAGACAGACTGTATTGGTACAGGCAGGATCCTGGGAAAAGTCTGGAATCTCTGTTTGTTGCTATCAAATGGAGCAGTGAAGCAGGAGGGACGATTAATGCCCTCACTTGATACCAAAGC | CCGTCTCAGCACCCTCCACATCA | CAGCTGCCGTGCATGACCTCTGCCCACCTACTTCTGTGCCGTGGACA |
| hTRAV40 | hTRAV40 | 169 | ATGAACTCCTCTCTGGACTTTCTAATTCTGATCTTAATGTTTGGAGGAACCAGCAGCAATTCAGTCAAGCAGACGGGCCAAATAACCGTCTCGGAGGAGCATCTGTGACTATGAACTGCACATCCACCATCCACGGGTACCCTACCCTTTTCTGGTATGTGAATACCCCAGCAAACCTCTGCAGCTTCTTCAGAGAGACAATGGAAAAACAGCAAAAACTTCGGAGGCGAAATATTAAAGACAAAACTCCC | CCATTGTGAAATATTCAGTCCAGG | TATCAGACTCAGCCGTGTACTACTGTCTTCTGGGAGA |
| hTRAV41 | hTRAV10 | 170 | ATGGTGAAGATCCGGCAATTTTGTTGGCTATTTTGTGGCTTCAGCTAAGCTGTGTAAGTGCCGCCAAAAATGAAGTGAGCCAGAGTCCTCAGAACCTGACTGCCCAGGAAGGAGAATTATCACAATCAACTGCAGTTACTCGGTAGGAATAAGTGCCTTACACTGGCTGCAACAGCATCCAGGAGGAGCCATTGTTCCTGTTTATGCTGAGCTGCAGGGAAGAAGAAGCATGAAGATTAATTGCCACAATAAACATACAGGAAAAGCACAGCTCC | CTGCACATCACAGCCTCCCA | TCCCAGAGACTCTGCCGTCTACATCTGTGCTGTCAGA |

TABLE 16

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRbV | hTRbV sequence downstream of primer binding site |
|---|---|---|---|---|---|
| hTRBV01 | hTRBV01 | 171 | ATGGGCTGAAGTCTCCACTCTCCTGTGTCCATTGCTCTCCAGGCTTCTCCATGGATACTGGAATTACCCAGACACCAAAATACCTGGTCACAGCAATGGGAGTAAAAGGACAATGAAACGTGAGCATCTGGACATGATTCATGTATTGGTACAGACAGAAAGCTAAGAAACTCCCTGGAGTTCATGTTTTACTACAACTGTAAGGAATTCATTGAAAACAAGACTGTGCCAAATCACTTCACACCTGAATGCCCTGACAGCTCTCGCTTATACCTTCAT | GTGGTCGCACTGCAGCAAGAAGA | CTTCAGCTGCGTATCTCTGACCAGCAGCCAAGA |
| hTRBV02 | hTRBV02 | 172 | ATGGATACCTGGCTCGTCGTATGCTGGGCAATTTTAGTCTCTCTGAAAGCAGGACTCCACAGAACCTGAAGTCACCCAGACTCCCAGCCATGCACAGATGGGACAGGAAGTGATCTTCGCGTTGCCCATCTCTAATCACTTATACTTCTATTGGTACAGACAAATCTTGGGCAGAAGTGAATGCCTGTTTCCTTTTATATGAACTCTCAGAGAAGTCTGAAAATATTCGATGATCAATTCTCAGTTGAAAGGCCTGATGGATCAAATTTCACTCTGAA | GATCCGGTCCACAAAGCTGGAGGA | CTCAGCCATGTACTTCTGTGCCAGCAGTGAAGC |
| hTRBV03-1 | hTRBV03-1 | 173 | ATGGGCTGCAGGCTCCTCTTCTGTGTGGTCTTCCTGCCTCTCCAAGCAGTCCCTTGGACACAGCTGTTTCCCAGACTCCAAAATACCTGGTCACAGATGGGAAAACGACCAAGTCCATTAAATGTGAACAAAATCTGGCCATGGATACTCATGTATTGGTATAAACAGGACTCTAAGAAATTCTGAAGATAATGTTTAGCTACAATAATAAGGAGCTCATTATAAATGAAACAGTTCCAAATCGCTTCTCACCTAAATCTCCAGACAACGTCACTTAAATCTTCA | CATCAATTCCCTGGAGCTTGGTGA | CTCTGCTGTGTATTTCTGTGCCAGCAGCCAAGA |
| hTRBV03-2 | hTRBV03-2 | 174 | ATGGGCTGCAGGCTCCTCTGCTATGTGGCCTTCTGCCTCTGCAAGCAGGATCCACTGGACACAGCCGTTTCCAGACTCCAAAATACCTGGTCAAAATGGGAAAAAAGGAGTCTCTAAATGAGAACAAAATCTGGCCATAATGCTATGTATTGGTATAAACAGGACTCTAAGAAAGCACCAAGTCTTTGAAATGTGAACAACATAGACAGTTTTATCTACAGTAACAAGGAGCCAATTTTAAATGAAACAGTTCCAAATCGCTTCTCACCTCACCTGACTCTCCAGACAACGTCATTTAAATCTTCA | CATCAATTCCCTGGAGCTTGTGTGA | CTCTGCTGTGTATTTCTGTGCCAGCAGCCAAGA |
| hTRBV04-1 | hTRBV04-1 | 175 | ATGGGCTGCAGGCTGCTCTGCTGTGCGTTCTCTTCCTTGTCTCCTCTGGGAGCAGTTCCCATAGACACTGAAGTTACCCAGACACCAAAACACCTGGTCATGGGAATGACAAATAAGAAGTCTTTGAAATGTGAACAACATATGGGGCACAGGGCTATGTATTGGTACAAGCAGAAAGCTAAGAAAGCCACCGAGTTCCACAGACTCAAGCAAATGCTATCAACACAAACCTCTATAAATGAAAGTGTGCCAAGTCGCTTCTCACCTGAATGCCCCAACAGCTCTCTCTTAAACC | TTCACCTACACGCCCTGCAGCCAG | AAGACTCAGCCCTGTATCTCTGCCCAGCAGCCAAGA |
| hTRBV04-2 | hTRBV04-2 | 176 | ATGGGCTGCAGGCTGCTCTGCTGTGCGTTCTCTGTCCTTGTCTCCTCTGGGAGCCGGTCCCATGGAAACGGGAGTTACGCAGACACCAAGACACCTGGTCATGGGAATGACAAATAAGAAGTCTTTGAAATGTGAACAACATATGGGACTGGGCATAACGCTATGTATTGGTACAAGCAGAAAGCTAAGACACACCCTGCAGCCATCCTGGCCATGCTTCTCTACAACTTTAAAGAACAGACTGAAAACAACAGTGTGCCAAGTCGCTTCTCACCTGAATGCCCCAACAGCTCTCACTTATTCC | TTCACCTACACACCCTGCAGCCAG | AAGACTCGGCCCTGTATCTCTGTGCCAGCAGCCAAGA |
| hTRBV04-3 | hTRBV04-3 | 177 | ATGGGCTGCAGGCTGCTCTGCTGTGCGTTCTCTGTCCTTGTCTCCTCTGGGAGCCGGGTGAGTTGGTCCCCATGGAAACGGGAGTTACGCAGACACCAAGACACCTGGTCATGGGAATGACAAATAAGAAGTCTTTGAAATGTGAACAACATCTGGGTTACGCAGCAGACACCAAGACACCTATGATTGGTACAAGCAGAAGTGCTAAGAAGCCACTGGAGCTCATGTTTGTCTACAGTTCTTGAAGAACGGGTTGAAAACACCTGAATGCCCCAACAGCTCCTTACTCACTTATTCC | TTCACCTACACACCCTGCAGCCAG | AAGACTCGGCCCTGTATCTCTGCGCCAGCAGCCAAGA |
| hTRBV05-1 | hTRBV05-1 | 178 | ATGGGCTCCAGGCTGCTCTGTTGGGTGCTGCTTTGTCTCCTGGGAGCAGGCCCAGTAAAGGCTGGAGTCACTCAAACTCCAAGATATCTGATCAAAACGAGAGACAGCAAGTGACACTGACATGCACCCTTTATCCCCATCCCTGAATACTTCAGTGAGACACAGAGGAAAGGGTTGAGCACCTTGGACTGTGCCAAGTCGCTTCTGAATTCTCAGGGGCGCCAGTTCTCTCACTCTCTAACTCTCGCTCAGAT | GAATGTGAGCAACTTGGAGCTGG | GGGACTCGGCCCTTTATCTTTGCGCCAGCAGTTGG |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRbV | hTRbV sequence downstream of primer binding site |
|---|---|---|---|---|---|
| hTRBV05-2 | hTRBV05-2 | 179 | ATGGGCTCCCGGACTCCTCTGCTGACGCTGCTTTGTTCCTGGAGCAGGCCCAGTGGAGGCTGGAATCACCCAA GCTCCAAGACACCTGATCAAAACAAGAGACCAGCAAGTGACACTGAGATGCTCCCCTGGCCTCTGGCATAACTG TGTGTCCTGGTACCAACAAGCTCCAAGTCACGCCCCCTCCAGTTATTGTTACAATATTGTAATAGGTTACAAAGAGC AAAAGGAAACTTGCCTAATTGATTCTCAGCTGCCCATAACTAT | TACTGAGTC AAACACGGA GCTAGG | GGACTCAGCCCT GTATCTCTGTGC CAGCAACTTG |
| hTRBV05-3 | hTRBV05-3 | 180 | ATGGGCCCCCGGGCTCCTCTTGCTGACGCTGCTTTATCTCCTGGAACTGCTTTATCTCCTGGAGCAGGCCCAGTGGAGGCTGGAGTCACCCAA AGTCCCACACACCTGATCAAAACAGAGAGACCAGCAAGTGACACTGAGATGCTCGAGATGCTCCTATCTCTGGGACACAGCAG TGTGTCCTGTGTACCAACAGGCCCCGGGTCAGGGGCCCAGTTTATCTTTGAATATGCTAATGAGTTAAGGAGATC AGAAGGAAACTTCCCTAATCGATTCTCAGGGCGCCAGTTCCATGACTGTT | GCTCTGAGA TGAATGTGA GTGCCT | TGGAGCTGGGG ACTCGGCCCTGT ATCTCTGTGCCA GAAGCTTGG |
| hTRBV05-4 | hTRBV05-4 | 181 | ATGGGCCCCTGGGCTCCTCTTGCTGTCTCTCTGGGAGCAGGCTCAGTGGAGACTGGAGTCACCCAA AGTCCCACACACCTGATCAAAACAGAGAGACCAGCAAGTGACTGAGATGCTCTTCCAGTGTCGGGCACAACAC TGTGTCCTGGTACCAACAGGCCCTGGGTCAGGGGCCCCAGTTTATCTTTCAGTATTATAGGGAGGAAGAGAATGG CAGAGGAAACTTCCCTAGATTCTCAGTCTCCAGTTCCCTAATTATAGCT | CTGAGCTGA ATGTGAACG CCTT | GGAGCTGGACGA CTCGGCCCTGTA TCTCTGTGCCAG CAGCTTGG |
| hTRBV05-4 | hTRBV05-5 | 182 | ATGGGCCCCTGGGCTCCTCTTGCTGTCTCTCTGGGAGCAGGCCCAGTGGACGCTGGAGTCACCCAA AGTCCCACACACCTGATCAAAACAGAGAGACAGCAAGTGACTCTCCTATCTCTGGGCACAGCAGAG TGTGTCCTGTGTACCAACAGGTCCTGGGTCAGGGGCCCCAGTTTATCTTTCAGTATTATCGAGAAAGAAGAGAG GAAGAGGAAACTTCCCTGATCGATTCTCAGCTGCCAGTCTCAGCTCCCTAACTATAGCT | CTGAGCTGA ATGTGAACG CCTT | GTTGCTGGGGA CTCGGCCCTGTA TCTCTGTGCCAG CAGCTTGG |
| hTRBV05-6 | hTRBV05-6 | 183 | ATGGGCCCCCGGGCTCCTCTTGCTGTCTCTCTGGGCACTGCTTTGTCTCCTGGAGCAGGCCCAGTCGGTGGACGCTGGAGTCACCCAA AGTCCCACACACCTGATCAAAACAGAGGACGACCAAGTGACTCTCTCCAAGCTCGGGCATGACAC TGTGTCTGGTACCAACAGGCCCTGGGTCAGGGGCCCCAGTTTATCTTTCAGTATTATGAGGAGAAGAAGAGAC AGAGAGGAAACTTCCCTGATCGATTCTCAGGCTGCCAGTCTCAGCTCCCTAACTATAGCT | CTGAGCTGA ATGTGAACG CCTT | GTTGCTGGGGA CTCGGCCCTCTA TCTCTGTGCCAG CAGCTTGG |
| hTRBV05-7 | hTRBV05-7 | 184 | ATGGGCCCCCGGGCTCCTCTTGCTGTCTCTCTGGGCACTGCTTTGTCCCCCTAGGAGAAGGCCCAGTGGACGCTGGAGTCACCCAA AGTCCCACACACCTGATCAAAACAGAGGACAGCAAGTGACTCTCGAGATGCTCCTATCTCTGGGCACACCAG TGTGTCCTGTGTACCAACAGGCCCTGGGTCTCAGGGGCCCCAGTTTATCTTTCAGTATTATGAGAAAGAAGAGAGAG GAAGAGGAAACTTCCCTGATCAATTCTCAGGTCACCCAGTTCCCTAACTATAGCT | CTGAGCTGA ATGTGAACG CCTT | GTTGCTAGGGGA CTCGGCCCTCTA TCTCTGTGCCAG CAGCTTGG |
| hTRBV05-8 | hTRBV05-8 | 185 | ATGGGACCCAGGCTCCTCTCTTCTGGGCACTGCTTTGTCTCCTGGAACAGGCCCAGTGGAGGCTGGAGTCACACAA AGTCCACACACACCTGATCAAAACAGAGAGACAAGCAAGTGACTCTCGAGATGCTCCTATCTCTGGGCACACCAG TGTGTACTGGTACCAACAGGCCCTGGGTCTGGGCCTCCAGTTTCTCCTTGGTATGACAGGGGTGAAGAGAGAAA CAGAGGAAACTTCCCTAGATTTTCAGTCTCCAGTTCCCTAATTATAGCT | CTGAGCTGA ATGTGAACG CCTT | GGAGCTGAGGA CTCGGCCCTGTA TCTCTGTGCCAG CAGCTTGG |
| hTRBV06-1 | hTRBV06-1 | 186 | ATGAGCATCGGGCTCCTGTGTTGTGTGAAGACAGCAGAGAGAGCATGAACACTGCAGTCAGTGCCCAGGATATGAACCATAACTC CATGTACTGGTATCGACAAGACCCAGGCATGGGACTGAGGCTGATTCATTACTCAGTTGAGGGTACCACTGA CAAAGGAGAAGTCCCCATGCTACAAATGCTCCAGATTCTCCAGATTAAACAAACGG | GAGTTCTCG CTCAGGCTG GAGT | CGGCTGCTCCCT CCAGACATCTG TGTACTTCTGTGC CAGCAGTGAAGC |
| hTRBV06-2 | hTRBV06-2 | 187 | ATGAGCCTCGGGCTCCTGTGCTGTGTGGCCCTTTCTCTCCTGTGGGCAGGTCCAGTGAATGCTGGTGTCACTCAG ACCCCAAAATTCCGGGTCCTGAAGACAGGAAAGCAGACCATGACACTGCTGTGTGCCCAGGATATGAACCATGAATA CATGTACTGGTATCGACAAGACCCAGGCATGGGACTGCGATTGATTACTATCCAGATGTGGTGAGGGTACAACTG CCTCCCAAGGAGCTGCAGATTCTCCAGATTAAAAAACAGAATTTCCTG | CTGGGGTTG GAGTCGGCT GTC | CCTCCAAACAT CTGTGTACTTCTG TGCCAGCAGTTA CTC |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRBV | hTRBV sequence downstream of primer binding site |
|---|---|---|---|---|---|
| hTRBV06-3 | hTRBV06-2 | 188 | ATGAGCCTCGGGCTCCTGTGCTGTGTGGGGCCTTTTCTCCTCCTGTGGGCAGTCCAGTGAATGCTGTGTCACTCAG ACCCAAAATTCCGGGTCCTGAAGACCACAGGACAGAGCATGACACTGCTGTGTGCCAGGATATGAACCATGAATA CATGTACTGGTATCGACAAGACCCAGGCATGGGCTGAGGCTGATTCATTACTCAGTTGGTGAGGGTACAACTG CCAAGGAGAGGTCCCTGATGGCTACAAATGTCTCCAGATTAAAAACAGAATTCCTG | CTGGGGTTG GAGTGGCT GCTC | CCTCCCAAACAT CTGTGTACTTCTG TGCCAGCAGTTA CTC |
| hTRBV06-4 | hTRBV06-4 | 189 | ATGAGAATCAGGCTCCTCTGTCTGTGGCCTTTCTCTCTCCTGTGGGCAGTCCAGTGAATCCTGGGATCACCCAG GCACCAACATCTCAGATCCTGCAGCAGCGACGGCCCATGACACTGCAGTGTGCCCAGGATATGAGACATAATGC CATGTACTGGTATAGACAAGATCTAGGACTGGGCCTAAGGCTCATCCATTATTCAAATACTCAGGTACCACTGG CAAAGGAGAAGTCCCTGATGTTATAGTGTCTCCAGAGCAAACACAGATGATTTC | CCCCTCACG TTGGCGTCT GCTG | TACCCTCAGA CATCTGTGTACTT CTGTGCCAGCAG TGACTC |
| hTRBV06-5 | hTRBV06-5 | 190 | ATGAGCATCGGCCTCCTGTGTCAGCCTTGTCTCTCTGTGGGCAGTCCAGTGAATGCTGGTGTCACTCAG ACCCAAAATTCCAGGTCCTGAAGACACAGAGACATGAGCATGCAGTGTGCCCAGGATATGAACCATGAATA CATGTCCTGGTATCGACAAGACCCAGGCATGGGGCTGATTCATTACTCAGTTGGTGTGTATCACTGA CCGAGGAGAGTCCCTGATGGCTACAAATGTCTCCAGATCTCCAGAGAGATT | TCCCGCTCA GGCTGCTGT CGGC | TGCTCCCTCCCA GACATCTGTGTA CTTCTGTGCCAG CAGTTACTC |
| hTRBV06-6 | hTRBV06-6 | 191 | ATGAGCATCAGCCTCCTGTGCAGCCTTCCTGTGTCAGCCTTCCTCTCTGTGGGCAGTCCAGTGAATGCTGGTGTCACTCAG ACCCAAAATTCCGATCCTGAAGATTAGGACAGAGACATGAGCATGCAGTGTACCCAGGATATGAACCATAACTA CATGTACTGGTATCGACAAGACCCAGGCATGGGTGAAGCTGATTTATTATCAGTTGGTGTCGGTATCACTGA TAAAGGAGAAGTCCCAGGCTACAACGTCTCCAGATCTCCAGAGAG | GATTTCCCG CTCAGGCTG GAGT | TGGCTGCTCCCT CCCAGACATCTG TGTACTTCTGTGC CAGCAGTTACTC |
| hTRBV06-7 | hTRBV06-7 | 192 | ATGAGCATCAGCCTCCTGTGTGTCAGCCTTCCTCTCTGTGTGGGGCAGTCCAGTGAATGCTGGTGTCACTCAGA CCCCAAAATTCCACTGTCCTGAAGACAGGAGCATGACACTGCTGTGTGCCCAGGATATGAACCATCAGATCCTC ATGTATCGGTATCGACAAGACCCAGGCAAGGGCCTCCAGGAGGTGATTTACTACTCAGTTGCTGCTGCTCCACTGAC AAAGGAGAAGTTCCCAATGGCTACAAATGTCTCCAGATCAAACACAGAGATT | TCCCCTCA AGTGGAGT CAGCT | GCTCCCTCTCAG ACTTCTGTTACT TCTGTGCCAGCA GTTACTC |
| hTRBV06-8 | hTRBV06-8 | 193 | ATGAGCCTCGGGCTCCTGTGCGCCTTCCTCTCTGTGGGCAGTCCAGTGAATGCTGGTGTCACTCAGA CCCCAAAATTCCACATTCCTGAAGACAGAGCATGAGCACTGCAGTGTGCCCAGGATATGAACCATGGATAC AATGTCCTGGTATCGACAAGACCCAGGCATGGGGCTGAGACTGATTTACTACTCCAGCTGCTGCTGTACTACTGAC AAAGGAGAAGTCCTACAATGGCTACAAATGTCTCCAGATTAAACACAGAGATT | TCCCACTCA GGCTGGTGT CGGC | TGCTCCCTCCCA GACATCTGTGTA CTTGTGTGCCAG CAGTTACTC |
| hTRBV06-9 | hTRBV06-6 | 194 | ATGAGCATCGGGCTCCTGTGTGCTGTGGAGGGTCCAGTGAATGCTGTGTCACTCAG ACCCCAAAATTCCAGGTATCGACAAGACCCAGGCATGGGCTGAGGCTGATTCATTACTCAGTTGCTGCTGTATCACTGA CTTGTCCTGGTATCGACAAGACCCAGGCATGGGGCCATTCATTACTCAGTTGCTGCTGTATCACTGA CAAAGGAGAAGTCCCTGATGGCTACAAATGTCTCCAGATATCCAGATCAAACACAGAG | GATTTCCCG CTCAGGCTG GAGT | CAGCTGCTCCCT CCCAGACATCTG TATACTTCTGTGC CAGCAGTTATTC |
| hTRBV07-1 | hTRBV07-1 | 195 | ATGGGCACAAGGCTCCTCTTCTGCTGCTGGGCCAGCAGATCACAGCCATATGTCTCCTGGGCAGATCACACAGGTGCTGGAGTCTCCCA GTCCCTGAGACACAAGGTAGCACAAGAAAGGATGTAGCTCAGATATGATTACTTCCAGGCAAGGATGCCAGCAG CCCTTTATTGGTACCGACAGAGCCTGGGGCAGGGCCTGGAGTTTCCAATTTTACTTCTGACAGAGCTGAGGGATT ACAATCGGGCTTCCCGTTCTCGTCGACAGAGGTCTGAGGGATCCATTCA | CTCTGAAGT TCCAGCGCA CACA | GCAGGGGACTT GGCTGTGTATCT CTGTGCCAGCAG CTCAGC |
| hTRBV07-2 | hTRBV07-2 | 196 | ATGGGCACCAGGCTCCTCTTCTGGGTGGCCTTCTGTCTCCTGGGGCAGATCACACAACCAGGAGCTGGAGTCTCCCAG CATGACCCCAGTAACAAGGTCTACAAGAGGAAGGAGAGGAAGGATGAGCTCAGGTGATCAATTTCAGTCATCTGC CCTTTACTGGTACCGACAGACCTGCCCAGGAACGGGGGCTGGAGTTTTTAAATCTACTCCAAGGCACAGTGACCAGA CAAATCAGGGCTGCCCAGTGATCGTTTCTGCAGAGAGACTGGGGATCTCCACTCTGAC | GATCCAGCG CACACAGCA GGAG | GACTCGGCCGTG TATCTCTGTGCC AGCAGCTTAGC |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRbV | hTRbV sequence downstream of primer binding site |
|---|---|---|---|---|---|
| hTRBV07-3 | hTRBV07-5 | 197 | ATGGGCACCAGGCTCCTCTTCTGCTGGGCCCTGTGCCTCCTGGGCAGATCACACAGGTCTGAGTCTCCCAG ACCCCAGTAACAAGGTCACAGAGAAGGGAAAAATATGCAGGTGATCCAATTTAGAGCTCCAGGTGTATCTGC CCTTTACTGGTACCCGACAAAGCTCGGGCAGGGCCCCAGAGTTTCTAATTTACTTCCAAGGCACGGGTGCGGCAG CGACTCAGGGCTGCCAACGATCGGTTCTTTGACCTCAGCCTGAGGGATCCGTTCT | ACTCTGAAG ATCCAGCGC ACAGA | GCGGGGGACTC AGCCGTGTATCT CTGTGCCAGCAG CTTAAC |
| hTRBV07-4 | hTRBV07-5 | 198 | ATGGGCACCAGGCTCCTCTTCTGCTGGTGGTCCTGGGTTTCCTAGGGACAGATCACACAGGTCTGAGTCTCCCAG TCCCAAGGTACAAAGTCGCAAAGAGGGACGGGATGTAGCTCTCAGGTGTGATTCAATTTCGGGTCATGTAAC CCTTTATTGGTACCGACACAGACCCTGGGCAGGGCTCAGAGGTTCTGACTTACTCCAGAGTGATGCTCAACGAGA CAAATCAGGGCGCGCCCAGTGGTCGGTTCTTCTGCAGAGAGCCTGAGAGATCCGTCTCC | ACTCTGAAG ATCCAGCGC ACAGA | GCAGGGGACTC AGCTGTGTATCT CTGTGCCAGCAG CTTAGC |
| hTRBV07-5 | hTRBV07-5 | 199 | ATGGGCACCAGGCTCCTCTTCTGCTGGTGGTCCTGGGTTTCCTAGGGACAGATCACACAGGTCTGAGTCTCCCAG TCCCAAGGTACGAAGTCACACAGAGGGACAGATGTAGCTCCCAGGTGTGATCCAATTTCGGGTCAGGTAAC CCTTTATTGGTACCGACAGGGCCTGGGCAGGGTTCTGACTTCCTTCCAGATGAACTTCAACAAGA TAAATCAGGGCTGCTGCAGTGATCAATTCTCCACAGAGAGTCTGAGAGATCTTCTCCACCTGA | AGATCCAGC GCACAGAGC AAGG | GCCACTCCGCTG TGTATCTCTGTGC CAGAAGCTTAG |
| hTRBV07-6 | hTRBV07-6 | 200 | ATGGGCACCAGTCTCCTATGCTGGGTGTCTCTGGGTTCCTAGGGACAGATCACACAGGTCTGAGTCTCCCAG TCTCCAGGTACAAAGTCACAAAAGAGGGACAGGATGTAGCTCTCAGGTGTCATCAATTCGGGTATCC CTTTATTGGTACCGACAGCCTGGGCAGGGGCCCAGAGTTTCTGACTTATTCTGAACAACACTATGAAGCCCAACAAGAC AAATCAGGGGCTGCCCAATGATCGGTTCTCTGCAGAGAGGCCTGAGGATCCATCTCCACTCTGACGATC | CAGCGCACA GAGCAGCGG GACT | CGGCCATGTATC GCTGTGCCAGCA GCTTAGC |
| hTRBV07-7 | hTRBV07-6 | 201 | ATGGGTACCAGTCTCCTATGCTGGGTGTCTCTGGGTTCCTAGGGACAGATCACACAGGTCTGAGTCTCCCAG TCTCCAAGGTACAAGTCACAAAAGAGGGACAGGAGGACAGGATGTAGCTCTCAGGTGTGATCCAATTTCGGGTCATGCAAC CCTTTATTGTATCAACAGCCCTGGGCAGGCCCAGATTTCTGACTTACTTCAATTATGAAGCTCAACAGA CAAATCAGGGCTGCCCAGTGATCGGTTCTTCTGCAGAGAGCCTGAGGGATCCATCTCCACTCTGACGATT | CAGCGCACA GAGCGCGG GACT | CAGCCATGTATC GCTGTGCCAGCA GCTTAGC |
| hTRBV07-8 | hTRBV07-2 | 202 | ATGGGCACCAGGCTCCTCTTCTGCTGGTGTCCTGGGTTTCCTAGGACAGATCACACAGGTCTGAGTCTCCCAG TCCCTAGGTACAAAGTCGCAAAGAGGAGACAGGATGTAGCTCTCAGGTGATCCAATTTCGGGTCATGTATCC CTTTTTGGTACCAACAGGCCCTGGGCAGGGCCCAGAGTTTCTGACTTTCTCAGAATGAAGCTCAACTAGAC AAATCGGGGCTGCCCAGTGATCGCTTCTTGCAAAGAGCCTGAGGGATCCGTCTCCACTCTGAA | GATCCAGCG CACACAGCA GGAG | GACTCCCCGTG TATCTCTGTGCC AGCAGCTTAGC |
| hTRBV07-9 | hTRBV07-9 | 203 | ATGGGCACCAGGCTCCTCTGTGATGAGCCCCTGTCTCTGGGTCAGATACGACAGATCTGAGTCTCCCAG AACCCCAGACACAAGATCACACAGACCCTGGGCAGGGGACAGAGAATGTAACTTTCAGGTGTGATCCAATTTCCGAGAACAACCG CCTTTATTGGTACCGACAGGCCCTGGGCAGGGACGTTCTCTGCAGAGAGTTCTGACTTACTTCCAGAATGAAGCTCAACTAGA AAAATCAAGGCTGCTCAGTCGGTTCTCTGCAGAGAGCCTAAGGGATCTTTTCCACCTG | GAGATCCAG CGCACAGAG CAGG | GGGACTCGGCCA TGTATCTCTGTGC CAGCAGCTTAGC |
| hTRBV08-1 | hTRBV08-1 | 204 | GAGGCAGGATCAGCCAGATACCAAGATACACAGATATCACAGACACAGAGGGAAAAAGATCATCCTGAAATATGCTCAGA TTAGGAACCATTATTCAGTGTTCTGTTATCAATAAGACCAAGAATAGGGGCTGAGGCTGATCATTATTCAGGTA GTATTGGCAGCATGACCATGACAAAGGGCCGTTGCCAAGGATACAATGTCTCTGGAAACAAGCTCAAGCATTTT | CCCTCAACC CTGAGTCT ACTA | GCACCAGCCAGA CCTCTGTACCTCT GTGGCAGTGCAT |
| hTRBV08-2 | hTRBV08-2 | 205 | ATGAACCCCAAACTCTTCTGTGTGACCCTTTGTCTCCTGGGGACGTCTCTATTGATGCTGGATCACCCAGATG CCAAGATATCACATTGTACAGAAAGAAGAGATGATCTCGGAATGTGCTCAGGTTAGGAACAGTGTTCTGATATC GACGAGCCAAGACGGGGCCGAAGCTTATCCACTATTCAGGCAGTGGTCACGCAGGAAGGCGAGGAAGGTCAAGCATC ACAGAGGGGTACTGTGTTTCTTGAAACAAGCTTGAGCAT | TCCCCAATC CTGGCATCC ACCA | GCACCAGCCAGA CCTATCTGTACC ACTGTGCCAGCA CATC |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRBV | hTRbV sequence downstream of primer binding site |
|---|---|---|---|---|---|
| hTRBV09 | hTRBV09 | 206 | ATGGGCTTCAGGCTCCTCTGCTGTGTGGCCTTTTGTCTCCTGGAGCAGGCCCAGTGGATTCTGGAGTCACACAAACCCCAAAGCACCTGATCACAGCACTGGACAGCAGTGAGATGCTCCCTAGGTCTGAGACCTCTGTGTACTGGTACCAACAGAGCCTGGACCAGGGCCTCCAGTTCCTCATTCAGTATTATAATGGAGAAGAGAGAGCAAAAGGAAACATTCTTGAACGATTCTCCGCACAACAGTTCCCTGACTTGCACTCTGAA | CTAAACCTG AGCTCTCTG GAGCT | GGGGGACTCAGC TTTGTATTTCTGT GCCAGCAGCGTA G |
| hTRBV10-1 | hTRBV10-1 | 207 | ATGGGCACAGAGGCTCTCTTCTTCTATGGTGTGTCTCTGCTGGCAGCACAGGATGTCGAAATCACCCAGAGCCCAAGACACAGATCACAGAGACAGGAAGGACAGCAATGCCTCGTGTGACCTTGGCTGATCACCAGACTTGGAACACCAACAATATGTTCTGGTATCGACAAGACCTCAGATGGCTACAGTGTCTCTAGATGAAACACAGAGGACCTCCACAAAGGAGAAGCTTCAGATGGCTACAGTGTCTCTAGATGAA | CCCTCACTC TGGAGTCTG CTGC | CTCCTCCCAGAC ATCTGTATATTTC TGCGCCAGCAGT GAGTC |
| hTRBV10-2 | hTRBV10-2 | 208 | ATGGGCACCAGGCTCCTCTTCTTCTATGGTGGCCCTTTGTCTCTGTGTGGCAGCAGGATGCCTGGAATCACCCAGAGCCCAAGATACAAGATCACAGAGACAGGAAGGACAGGCAGTGACCTTGATGTGTCACCAGACTTGGAGCCCAGCTATATGTTCTGGTATCGACAAGACCTGGGAGCATGGCTGAGCTGATCTATTACTCAGCAGCTGCTGATATTACAGATAAGGAGAAGCTCCCAGATGGCTATGTTGTTCTCCAAGATCCAAGACAGAGATTTCC | CCCTCACTC TGGAGTCAG CTAC | CCCCTCCCAGAC ATCTGTGTATTTC TGCGCCAGCAGT GAGTC |
| hTRBV10-3 | hTRBV10-3 | 209 | ATGGGCACAAGGTTGTCTTTCTATGTGGCCCTTTGTCTCCTGTGGACAGGACAGGACACATGGATGCTGGAATCACCCAGAGCCCAAGACACAAGATCACAGAACACAGTGACTCTGAGATGTCACCAGACTGAAGATGAGTGCAGCTATATGTACTGGTATCGACAAGACCCGGGGCATGGGCTGAGGCTGATTCATTACTCCATTACTCATATGGTGTTAAAGATACTGACAAAGGAGAAGTCTCAGATGGCTATAGTGTCTCTAGATGAAGACAGAGAGAGATTCC | TCCTCACTC TGGAGTCCG CTAC | CAGCTCCCAGAC ATCTGTGTACTTC TGTGCCATCAGT GAGTC |
| hTRBV11-1 | hTRBV11-1 | 210 | ATGAGCACCAGGCTTCTCTGCTGTGTGGCCCTTTGTCTCCTGGGAGCAGAACTCTCAAGAAGCTGAAGTTGCCCAGTCCCCCAGATATAAGATTACAGAGAAAAGCCAGGCTGTGACTCTGGATTGTACTCCTATATCGACAAGACTTGGTGATCAATCCTATATTCAATTTCAAAGTACCTGCTTTACTGGTACCGACAGGCCCTGGGGCTCTGGGCCTATGAACACTCCCTAGATCGATTCTCCATTCGCTGATATCAATTGCAAAGAGAAGTAGACT | CCACTCTCA AGATCCAGC CTGCA | AAGCTTGAGGAC TCGGCCGTGTAT CTCTGTGCCAGC AGCTTAGC |
| hTRBV11-2 | hTRBV11-2 | 211 | ATGGGCACCAGGCTCCTCTTCTTCTATGGTTCTCTGCTGGCGCCCCTTTGTCTCCTGGGAGCAGAACTCACAGAAGCTGAGTTGCCCAGTCCCCCAGATATAAGATTATAGAGAAAAGGCAGACAGTGACTCTGAGATGCCAATCCTATCGACCCATGCTACCTTTACTGGTACCAGCAGATCCTGGGACAGGGCCCAAAGCTTCTGATTCAGTTTCAGAATAACCGTGTAGTGGATGAATTCACAGTTGCCTAAGGATCGATTCTCCCGCAGAGGCTCAAAAGGAGTAGACT | CCACTCTCA AGATCCAGC CTGCA | GAGCTTGAGGAC TCGGCCGTGTAT CTCTGTGCCAGC AGCTTAGA |
| hTRBV11-3 | hTRBV11-3 | 212 | ATGGGTACCAGGCTCCTCTTCTGTGGCCTTCTCCTTCTCCTTCCTCCTCCCTGTGAAGAAGACTCTATAGAAGAACTCATAGAAGAACTGAAGAAGTCTGCCAACATACCCTTTACTGGTACCGACAGATCCTGGGACAACTTGGGACAGGGCCCAAAACAGCGCCCAGCTTCTGATTCAGTTTCTGATTCGATATCGATTATCGATATCGAGAATGAGAAGCAGTAGACTGATTCACAGTTGCCTAAGGATCGATTCTCCGCAGAGGCTCAAAAGGAGTAGACT | CCACTCTCA AGATCCAGC CTGCA | GAGCTTGGGGAC TCGGCCGTGTAT CTCTGTGCCAGC AGCTTAGA |
| hTRBV12-1 | hTRBV12-1 | 213 | ATGGGCTCTTGGACCCTCTGTGTGTCCCTTTATCCTGGTAGCGACACACACAGAGATGGCCGTGGTTATCCAGTCACCCAGCACAAAGTGACAGAGATGGGAGATGACAGATGAACCAATTTCAGGCCACACAATGATCTTCTCTGGTACAGAGACCTTTGTGCCAGGGGACAACAACTACTTCTGCAGCTGGAATTGCTGATTGGAACAATTGCTGATTGAATTGCTGATTGCTGATTCATTCCACCTCTCTCAAGGAGTGTCCAAAGGAATTGCTTCTCCTCCAGGATTGCTGATTGCTGATTGCTGATTGCTGATTGCTGATTGCTGATTGCTGATTGCTGATTGCTGATTGCTGATTGCTGATT | GAGGATCCA GCCCATGGA ACCCA | GGGACTTGGGCC TATATTTCTGTGC CAGCAGCTTTGC |
| hTRBV12-2 | hTRBV12-2 | 214 | ATGGACTCCTGGACCCTCTGTGTCCCTTTGTATCCTGGTAGCCAGATCAGCTGCAGATGCTGGCATTATCCAGTCACCCAAGCATGGAGTGACAGAAATGGGACAAAATGTGACTCTGAGATGTGAGCCAATTTTCTGGACAATGTACTCCGGAATGTGAGTTACTTCCGGAGCTGTCTATTATAAGATAATGCAGGGTATGCCCACAGAGCGATTCTCAGCTAGCAGCTGATGATTCATTCTCAGCTAGCGATGAACTAGAGACTCATGAAGGCTCGATGATCATTCTACT | CTGAAGATC CAGCCTGCA GAGC | AGGGGGACTCGG CCGTGTATGTCT GTGCAAGTCGCT TAGC |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRbV | hTRbV sequence downstream of primer binding site |
|---|---|---|---|---|---|
| hTRBV12-3 | hTRBV12-3 | 215 | ATGGACTCCTGGACCTTCTGCTGTGTGTCCCTTTGCATCCTGGTAGCGAAGCATACAGATGCTGAGTTATCCAG TCACCCCGCCATGAGTGACAAGAGTGGGACAAGAGTGACTCTGAGATGTAAACCAATTTCAGCCACTC CCTTTTCTGGTACAGACAGACCATGATGCGGGGGACTGGAGTTGCTCATTTACTTTAACAACACGTTCCGATAGA TGATTCAGGGATGCCCGAGGATCGATTCTCAGCTAAGATGCCTAATGCATCATTCTCCACTCTGAAGATC | CAGCCCTCA GAACCCAGG GACT | CAGCTGTGTACT TCTGTGCCAGCA GTTTAGC |
| hTRBV12-4 | hTRBV12-4 | 216 | ATGGGCTCCTGGACCCTCTGCTGTGTGTCCCTTTGCATCCTGGTAGCAAAGCACACAGATGCTGAGTTATCCAG TCACCCCGGCACGAGGTGACAGAGATGGGACAAGAGTGACTCTGAGATGTAAACCAATTTCAGGACACACTA CCTTTTCTGTGTACAGACAGACCATGATGCGGGGACTGGAGTTGCTCATTTACTTTAACAACACGTTCCGATAGA TGATTCAGGGATGCCCGAGGATCGATTCTCAGCTAAGATGCCTAATGCATCATTCTCCACTCTGAAGATC | CAGCCCTCA GAACCCAGG GACT | CAGCTGTGTACT TCTGTGCCAGCA GTTTAGC |
| hTRBV12-5 | hTRBV12-5 | 217 | ATGGCCACCAGGCTCCTCTGCTGTGTTCTTTTGTTCTCCTGGAGAAGAGCTTATAGATGCTAGAGTCACCCAG ACACCAAGGCACAAGGTGACAGAGATGGACAAGAAGTAACAATGAGATGTCAGCCAATTTTAGGCCACAATA CTGTTTTCTGGTACAGACAGACCATGATGCAAGGACTGGAGTTGCTGGCTTACTTCCGCAACCGGCTCCTAG ATGATTCGGGGATGCGCGAAGGATCGATTCTCAGCAGAGATGCCTGATGCAACTTTAGCCACTCTGAAGATC | CAGCCCTCA GAACCCAGG GACT | CAGCTGTGTATT TTTGTGCTAGTG GTTTGGT |
| hTRBV13 | hTRBV13 | 218 | ATGCTTAGTCCTGACCTGCTCCTCAGTTTAGTGTCCTCAGCAGCCTCCTGTCCCATGTCATGCTTTGTCTCCTGGAG CAGTTTCAGTGGCTGGAGTCATCAAGGTCCCCAAGACATCTGAATCAAAGAAAACAGCGAAACAGCCACTCTG AAATGCTATCCTATCCTACGAGACCACACAGGTCTACTGGTACAAAATCCCAGGTTCCTC ATTTCGTTTTATGAAAAGATGCAGAGCGATAAAGGAAGCATCCCTCAGCTGACTTCAGCAGTTCAGTGAC TATCATTCTGAACTGAACAT | GAGCTCCTT GGAGCTGGG GGACT | CAGCCCTGTACT TCTGTGCCAGCA GCTTAGG |
| hTRBV14 | hTRBV14 | 219 | ATGGTTTCCAGGCTTCTCAGTTTAGTGTCCCTTTGTCCCCTTTGTCTCCTGGAGCAAGCACATAGAAGCTGAGTTACTCAG TTCCCAGCCACAGCTAATAGAGAAGGGCAGCTGTGACTCTGAGATGTGACCATTTCTGACATGATAA TCTTTATTGGTATCGACGTGTATGGGAAAAGAAATAAATTCTGTTACATTTTTGTGAAAGAGTCTAAACAGGA TGAGTCCGGTATGCCAACAATCGATTCTTAGCTGAAGGACTGAGGGACGTATTCTACTCTGAA | GGTGCAGCC TGCAGAACT GGAG | GATTCTGGAGTT TATTTCTGTGCCA GCAGCCAAGA |
| hTRBV15 | hTRBV15 | 220 | ATGGGTCCTCGGGCTTCTCACTGGATACCCAGTTTGGAAAGCCAGTGACCCTGAGTTGTTCTCAGATTTGAACCATAAGCTC ATGTACTGGTACCAGCAGAAGTCAAGTCAGGCCCCCAAGCTCTGTTCCACTACTATGACAAGATTTTAACAAT GAAGCAGACACCCCTGATAACTTCCAATCCAGGAGGCCGAAACACTTCTTTCTGCTTCTT | GACATCCGC TCACCAGGC CTGG | GGGACACAGCCA TGTACTTGTGTG CCACCAGCAGAG A |
| hTRBV16 | hTRBV16 | 221 | ATGAGCCCAATATTCACCTGCATCACAATCCTTTCTGCTGCTGCAGGTTCTCCTGGTGAAGAAGTCGCCAG ACTCCAAAACATCTTGTCAGAGGGAAGACAGAAGCAAATATATGTGCCCAATAAAGGACACAGTTA TGTTTTTGTACCAACAGGTCCTGAAAAACGAGTTCAAGTTCTTGATTCCTTCCAGAATGAATAAGTCTTTGAT GAACAGGTATGCCCAAGGAAGATTTTCAGCTAAGTGCCTCCCAAATTCACCCTGAGCCT | TGAGATCCA GGCTACGAA GCTT | GAGGATTCAGCA GTGTATTTTTGTG CCAGCAGCCAAT C |
| hTRBV17 | hTRBV17 | 222 | ATGGATATCTGGCTCCTCTGCTGGGTGACCCTGTCTCTTGGCGGCAGGACACTCGGAGCCTGAGTCAGCAG ACCCCAGACACAAGGTCACCAACATGGAGCAGGAGGTGATTCTGAGGTGCCATCCATTCTTCGTTCATGTTT GTTCACTGGTACCAGCAGATCTGAGGCAAGAAATGAAGTTGCTGATTTCCTTCCAGTACCAAAACATTGCAGTT GATTCAGGGATGCCCAAGGACGATTCACAGCTGAAAGACCTAACGAAGACCTCTTCCACGCT | GAAGATCCA TCCCGCAGA GCCG | AGGGACTCAGCC GTGTATCTCTAC AGTAGCGGTGG |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRBV | hTRbV sequence downstream of primer binding site |
|---|---|---|---|---|---|
| hTRBV18 | hTRBV18 | 223 | ATGGACACCAGAGTACTCTGCTGTGCGTCATCTGTCTTCTGGGGCAGTCTCTCAAATGCCGCGTCATGCAG AACCCAAGACACCTGTCAGGAGGGGACAGGATGCAGGATGTCGAGATGCCAATGAAAGACACAGTC ATGTTACTGGTATCGGCAGCTCCCAGAGGAAGTCTGAAATTCATGGTTTATCTCCAGAAAGAAAATCATAG ATGAGTCAGAATGCCAAAGGAACGATTTCTGCTGAATTCTCCAAAGAGGGCCCAGCATCCTGA | GGATCCAGC AGGTAGTGC GAGG | AGATTCGGCAGC TTATTCTGTGCC AGCTCACCACC |
| hTRBV19 | hTRBV19 | 224 | ATGAGCAACCAGGTGCTCTGCTGTGTGGTCCTTTGTTCTCTGGAGCAAACACCTGGATGGTGAATCACTCAG TCCCAAAGTACCTCTTCAGAAAGGAAGGACAGAATGTGACCCTGAGTTGTGAACAGAATTTGAACCACCACAGTGC CATGTACTGGTACCGACAGGACCCAGGGCAAGGGCTGAGATTGATCTACTACTCACAGATAGTAATGACTTTC AGAAAGGAGATATAGCTGAAGGGTACAGCGTCTCTCGGGAGAAGAAGGAATCCTTTCCTCT | CACTGTGAC ATCGGCCCA AAAG | AACCCGACAGT TTCTATCTCTGTG CCAGTAGTATAG A |
| hTRBV20 | hTRBV20 | 225 | ATGCTGCTGCTTCTGCTGCTTCTGGGGCCAGGTATAAGCCTCCTTCTACCTGGAGCTTGGCAGGCTCCGGGCTTG GTGCTGTCGTCTCTCAACATCCGAGCTGGGTTATCTGTAAGAGTGGAACCTCTGTGAAGATCGAGTGCCGTTCC TGGACTTTCAGGCCACAACTATGTTTTGGTATCGTCAGTTCCCGAAACAGAGTCTCATGCTGATGCAACTTCCA ATGAGGGCTTCCAAGGCCACATACGGCAAGGCGTCGAGAAGGACAAGTTTTCATCAACCATGCAAGCCTGACC TTGTCCACT | CTGACAGTG ACCAGTGCC CATC | CTGAAGACAGCA GCTTCTACATCT GCAGTGCTAGAG A |
| hTRBV21 | hTRBV21 | 226 | ATGTCCTCAGACTTCTCTGCTGTGCGCCATTTCTCTTTCTGGGGAGCCAGGCTCCAGGAACACCAAAGGTCACCCA GAGACCTAGACTTCTGGTCAAAGCAAGTGAACAGAAAGCAAAGATGGATTGTGTTCCTATAAAAGCACATAGTT ATGTTACTGGTATCGTAAGAACTGGAAGAGACTCAAGTTTTGGTTTACTTCAGAATGAAGAACTTATTC AGAAAGCAGAAATAATCAATGAGCGATTTTTAGCCCAATGCTCCAAAAACTCATCCTGTACCTTG | GAGATCCAG TCCACGGAG TCAG | GGGACACAGCAC TGTATTCTGTGC CAGCAGCAAAGC |
| hTRBV22 | hTRBV22 | 227 | ATGGGGAGCTGGGTTCCTCTGCTATGTGACCCTGTGTCTCTCCGGAGCAGGACCCTTGACTGCTGCACATCTATCAG ATGCCATTCCAGCTCACTGGGCTTCGATGGGATGATGCCTAAAGCAAAATCTGGAGTGGAAACGCAAAATCTGAGAGAGACACAAATGAA GTACTGCTACTGGTACTGCAGGACCCCAGAGGCTACGTGTCTGCCAAGACTGAGGATGATGTCCTCCGTTG TTCAGAGGAGATCTAACTGAAGGCTCCTGTGTCTCCTCCGGCAGCAGACTCTTTTCATGCCAAAGTCACACAG | GTGAAGTTG GCCCACACC AGCCA | AACAGCTTTGTA CTTCTGTCCTGG GAGCGCAC |
| hTRBV23 | hTRBV23 | 228 | ATGGGCACCAGGCTCCTCTTCTCTGCTGGCCTGTGAGCAGATCTTCTTCATGCCAAAGTCACACAG ACTCCAGGACATTTGTATCAACAGAATCAGAATAAAGAGTTTATGCTTTTGATTTCCTTTCAGAATGAACAAGTTCTTCAA TGTTTATTGGTATCAACAGAATCAGAATAAAGAGTTTATGCTTTTGATTTCCTTTCAGAATGAACAAGTTCTTCAA GAAACGGAGATGCACAAGAGTCACGATTCTCATCTCAATGCCCCAAGAACGCACCCTGCAG | CCTGCAAT CCTGTCCTC AGAA | CCGGGAGACACG GCACTGTATCTC TGCGCCAGCAGT CAATC |
| hTRBV24 | hTRBV24 | 229 | ATGGCCTCCCTGCTCTTCTTCTGTGGGCCCTTTTATCTCCTGGGAACAGGGTCCATGGATGCTGATGTTACCCAGA CCCCAAGGATAGGATCACAAAGACAGGAAAGAAGAAAGAGGATTATGCTGGAATGTTCTCAGACTAAGGTCATGATAGA ATGTACTGGTATCGACAAGACCCGGGCATGGGCTGTCTCTACAGGCTTGATCTATTACTCCTTTGATGTCAAAGATATAAAC AAAGGAGAGATCTCTGATGGATACAGTGTCTCCGACAGGCACAGGCTAAATTCTCCCTGTCCTA | GAGTCTGCC ATCCCAAC CAGA | CAGCTCTTTACTT CTGTGCCACCAG TGATTTG |
| hTRBV25 | hTRBV25 | 230 | ATGACTATCAGGCTCCTCTGCTACATGGGTCTTTTATTTTCTGGGGAGAAGGATCTGAATGCCTCATGAAGAGCTGACATCTACCAG ACCCAAGATACCTTGTTATAGGACGCAGGAAAGAAGAATCACACTCGAGAATGTCTCAAACATGGCCCATGACAA AATGAACTGGTATCGACAAGATCCAGGAATGGAACTACACCTCATCCACTATTCCTATGGAGTTAATTCCACAGA GAAGGGAGATATCCCTGATGGATACAGTGTCTCAACAGTCTCCAGAAATAAGGACGGAGCATTTCCCTGACCCT | GGAGTCTGC CAGGCCCTC ACA | TACCTCTCAGTA CCTCTGTGCCAG CAGTGAATA |

TABLE 16-continued

TCR β chain V segments and binding sites for primers presented in Table 4 and Table 10. The sequence for each V segments presented in this table consists of three parts (listed from 5' to 3'): Sequence upstream of primer binding site, sequence of the primer binding site and sequence downstream of the primer binding site.

| V segment name | Primer name | SEQ ID NO | hTRBV sequence upstream of primer binding site | Primer binding site within hTRbV | hTRbV sequence downstream of primer binding site |
|---|---|---|---|---|---|
| hTRBV26 | hTRBV26 | 231 | ATGAGCAACAGGCTTCTCTGCTGTGTGATCATTTGTCTCCTAAGAGCAGGCCTCAAGGATGCTGTAGTTACACAA TTCCCAAGACACAGAATCATTGGGACAGGAAAGGAATTCATTCTACAGTGTTCCCAGAATATGAATCATGTTACA ATGTACTGGTATCGACAGGACCCAGGACTTGGACTTGAAGCTGGTCTATTATTCACCTGGCACTGGGAGCACTGAA AAAGGAGATATCTCTGAGGGGTATCATGTTTCTTGAAATACTATAGCATCTTTTCCCCTGACCCT | GAAGTCTGC CAGCACCAA CCAG | ACATCTGTGTAT CTCTATGCCAGC AGTTCATC |
| hTRBV27 | hTRBV27 | 232 | ATGGGCCCCCAGCTCCTTGCTATGTGGTCCTTTGCCTTCTAGGAGCAGGCCCAAGTGACCCAG AACCCAAGATACCTCATCACAGTGACTGGAAAGAAGTTAACAGTGACTTGTTCTCAGAATATGAACCATGAGTA TATGTCCTGTATCGACAAGACCCAGGGCTGGGCTTAAGGCAGATCTACTATTCAATGAATGTTGAGGTGACTGA TAAGGGAGATGTTCCTGAAGGGTACAAAGTCTCTCGAAAAGAGAAGAGGAATTTCCCCCTGATCCT | GGAGTCGCC CAGCCCCAA CCAG | ACCTCTCTGTACT TCTGTGCCAGCA GTTTATC |
| hTRBV28 | hTRBV28 | 233 | ATGGGAATCAGGCTCCTCTGTGTCTGTGGCCTTTTGTTCTTGGCCTGTAGGCCTCGAGATGTGAAAGTAACCAG AGTCGAGATATCTAGTCAAAAGACGGAGAAGAAAGTTTTTCGGAGAAAGTGTCCAGGATATGACCATGAAAA TATGTTCTGGTATCGACAAGACCCAGGTCTGGGGCTACGGCTGATCTATTTCTCATATGATGTTAAAATGAAAGA AAAGGAGATATTCCTGAGGGGTACAGTGTCTCTAGAGAGAAGAAGAGGAGCGCTTCTCCCTGATTCT | GGAGTCCGC CAGCACCAA CCAG | ACATCTATGTAC CTCTGTGCCAGC AGTTTATG |
| hTRBV29 | hTRBV29 | 234 | ATGCTGAGTCTTCTGCTCCTTCTCCTGGGACTAGGCTCTGTGTTCAGTGCTGTCATCTCAAAAGCCAAGCAGGG ATATCTGTCAACGTGAACCTCCCTGACATCCAGTGTCAAGTCGATAGCCAAGTCACCATGATGTTCTGGTACC GTCAGCAACCTGACAGAGCCTGACACTGATCGCAACTCAGGGCTCTGAGGCCACATATGAGAGTGGA TTTGTCATTGACAAGTTTCCCATCAGCCGCCCAAACCTAACATTCTCAACTCTGACT | GTGAGCAAC ATGAGCCCT GAAGA | CAGCAGCATATA TCTCTGCAGCGT TGAAGA |
| hTRBV30 | hTRBV30 | 235 | ATGCTCTGCTCTCCTCTCCTTGCCCTTCTCCTGGGCACTTTCTTTGGGTCAGATCTCAGACTATTCATCAATGGCCAG CGACCCTGGTCCAGCCTGTGGCCAGCCCGTGTCCAGCACCCTGAACTGCACACTCTGGAACATCAAACCCCAACCTAT ACTGGTACCGACAGCCTGCAGCGGCCTCCAGCTGCTCCTCACTCCGTTGGTATTGGCCAGATACAGCTCTG AGGTGCCCCAGAATCTCTCAGCCTCCAGACCCCCAGGAGTTCATCCT | GAGTTCTAA GAAGCTCCT TCTCA | GTGACTCTGGCT TCTATCTCTGTGC CTGGAGTGT |

What is claimed is:

1. A method for sequencing immune cell receptor genes, comprising
providing RNA from immune cells;
transcribing the RNA into complementary RNA (cRNA);
reverse transcribing the cRNA into complementary DNA (cDNA), using one or more primers that comprise a first adapter sequence, wherein each 5' end of the cDNA produced by reverse transcription contains the first adapter sequence;
amplifying the cDNA to produce a first amplification product using a first primer pair comprising a first primer that hybridizes to the first adapter sequence and a second primer that hybridizes to a constant region of immune cell receptor gene;
amplifying the first amplification product to produce a second amplification product using a second primer pair, in which
  i. a first primer of the second primer pair binds to the adapter sequence at the 5' end of the first amplification product,
  ii. the second primer of the second primer pair binds to the constant region of immune cell receptor gene in the first amplification product, and
  iii. the first and second primers comprise adapter sequences for sequencing; and
sequencing the second amplification product.

2. The method according to claim 1, wherein the reverse transcription step results in PCR products ranging from 150-600 bp.

3. The method according to claim 1, wherein the immune cell receptor genes are T-cell receptor (TCR) genes or B-cell receptor (BCR) genes.

4. The method of claim 1, wherein the one or more primers used for reverse transcription hybridize to TCR α chain V segments, optionally wherein the one or more primers used for reverse transcription comprise one or more of SEQ ID NOs: 1-50; or
wherein the one or more primers used for reverse transcription hybridize to TCR β chain V segments, optionally wherein the one or more primers used for reverse transcription comprise one or more of SEQ ID NOs: 51-100; or
wherein the one or more primers used for reverse transcription hybridize to TCR γ chain V segments; or
wherein the one or more primers used for reverse transcription hybridize to TCR δ chain V segments; or
wherein the one or more primers used for reverse transcription hybridize to BCR heavy chain V segments; or
wherein the one or more primers used for reverse transcription hybridize to BCR light chain V segments.

5. The method according to claim 1, wherein the one or more primers used for reverse transcription contain a nucleotide barcode sequence; optionally wherein the nucleotide barcode comprises 6 to 20 nucleotides.

6. The method according to claim 5, wherein the nucleotide barcode consists of 9 nucleotides; optionally wherein the nucleotide barcode consists of the sequence NNNNTNNNN, NNNNANNNN or HHHHHNNNN.

7. The method according to claim 1, wherein the first adapter sequence of the one or more primers used for the reverse transcription comprises a T7 adapter.

8. The method according to claim 1, wherein the immune cells are T-cells and wherein the second primer of the first pair of primers hybridizes to the constant region of a TCR gene.

9. The method according to claim 1, wherein the immune cells are B-cells and wherein the second primer of the first pair of primers hybridizes to the constant region of a BCR gene.

10. The method according to claim 1, wherein the sequencing is next generation sequencing.

11. The method according to claim 1, wherein the RNA from the immune cells is obtained by mixing immune cells with carrier cells before RNA extraction.

12. The method according to claim 1, wherein the immune cells are tumor-infiltrating lymphocytes.

13. The method according to claim 1, wherein the immune cells are CD4 or CD8 positive T-cells.

14. The method according to claim 1, wherein the immune cells are purified from peripheral blood mononuclear cells (PBMC) before RNA extraction.

15. The method according to claim 1, wherein the immune cells are part of a mixture of peripheral blood mononuclear cells (PBMC).

16. The method according to claim 1, wherein the immune cells are derived from a mammal; optionally wherein the mammal is a human or a mouse.

* * * * *

SEQUENCE LISTING

<160> NUMBER OF SEQ ID NOS: 360

<210> SEQ ID NO 1
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 1
tgtaatacga ctcactatag nnnntnnnnc ttctacagga gctccagatg aaag    54

<210> SEQ ID NO 2
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 2
tgtaatacga ctcactatag nnnntnnnnc ttttgaagga gctccagatg aaag    54

<210> SEQ ID NO 3
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 3
tgtaatacga ctcactatag nnnntnnnnt gctcatcctc caggtgcggg a    51

<210> SEQ ID NO 4
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 4
tgtaatacga ctcactatag nnnntnnnng aagaaaccat ctgcccttgt ga         52

<210> SEQ ID NO 5
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 5
tgtaatacga ctcactatag nnnntnnnnc ctgccccggg tttccctgag cgac        54

<210> SEQ ID NO 6
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 6
tgtaatacga ctcactatag nnnntnnnnt ctctgcgcat tgcagacacc ca          52

<210> SEQ ID NO 7
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 7
tgtaatacga ctcactatag nnnntnnnnt tgtttcatat cacagcctcc ca          52

<210> SEQ ID NO 8
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 8
tgtaatacga ctcactatag nnnntnnnng cttgtacatt acagccgtgc a    51

<210> SEQ ID NO 9
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 9
tgtaatacga ctcactatag nnnntnnnna tctgaggaaa ccctctgtgc a    51

<210> SEQ ID NO 10
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 10
tgtaatacga ctcactatag nnnntnnnna cctgacgaaa ccctcagccc at    52

<210> SEQ ID NO 11
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 11
tgtaatacga ctcactatag nnnntnnnnc ctatgcctgt ctttacttta atc    53

<210> SEQ ID NO 12
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

```
<400> SEQUENCE: 12
tgtaatacga ctcactatag nnnntnnnnc ttgaggaaac cctcagtcca tat         53

<210> SEQ ID NO 13
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 13
tgtaatacga ctcactatag nnnntnnnng aaaccatcaa cccatgtgag tga         53

<210> SEQ ID NO 14
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 14
tgtaatacga ctcactatag nnnntnnnna cttggagaaa gactcagttc aa          52

<210> SEQ ID NO 15
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 15
tgtaatacga ctcactatag nnnntnnnna cttggagaaa ggctcagttc aa          52

<210> SEQ ID NO 16
<211> LENGTH: 49
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
```

<223> OTHER INFORMATION: n is a, c, g, or t

<400> SEQUENCE: 16
tgtaatacga ctcactatag nnnntnnnnc tgcacatcac agcctccca                49

<210> SEQ ID NO 17
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 17
tgtaatacga ctcactatag nnnntnnnng tttggaatat cgcagcctct cat           53

<210> SEQ ID NO 18
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 18
tgtaatacga ctcactatag nnnntnnnnc cctgctcatc agagactcca ag            52

<210> SEQ ID NO 19
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 19
tgtaatacga ctcactatag nnnntnnnnc tctgctcatc agagactccc ag            52

<210> SEQ ID NO 20
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 20
tgtaatacga ctcactatag nnnntnnnnc cttgttcatc agagactcac ag    52

<210> SEQ ID NO 21
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 21
tgtaatacga ctcactatag nnnntnnnnt ccctgcacat cacagagacc caa    53

<210> SEQ ID NO 22
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 22
tgtaatacga ctcactatag nnnntnnnnt ctctgcaaat tgcagctact caa    53

<210> SEQ ID NO 23
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 23
tgtaatacga ctcactatag nnnntnnnnt tgtcatctcc gcttcacaac tgg    53

<210> SEQ ID NO 24
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:

<221> NAME/KEY: misc_feature
<222> LOCATION: (26)..(29)
<223> OTHER INFORMATION: n is a, c, g, or t

<400> SEQUENCE: 24
tgtaatacga ctcactatag nnnntnnnng ttttgaatat gctggtctct cat         53

<210> SEQ ID NO 25
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 25
tgtaatacga ctcactatag nnnntnnnnc ctgaagaaac catttgctca aga         53

<210> SEQ ID NO 26
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 26
tgtaatacga ctcactatag nnnntnnnnt ccttgttgat cacggcttcc cgg         53

<210> SEQ ID NO 27
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 27
tgtaatacga ctcactatag nnnntnnnna cctggagaag ccctcggtgc a           51

<210> SEQ ID NO 28
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 28
tgtaatacga ctcactatag nnnntnnnnc accatcacag cctcacaagt cgt        53

<210> SEQ ID NO 29
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 29
tgtaatacga ctcactatag nnnntnnnnt ttctgcacat cacagcccct a          51

<210> SEQ ID NO 30
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 30
tgtaatacga ctcactatag nnnntnnnnc tttatacatt gcagcttctc agcc       54

<210> SEQ ID NO 31
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 31
tgtaatacga ctcactatag nnnntnnnng tacatttcct cttcccagac cac        53

<210> SEQ ID NO 32
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)

<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 32
tgtaatacga ctcactatag nnnntnnnnc attgcatatc atggattccc agc    53

<210> SEQ ID NO 33
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 33
tgtaatacga ctcactatag nnnntnnnng ctatttgtac atcaaaggat ccc    53

<210> SEQ ID NO 34
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 34
tgtaatacga ctcactatag nnnntnnnnc agctccctgc acatcacagc ca    52

<210> SEQ ID NO 35
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 35
tgtaatacga ctcactatag nnnntnnnnt tgatcctgcc ccacgctacg ctga    54

<210> SEQ ID NO 36
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 36
tgtaatacga ctcactatag nnnntnnnnt tgatcctgca ccgtgctacc ttga    54

<210> SEQ ID NO 37
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 37
tgtaatacga ctcactatag nnnntnnnng ttctctccac atcactgcag cc    52

<210> SEQ ID NO 38
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 38
tgtaatacga ctcactatag nnnntnnnng ccacctatac atcagattcc ca    52

<210> SEQ ID NO 39
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 39
tgtaatacga ctcactatag nnnntnnnnt ctctgcacat tgtgccctcc ca    52

<210> SEQ ID NO 40
<211> LENGTH: 54
<212> TYPE: DNA
<213> ORGANISM: Artificial Sequence
<220> FEATURE:
<223> OTHER INFORMATION: Synthetic Polynucleotide
<220> FEATURE:

```
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 40
tgtaatacga ctcactatag nnnntnnnnc cctgtacctt acggcctccc agct          54

<210> SEQ ID NO 41
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 41
tgtaatacga ctcactatag nnnntnnnnc ttatcatatc atcatcacag cca           53

<210> SEQ ID NO 42
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 42
tgtaatacga ctcactatag nnnntnnnnt ccctgcatat tacagccacc caa           53

<210> SEQ ID NO 43
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 43
tgtaatacga ctcactatag nnnntnnnna cctcaccatc aattccttaa aac           53

<210> SEQ ID NO 44
<211> LENGTH: 53
<212> TYPE: DNA
<213> ORGANISM: Artificial Sequence
<220> FEATURE:
<223> OTHER INFORMATION: Synthetic Polynucleotide
```

<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 44
tgtaatacga ctcactatag nnnntnnnnt ccctgcatat cacagcctcc cag          53

<210> SEQ ID NO 45
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 45
tgtaatacga ctcactatag nnnntnnnnc ttcctgaata tctcagcatc cat          53

<210> SEQ ID NO 46
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 46
tgtaatacga ctcactatag nnnntnnnnt cctgaacatc acagccaccc ag           52

<210> SEQ ID NO 47
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 47
tgtaatacga ctcactatag nnnntnnnnt ccctgcacat acaggattcc cag          53

<210> SEQ ID NO 48
<211> LENGTH: 52
<212> TYPE: DNA
<213> ORGANISM: Artificial Sequence
<220> FEATURE:

<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 48
tgtaatacga ctcactatag nnnntnnnnc aagatctcag actcacagct gg                52

<210> SEQ ID NO 49
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 49
tgtaatacga ctcactatag nnnntnnnnc cgtctcagca ccctccacat ca                52

<210> SEQ ID NO 50
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 50
tgtaatacga ctcactatag nnnntnnnnc cattgtgaaa tattcagtcc agg               53

<210> SEQ ID NO 51
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 51
tgtaatacga ctcactatag nnnnannnng tggtcgcact gcagcaagaa ga                52

<210> SEQ ID NO 52
<211> LENGTH: 53
<212> TYPE: DNA
<213> ORGANISM: Artificial Sequence

```
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 52
tgtaatacga ctcactatag nnnnannnng atccggtcca caaagctgga gga            53

<210> SEQ ID NO 53
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 53
tgtaatacga ctcactatag nnnnannnnc atcaattccc tggagcttgg tga            53

<210> SEQ ID NO 54
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 54
tgtaatacga ctcactatag nnnnannnnt tcacctacac gccctgcagc cag            53

<210> SEQ ID NO 55
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 55
tgtaatacga ctcactatag nnnnannnnt tcacctacac accctgcagc cag            53

<210> SEQ ID NO 56
<211> LENGTH: 52
<212> TYPE: DNA
```

<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 56
tgtaatacga ctcactatag nnnnannnng aatgtgagca ccttggagct gg    52

<210> SEQ ID NO 57
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 57
tgtaatacga ctcactatag nnnnannnnt actgagtcaa acacggagct agg    53

<210> SEQ ID NO 58
<211> LENGTH: 53
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 58
tgtaatacga ctcactatag nnnnannnng ctctgagatg aatgtgagtg cct    53

<210> SEQ ID NO 59
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 59
tgtaatacga ctcactatag nnnnannnnc tgagctgaat gtgaacgcct t    51

<210> SEQ ID NO 60
<211> LENGTH: 51

```
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 60
tgtaatacga ctcactatag nnnnannnng agttctcgct caggctggag t          51

<210> SEQ ID NO 61
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 61
tgtaatacga ctcactatag nnnnannnnc tggggttgga gtcggctgct c          51

<210> SEQ ID NO 62
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 62
tgtaatacga ctcactatag nnnnannnnc ccctcacgtt ggcgtctgct g          51

<210> SEQ ID NO 63
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 63
tgtaatacga ctcactatag nnnnannnnt cccgctcagg ctgctgtcgg c          51

<210> SEQ ID NO 64
```

```
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 64
tgtaatacga ctcactatag nnnnannnng atttcccgct caggctggag t          51

<210> SEQ ID NO 65
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 65
tgtaatacga ctcactatag nnnnannnnt cccctcaag ctggagtcag ct          52

<210> SEQ ID NO 66
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 66
tgtaatacga ctcactatag nnnnannnnt cccactcagg ctggtgtcgg c          51

<210> SEQ ID NO 67
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 67
tgtaatacga ctcactatag nnnnannnnc tctgaagttc cagcgcacac a          51
```

-continued

```
<210> SEQ ID NO 68
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 68
tgtaatacga ctcactatag nnnnannnng atccagcgca cacagcagga g           51

<210> SEQ ID NO 69
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 69
tgtaatacga ctcactatag nnnnannnna ctctgaagat ccagcgcaca ga          52

<210> SEQ ID NO 70
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 70
tgtaatacga ctcactatag nnnnannnna gatccagcgc acagagcaag g           51

<210> SEQ ID NO 71
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 71
tgtaatacga ctcactatag nnnnannnnc agcgcacaga gcagcgggac t           51
```

<210> SEQ ID NO 72
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 72
tgtaatacga ctcactatag nnnnannnng agatccagcg cacagagcag g    51

<210> SEQ ID NO 73
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 73
tgtaatacga ctcactatag nnnnannnnc cctcaaccct ggagtctact a    51

<210> SEQ ID NO 74
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 74
tgtaatacga ctcactatag nnnnannnnt ccccaatcct ggcatccacc a    51

<210> SEQ ID NO 75
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 75
tgtaatacga ctcactatag nnnnannnnc taaacctgag ctctctggag ct    52

<210> SEQ ID NO 76
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 76
tgtaatacga ctcactatag nnnnannnnc cctcactctg gagtctgctg c    51

<210> SEQ ID NO 77
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 77
tgtaatacga ctcactatag nnnnannnnc cctcactctg gagtcagcta c    51

<210> SEQ ID NO 78
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 78
tgtaatacga ctcactatag nnnnannnnt cctcactctg gagtccgcta c    51

<210> SEQ ID NO 79
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 79
tgtaatacga ctcactatag nnnnannnnc cactctcaag atccagcctg ca          52

<210> SEQ ID NO 80
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 80
tgtaatacga ctcactatag nnnnannnng aggatccagc ccatggaacc ca          52

<210> SEQ ID NO 81
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 81
tgtaatacga ctcactatag nnnnannnnc tgaagatcca gcctgcagag c           51

<210> SEQ ID NO 82
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 82
tgtaatacga ctcactatag nnnnannnnc agccctcaga acccagggac t           51

<210> SEQ ID NO 83
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 83
tgtaatacga ctcactatag nnnnannnng agctccttgg agctggggga ct    52

<210> SEQ ID NO 84
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 84
tgtaatacga ctcactatag nnnnannnng gtgcagcctg cagaactgga g    51

<210> SEQ ID NO 85
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 85
tgtaatacga ctcactatag nnnnannnng acatccgctc accaggcctg g    51

<210> SEQ ID NO 86
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 86
tgtaatacga ctcactatag nnnnannnnt gagatccagg ctacgaagct t    51

<210> SEQ ID NO 87
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 87
tgtaatacga ctcactatag nnnnannnng aagatccatc ccgcagagcc g          51

<210> SEQ ID NO 88
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 88
tgtaatacga ctcactatag nnnnannnng gatccagcag gtagtgcgag g          51

<210> SEQ ID NO 89
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 89
tgtaatacga ctcactatag nnnnannnnc actgtgacat cggcccaaaa g          51

<210> SEQ ID NO 90
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 90
tgtaatacga ctcactatag nnnnannnnc tgacagtgac cagtgcccat c          51

<210> SEQ ID NO 91
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 91
tgtaatacga ctcactatag nnnnannnng agatccagtc cacggagtca g                51

<210> SEQ ID NO 92
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 92
tgtaatacga ctcactatag nnnnannnng tgaagttggc ccacaccagc ca               52

<210> SEQ ID NO 93
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 93
tgtaatacga ctcactatag nnnnannnnc ctggcaatcc tgtcctcaga a                51

<210> SEQ ID NO 94
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 94
tgtaatacga ctcactatag nnnnannnng agtctgccat ccccaaccag a                51

<210> SEQ ID NO 95
<211> LENGTH: 50
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)

<223> OTHER INFORMATION: n is a, c, g, or t

<400> SEQUENCE: 95
tgtaatacga ctcactatag nnnnannnng gagtctgcca ggccctcaca                50

<210> SEQ ID NO 96
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 96
tgtaatacga ctcactatag nnnnannnng aagtctgcca gcaccaacca g              51

<210> SEQ ID NO 97
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 97
tgtaatacga ctcactatag nnnnannnng gagtcgccca gccccaacca g              51

<210> SEQ ID NO 98
<211> LENGTH: 51
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 98
tgtaatacga ctcactatag nnnnannnng gagtccgcca gcaccaacca g              51

<210> SEQ ID NO 99
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature

```
<222> LOCATION: (26)..(29)
<223> OTHER INFORMATION: n is a, c, g, or t

<400> SEQUENCE: 99
tgtaatacga ctcactatag nnnnannnng tgagcaacat gagccctgaa ga      52

<210> SEQ ID NO 100
<211> LENGTH: 52
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (21)..(24)
<223> OTHER INFORMATION: n is a, c, g, or t
<220> FEATURE:
<221> NAME/KEY: misc_feature
<222> LOCATION: (26)..(29)
<223> OTHER INFORMATION: n is a, c, g, or t

<400> SEQUENCE: 100
tgtaatacga ctcactatag nnnnannnng agttctaaga agctccttct ca      52

<210> SEQ ID NO 101
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 101
tgtaatacga ctcactatag                                          20

<210> SEQ ID NO 102
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 102
ggccacagca ctgttgctct tgaag                                    25

<210> SEQ ID NO 103
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 103
ccactgtgca cctccttccc attc                                     24

<210> SEQ ID NO 104
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 104
tcgaccagct tgacatcaca gg                                       22

<210> SEQ ID NO 105
<211> LENGTH: 24
<212> TYPE: DNA
```

```
<213> ORGANISM: Artificial Sequence
<220> FEATURE:
<223> OTHER INFORMATION: Synthetic Polynucleotide

<400> SEQUENCE: 105
cagatttgtt gctccaggcc acag                                          24

<210> SEQ ID NO 106
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 106
tctgtgatat acacatcaga atc                                           23

<210> SEQ ID NO 107
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 107
gaatcaaaat cggtgaatag gcag                                          24

<210> SEQ ID NO 108
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 108
ggcagacaga cttgtcactg gatt                                          24

<210> SEQ ID NO 109
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 109
taggacaccg aggtaaagcc ac                                            22

<210> SEQ ID NO 110
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 110
ctgggtgacg ggtttggccc tat                                           23

<210> SEQ ID NO 111
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 111
ttgacagcgg aagtggttgc                                               20
```

<210> SEQ ID NO 112
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 112
ggctgctcag gcagtatctg gagtc                                              25

<210> SEQ ID NO 113
<211> LENGTH: 25
<212> TYPE: DNA
<213> ORGANISM: Artificial Sequence
<220> FEATURE:
<223> OTHER INFORMATION: Synthetic Polynucleotide

<400> SEQUENCE: 113
gccaggcaca ccagtgtggc ctttt                                              25

<210> SEQ ID NO 114
<211> LENGTH: 78
<212> TYPE: DNA
<213> ORGANISM: Artificial Sequence
<220> FEATURE:
<223> OTHER INFORMATION: Synthetic Polynucleotide

<400> SEQUENCE: 114
aatgatacgg cgaccaccga gatctacact ctttccctac acgacgctct tccgatcttg        60
taatacgact cactatag                                                      78

<210> SEQ ID NO 115
<211> LENGTH: 87
<212> TYPE: DNA
<213> ORGANISM: Artificial Sequence
<220> FEATURE:
<223> OTHER INFORMATION: Synthetic Polynucleotide

<400> SEQUENCE: 115
caagcagaag acggcatacg agatgcctaa gtgactggag ttcagacgtg tgctcttccg        60
atcctcagct ggtacacggc agggtca                                            87

<210> SEQ ID NO 116
<211> LENGTH: 88
<212> TYPE: DNA
<213> ORGANISM: Artificial Sequence
<220> FEATURE:
<223> OTHER INFORMATION: Synthetic Polynucleotide

<400> SEQUENCE: 116
caagcagaag acggcatacg agatgcctaa gtgactggag ttcagacgtg tgctcttccg        60
atcaaacaca gcgacctcgg gtgggaac                                           88

<210> SEQ ID NO 117
<211> LENGTH: 326
<212> TYPE: DNA
<213> ORGANISM: Artificial Sequence
<220> FEATURE:
<223> OTHER INFORMATION: Synthetic Polynucleotide

<400> SEQUENCE: 117
atgtggggag ctttccttct ctatgtttcc atgaagatgg gaggcactgc aggacaaagc        60

```
cttgagcagc cctctgaagt gacagctgtg gaaggagcca ttgtccagat aaactgcacg    120
taccagacat ctgggtttta tgggctgtcc tggtaccagc aacatgatgg cggagcaccc    180
acatttcttt cttacaatgc tctggatggt ttggaggaga caggtcgttt ttcttcattc    240
cttagtcgct ctgatagtta tggttacctc cttctacagg agctccagat gaaagactct    300
gcctcttact tctgcgctgt gagaga                                         326
```

```
<210> SEQ ID NO 118
<211> LENGTH: 326
<212> TYPE: DNA
<213> ORGANISM: Artificial Sequence
<220> FEATURE:
<223> OTHER INFORMATION: Synthetic Polynucleotide

<400> SEQUENCE: 118
atgtggggag ttttccttct ttatgtttcc atgaagatgg gaggcactac aggacaaaac    60
attgaccagc ccactgagat gacagctacg gaaggtgcca ttgtccagat caactgcacg    120
taccagacat ctgggttcaa cgggctgttc tggtaccagc aacatgctgg cgaagcaccc    180
acatttctgt cttacaatgt tctggatggt ttggaggaga aggtcgtttt tcttcattc    240 cttagtcggt ctaaagggta cagttacctc cttttgaagg agctccagat gaaagactct    300
gcctcttacc tctgtgctgt gagaga                                         326
```

```
<210> SEQ ID NO 119
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 119
atggctttgc agagcactct gggggcggtg tggctagggc ttctcctcaa ctctctctgg    60
aaggttgcag aaagcaagga ccaagtgttt cagccttcca cagtggcatc ttcagaggga    120
gctgtggtgg aaatcttctg taatcactct gtgtccaatg cttacaactt cttctggtac    180
cttcacttcc cgggatgtgc accaagactc cttgttaaag gctcaaagcc ttctcagcag    240
ggacgataca acatgaccta tgaacggttc tcttcatcgc tgctcatcct ccaggtgcgg    300
gaggcagatg ctgctgttta ctactgtgct gtggagga                            338
```

```
<210> SEQ ID NO 120
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 120
atggcctctg cacccatctc gatgcttgcg atgctcttca cattgagtgg gctgagagct    60
cagtcagtgg ctcagccgga agatcaggtc aacgttgctg aagggaatcc tctgactgtg    120
aaatgcacct attcagtctc tggaaaccct tatctttttt ggtatgttca ataccccaac    180
cgaggcctcc agttccttct gaaatacatc acaggggata acctggttaa aggcagctat    240
ggctttgaag ctgaatttaa caagagccaa acctccttcc acctgaagaa accatctgcc    300
cttgtgagcg actccgcttt gtacttctgt gctgtgagag aca                      343
```

```
<210> SEQ ID NO 121
<211> LENGTH: 328
```

```
<212> TYPE: DNA
<213> ORGANISM: Artificial Sequence
<220> FEATURE:
<223> OTHER INFORMATION: Synthetic Polynucleotide

<400> SEQUENCE: 121
atgaggcaag tggcgagagt gatcgtgttc ctgaccctga gtactttgag ccttgctaag      60
accacccagc ccatctccat ggactcatat gaaggacaag aagtgaacat aacctgtagc    120
cacaacaaca ttgctacaaa tgattatatc acgtggtacc aacagtttcc cagccaagga    180
ccacgattta ttattcaagg atacaagaca aaagttacaa cgaagtggc ctccctgttt    240 atccctgccg acagaaagtc cagcactctg agcctgcccc gggtttccct gagcgacact    300
gctgtgtact actgcctcgt gggtgaca                                         328

<210> SEQ ID NO 122
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 122
atgaagacat tgctggatt ttcgttcctg tttttgtggc tgcagctgga ctgtatgagt      60
agaggagagg atgtggagca gagtcttttc ctgagtgtcc gagagggaga cagctccgtt    120
ataaactgca cttacacaga cagctcctcc acctacttat actggtataa gcaagaacct    180
ggagcaggtc tccagttgct gacgtatatt ttttcaaata tggacatgaa acaagaccaa    240
agactcactg ttctattgaa taaaaaggat aaacatctgt ctctgcgcat tgcagacacc    300
cagactgggg actcagctat ctacttctgt gcagagagta                           340

<210> SEQ ID NO 123
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 123
atggagtcat tcctgggagg tgttttgctg atttttgtggc ttcaagtgga ctgggtgaag    60
agccaaaaga tagaacagaa ttccgaggcc ctgaacattc aggagggtaa acgccacc     120 ctgacctgca actatacaaa ctattcccca gcatacttac agtggtaccg acaagatcca    180
ggaagaggcc ctgtttttctt gctactcata cgtgaaaatg agaaagaaaa aaggaaagaa   240
agactgaagg tcacctttga taccacccctt aaacagagtt tgtttcatat cacagcctcc    300
cagcctgcag actcagctac ctacctctgt gctctagaca                           340

<210> SEQ ID NO 124
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 124
atggagaaga tgcggagacc tgtcctaatt atatttttgtc tatgtcttgg ctgggcaaat    60
ggagaaaacc aggtggagca cagccctcat tttctgggac cccagcaggg agacgttgcc   120
tccatgagct gcacgtactc tgtcagtcgt tttaacaatt gcagtggta caggcaaaat    180
```

```
acagggatgg gtcccaaaca cctattatcc atgtattcag ctggatatga gaagcagaaa      240
ggaagactaa atgctacatt actgaagaat ggaagcagct tgtacattac agccgtgcag      300
cctgaagatt cagccaccta tttctgtgct gtagatg                               337
```

<210> SEQ ID NO 125
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 125

```
atgctcctgt tgctcatacc agtgctgggg atgattttg ccctgagaga tgccagagcc       60
cagtctgtga gccagcataa ccaccacgta attctctctg aagcagcctc actggagttg      120
ggatgcaact attcctatgg tggaactgtt aatctcttct ggtatgtcca gtaccctggt      180
caacaccttc agcttctcct caagtacttt tcagggatc cactggttaa aggcatcaag       240
ggctttgagg ctgaatttat aaagagtaaa ttctcctta atctgaggaa accctctgtg       300
cagtggagtg acacagctga gtacttctgt gccgtgaatg c                          341
```

<210> SEQ ID NO 126
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 126

```
atgctcctgc tgctcgtccc agtgctcgag gtgattttta ctctgggagg aaccagagcc      60
cagtcggtga cccagcttga cagccacgtc tctgtctctg aaggaacccc ggtgctgctg      120
aggtgcaact actcatcttc ttattcacca tctctcttct ggtatgtgca caccccaac       180 aaaggactcc agcttctcct gaagtacaca tcagcggcca ccctggttaa aggcatcaac      240
ggttttgagg ctgaatttaa gaagagtgaa acctccttcc acctgacgaa accctcagcc     300
catatgagcg acgcggctga gtacttctgt gttgtgagtg a                          341
```

<210> SEQ ID NO 127
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 127

```
atgctcctgg agcttatccc actgctgggg atacattttg tcctgagaac tgccagagcc      60
cagtcagtga cccagcctga catccacatc actgtctctg aaggagcctc actggagttg      120
agatgtaact attcctatgg ggcaacacct tatctcttct ggtatgtcca gtcccccggc      180
caaggcctcc agctgctcct gaagtacttt tcaggagaca ctctggttca aggcattaaa     240
ggctttgagg ctgaatttaa gaggagtcaa tcttccttca atctgaggaa accctctgtg      300
cattggagtg atgctgctga gtacttctgt gctgtgggtg c                          341
```

<210> SEQ ID NO 128
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 128

| | |
|---|---|
| atgctcctgc tgctcgtccc agtgctcgag gtgattttta ccctgggagg aaccagagcc | 60 |
| cagtcggtga cccagcttgg cagccacgtc tctgtctctg aaggagccct ggttctgctg | 120 |
| aggtgcaact actcatcgtc tgttccacca tatctcttct ggtatgtgca atacccaac | 180 |
| caaggactcc agcttctcct gaagtacaca tcagcggcca ccctggttaa aggcatcaac | 240 |
| ggttttgagg ctgaatttaa gaagagtgaa acctccttcc acctgacgaa accctcagcc | 300 |
| catatgagcg acgcggctga gtacttctgt gctgtgagtg acaca | 345 |

<210> SEQ ID NO 129
<211> LENGTH: 418
<212> TYPE: DNA
<213> ORGANISM: Artificial Sequence
<220> FEATURE:
<223> OTHER INFORMATION: Synthetic Polynucleotide

<400> SEQUENCE: 129

| | |
|---|---|
| atgctcctgg tgctcatccc actgctgggg atacattttg tcctgagtga gaactgtcag | 60 |
| agcccagtca gtgacccagc ctgacatccg catcactgtc tctgaaggag cctcactgga | 120 |
| gttgagatgt aactattcct atggggcgat gttgtgggaa gtcagggacc ccaaacggag | 180 |
| ggaccggctg aagccatggc agaagaatgt ggattgtgaa gatttcatgg acatttatta | 240 |
| gttccccaaa ttaatacttt tataatttct tatgcctctc tttactgcaa tctctaaaca | 300 |
| taaattgtaa agatttcatg gacacttatc acttccccaa tcataccccc tgtgatttcc | 360 |
| tatgcctgtc tttactttaa tctcttaatc ctgtcagctg aggaggatgt atgtcacc | 418 |

<210> SEQ ID NO 130
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 130

| | |
|---|---|
| atgctcctgc tgctcgtccc agcgttccag gtgattttta ccctgggagg aaccagagcc | 60 |
| cagtctgtga cccagcttga cagccaagtc cctgtctttg aagaagcccc tgtggagctg | 120 |
| aggtgcaact actcatcgtc tgtttcagtg tatctcttct ggtatgtgca atacccaac | 180 |
| caaggactcc agcttctcct gaagtatta tcaggatcca ccctggttaa aggcatcaac | 240 |
| ggttttgagg ctgaatttaa caagagtcaa acttccttcc acttgaggaa accctcagtc | 300 |
| catataagcg acacggctga gtacttctgt gctgtgagtg a | 341 |

<210> SEQ ID NO 131
<211> LENGTH: 342
<212> TYPE: DNA
<213> ORGANISM: Artificial Sequence
<220> FEATURE:
<223> OTHER INFORMATION: Synthetic Polynucleotide

<400> SEQUENCE: 131

| | |
|---|---|
| atgctcttag tggtcattct gctgcttgga atgttcttca cactgagaac cagaacccag | 60 |
| tcggtgaccc agcttgatgg ccacatcact gtctctgaag aagcccctct ggaactgaag | 120 |
| tgcaactatt cctatagtgg agttccttct ctcttctggt atgtccaata ctctagccaa | 180 |
| agcctccagc ttctcctcaa agacctaaca gaggccaccc aggttaaagg catcagaggt | 240 |

```
tttgaggctg aatttaagaa gagcgaaacc tccttctacc tgaggaaacc atcaacccat    300
gtgagtgatg ctgctgagta cttctgtgct gtgggtgaca gg                      342
```

<210> SEQ ID NO 132
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 132

```
atgaattctt ctccaggacc agcgattgca ctattcttaa tgtttggggg aatcaatgga     60
gattcagtgg tccagacaga aggccaagtg ctcccctctg aaggggattc cctgattgtg    120
aactgctcct atgaaaccac acagtaccct tcccttttt ggtatgtcca atatcctgga    180
gaaggtccac agctccacct gaaagccatg aaggccaatg acaagggaag gaacaaaggt    240
tttgaagcca tgtaccgtaa agaaaccact tctttccact tggagaaaga ctcagttcaa    300
gagtcagact ccgctgtgta cttctgtgct ctgagtga                            338
```

<210> SEQ ID NO 133
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 133

```
atgaactatt ctccaggctt agtatctctg atactcttac tgcttggaag aacccgtgga     60
aattcagtga cccagatgga agggccagtg actctctcag aagaggcctt cctgactata    120
aactgcacgt acacagccac aggatacccct tcccttttct ggtatgtcca atatcctgga   180
gaaggtctac agctcctcct gaaagccacg aaggctgatg acaagggaag caacaaaggt    240
tttgaagcca cataccgtaa agaaaccact tctttccact tggagaaagg ctcagttcaa    300
gtgtcagact cagcggtgta cttctgtgct ctgagtga                            338
```

<210> SEQ ID NO 134
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 134

```
atgaaaaagc atctgacgac cttcttggtg attttgtggc tttatttta taggggaat     60 ggcaaaaacc aagtggagca gagtcctcag tccctgatca tcctggaggg aaagaactgc   120
actcttcaat gcaattatac agtgagcccc ttcagcaact taaggtggta taagcaagat   180
actgggagag gtcctgtttc cctgacaatc atgactttca gtgagaacac aaagtcgaac   240
ggaagatata cagcaactct ggatgcagac acaaagcaaa gctctctgca catcacagcc   300
tcccagctca gcgattcagc ctcctacatc tgtgtggtga gcg                     343
```

<210> SEQ ID NO 135
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 135

```
acggagaagc ccttgggagt ttcattcttg atttcctcct ggcagctgtg ctgggtgaat      60
agactacata cactggagca gagtccttca ttcctgaata ttcaggaggg aatgcatgcc     120
gttcttaatt gtacttatca ggagagaaca ctcttcaatt ccactggtt ccggcaggat      180 ccggggagaa gacttgtgtc tttgacctta attcaatcaa gccagaagga gcagggagac     240
aaatatttta aagaactgct tggaaaagaa aaattttata gtgtttggaa tatcgcagcc     300
tctcatctgg gagattcagc cacctacttc tgtgctttgc                           340
```

<210> SEQ ID NO 136
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 136

```
atgatatcct tgagagtttt actggtgatc ctgtggcttc agttaagctg ggtttggagc      60
caacggaagg aggtggagca ggatcctgga cccttcaatg ttccagaggg agccactgtc     120
gctttcaact gtacttacag caacagtgct tctcagtctt tcttctggta cagacaggat     180
tgcaggaaag aacctaagtt gctgatgtcc gtatactcca gtggtaatga agatggaagg     240
tttacagcac agctcaatag agccagccag tatatttccc tgctcatcag agactccaag     300
ctcagtgatt cagccaccta cctctgtgtg gtgaaca                              337
```

<210> SEQ ID NO 137
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 137

```
atgaaatcct tgagagtttt actagtgatc ctgtggcttc agttgagctg ggtttggagc      60
caacagaagg aggtggagca gaattctgga cccctcagtg ttccagaggg agccattgcc     120
tctctcaact gcacttacag tgaccgaggt tcccagtcct tcttctggta cagacaatat     180
tctgggaaaa gccctgagtt gataatgttc atatactcca atggtgacaa agaagatgga     240
aggtttacag cacagctcaa taagccagc cagtatgttt ctctgctcat cagagactcc     300
cagcccagtg attcagccac ctacctctgt gccgtgaa                             338
```

<210> SEQ ID NO 138
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 138

```
atgaaatcct tgagagtttt actggtgatc ctgtggcttc agttaagctg ggtttggagc      60
caacagaagg aggtggagca ggatcctgga ccactcagtg ttccagaggg agccattgtt     120
tctctcaact gcacttacag caacagtgct tttcaatact tcatgtggta cagacagtat     180
tccagaaaag ccctgagtt gctgatgtac acatactcca gtggtaacaa agaagatgga     240
aggtttacag cacaggtcga taatccagc aagtatatct ccttgttcat cagagactca     300
cagcccagtg attcagccac ctacctctgt gcaatgagcg cacag                    345
```

<210> SEQ ID NO 139
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 139

```
atgacatcca ttcgagctgt atttatattc ctgtggctgc agctggactt ggtgaatgga      60
gagaatgtgg agcagcatcc ttcaaccctg agtgtccagg agggagacag cgctgttatc     120
aagtgtactt attcagacag tgcctcaaac tacttccctt ggtataagca agaacttgga     180
aaaggacctc agcttattat agacattcgt tcaaatgtgg gcgaaaagaa agaccaacga     240
attgctgtta cattgaacaa gacagccaaa catttctccc tgcacatcac agagacccaa     300
cctgaagact cggctgtcta cttctgtgca gcaagta                              337
```

<210> SEQ ID NO 140
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 140

```
atggcaggca ttcgagcttt atttatgtac ttgtggctgc agctggactg ggtgagcaga      60
ggagagagtg tggggctgca tcttcctacc ctgagtgtcc aggagggtga caactctatt     120
atcaactgtg cttattcaaa cagcgcctca gactacttca tttggtacaa gcaagaatct     180
ggaaaaggtc ctcaattcat tatagacatt cgttcaaata tggacaaaag gcaaggccaa     240
agagtcaccg ttttattgaa taagacatg aaacatctct ctctgcaaat tgcagctact     300
caacctggag actcagctgt ctacttttgt gcagagaata                           340
```

<210> SEQ ID NO 141
<211> LENGTH: 350
<212> TYPE: DNA
<213> ORGANISM: Artificial Sequence
<220> FEATURE:
<223> OTHER INFORMATION: Synthetic Polynucleotide

<400> SEQUENCE: 141

```
atgtcacttt ctagcctgct gaaggtggtc acagcttcac tgtggctagg acctggcatt      60
gcccagaaga taactcaaac ccaaccagga atgttcgtgc aggaaaagga ggctgtgact     120
ctggactgca catatgacac cagtgatcaa agttatggtc tattctggta caagcagccc     180
agcagtgggg aaatgatttt tcttatttat caggggtctt atgacgagca aaatgcaaca     240
gaaggtcgct actcattgaa tttccagaag gcaagaaaat ccgccaacct tgtcatctcc     300
gcttcacaac tgggggactc agcaatgtat ttctgtgcaa tgagagaggg                350
```

<210> SEQ ID NO 142
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 142

```
atgtatacgt atgtaacaaa cctgcgcgtt gtgcacatgt accctagaac gggtgaacag      60
cctccatatt ctggagtaga gtccttcatt cattcctgag tatccgggag ggaatgcaca     120
```

```
acattcttaa ttgcacttat gaggagagaa cgttctctta acttctactg gttctggcag      180
ggtctggaaa aggacttgtg tctttgacct taattcaatc aagccagatg gaggagggag      240
acaaacattt taaagaagcg cttggaaaag agaagtttta tagtgttttg aatatgctgg      300
tctctcatcc tggagattca ggcacctact tctgtgcttt gagg                      344
```

<210> SEQ ID NO 143
<211> LENGTH: 329
<212> TYPE: DNA
<213> ORGANISM: Artificial Sequence
<220> FEATURE:
<223> OTHER INFORMATION: Synthetic Polynucleotide

<400> SEQUENCE: 143

```
atgaagccca ccctcatctc agtgcttgtg ataatattta tactcagagg aacaagagcc       60
cagagagtga ctcagcccga agctcctc tctgtcttta aggggcccc agtggagctg        120 aagtgcaact attcctattc tgggagtcct gaactcttct ggtatgtcca gtactccaga      180
caacgcctcc agttactctt gagacacatc tctagagaga gcatcaaagg cttcactgct      240
gaccttaaca aggcgagac atctttccac ctgaagaaac catttgctca agaggaagac      300
tcagccatgt attactgtgc tctaagtgg                                        329
```

<210> SEQ ID NO 144
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 144

```
atggaaactc tcctgggagt gtcttggtg attctatggc ttcaactggc tagggtgaac       60
agtcaacagg gagaagagga tcctcaggcc ttgagcatcc aggagggtga aaatgccacc     120
atgaactgca gttacaaaac tagtataaac aatttacagt ggtatagaca aaattcaggt     180
agaggccttg tccacctaat tttaatacgt tcaaatgaaa gagagaaaca cagtggaaga     240
ttaagagtca cgcttgacac ttccaagaaa agcagttcct tgttgatcac ggcttcccgg     300
gcagcagaca ctgcttctta cttctgtgct acggacg                              337
```

<210> SEQ ID NO 145
<211> LENGTH: 333
<212> TYPE: DNA
<213> ORGANISM: Artificial Sequence
<220> FEATURE:
<223> OTHER INFORMATION: Synthetic Polynucleotide

<400> SEQUENCE: 145

```
atgctgtctg cttcctgctc aggacttgtg atcttgttga tattcagaag gaccagtgga       60
gactcggtta cccagacaga aggcccagtt accctccctg agagggcagc tctgacatta     120
aactgcactt atcagtccag ctattcaact tttctattct ggtatgtcca gtatctaaac     180
aaagagcctg agctcctcct gaaaagttca gaaaaccagg agacggacag cagaggtttt     240
caggccagtc ctatcaagag tgacagttcc ttccacctgg agaagccctc ggtgcagctg     300
tcggactctg ccgtgtacta ctgcgctctg aga                                  333
```

<210> SEQ ID NO 146
<211> LENGTH: 350
<212> TYPE: DNA

```
<213> ORGANISM: Artificial Sequence
<220> FEATURE:
<223> OTHER INFORMATION: Synthetic Polynucleotide

<400> SEQUENCE: 146
atgctgactg ccagcctgtt gagggcagtc atagcctcca tctgtgttgt atccagcatg      60
gctcagaagg taactcaagc gcagactgaa atttctgtgg tggagaagga ggatgtgacc     120
ttggactgtg tgtatgaaac ccgtgatact acttattact tattctggta caagcaacca     180
ccaagtggag aattggtttt ccttattcgt cggaactctt tgatgagca aatgaaata      240 agtggtcggt attcttggaa cttccagaaa tccaccagtt ccttcaactt caccatcaca     300
gcctcacaag tcgtggactc agcagtatac ttctgtgctc tgagtgaggc                350

<210> SEQ ID NO 147
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 147
atggagaaaa tgttggagtg tgcattcata gtcttgtggc ttcagcttgg ctggttgagt      60
ggagaagacc aggtgacgca gagtcccgag gccctgagac tccaggaggg agagagtagc     120
agtcttaact gcagttacac agtcagcggt ttaagagggu tgttctggta taggcaagat     180
cctgggaaag gccctgaatt cctcttcacc ctgtattcag ctggggaaga aaaggagaaa     240
gaaaggctaa agccacatt aacaaagaag gaaagctttc tgcacatcac agcccctaaa     300
cctgaagact cagccactta tctctgtgct gtgcagg                              337

<210> SEQ ID NO 148
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 148
atggagaccc tcttgggcct gcttatcctt tggctgcagc tgcaatgggt gagcagcaaa      60
caggaggtga cgcagattcc tgcagctctg agtgtcccag aaggagaaaa cttggttctc     120
aactgcagtt tcactgatag cgctatttac aacctccagt ggtttaggca ggaccctggg     180
aaaggtctca catctctgtt gcttattcag tcaagtcaga gagagcaaac aagtggaaga     240
cttaatgcct cgctggataa atcatcagga cgtagtactt tatacattgc agcttctcag     300
cctggtgact cagccaccta cctctgtgct gtgagg                               336

<210> SEQ ID NO 149
<211> LENGTH: 331
<212> TYPE: DNA
<213> ORGANISM: Artificial Sequence
<220> FEATURE:
<223> OTHER INFORMATION: Synthetic Polynucleotide

<400> SEQUENCE: 149
atgaagagga tattgggagc tctgctgggg ctcttgagtg cccaggtttg ctgtgtgaga      60
ggaatacaag tggagcagag tcctccagac ctgattctcc aggagggagc caattccacg     120
ctgcggtgca attttctga ctctgtgaac aatttgcagt ggtttcatca aaacccttgg     180
ggacagctca tcaacctgtt ttacattccc tcagggacaa aacagaatgg aagattaagc     240
```

```
gccacgactg tcgctacgga acgctacagc ttattgtaca tttcctcttc ccagaccaca    300
gactcaggcg tttatttctg tgctgtggag c                                   331

<210> SEQ ID NO 150
<211> LENGTH: 364
<212> TYPE: DNA
<213> ORGANISM: Artificial Sequence
<220> FEATURE:
<223> OTHER INFORMATION: Synthetic Polynucleotide

<400> SEQUENCE: 150
atggacaaga tcttaggagc atcatttta gttctgtggc ttcaactatg ctgggtgagt      60
ggccaacaga aggagaaaag tgaccagcag caggtgaaac aaagtcctca atctttgata   120
gtccagaaag gagggatttc aattataaac tgtgcttatg agaacactgc gtttgactac   180
tttccatggt accaacaatt ccctgggaaa ggccctgcat tattgatagc catacgtcca   240
gatgtgagtg aaaagaaaga aggaagattc acaatctcct tcaataaaag tgccaagcag   300
ttctcattgc atatcatgga ttcccagcct ggagactcag ccacctactt ctgtgcagca   360
agca                                                                 364

<210> SEQ ID NO 151
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 151
atggagaaga tcctttggc agccccatta ctaatcctct ggtttcatct tgactgcgtg      60
agcagcatac tgaacgtgga acaaagtcct cagtcactgc atgttcagga gggagacagc   120
accaatttca cctgcagctt cccttccagc aattttatg ccttacactg gtacagatgg    180
gaaactgcaa aaagccccga ggccttgttt gtaatgactt taaatgggga tgaaaagaag   240
aaaggacgaa taagtgccac tcttaatacc aaggagggtt acagctattt gtacatcaaa   300
ggatcccagc ctgaagactc agccacatac ctctgtgcct tta                     343

<210> SEQ ID NO 152
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 152
atgctactca tcacatcaat gttggtctta tggatgcaat tgtcacaggt gaatggacaa      60
caggtaatgc aaattcctca gtaccagcat gtacaagaag gagaggactt caccacgtac   120
tgcaattcct caactacttt aagcaatata cagtggtata gcaaaggcc tggtggacat    180 cccgtttttt tgatacagtt agtgaagagt ggagaagtga agaagcagaa aagactgaca   240
tttcagtttg agaagcaaa aaagaacagc tccctgcaca tcacagccac ccagactaca   300
gatgtaggaa cctacttctg tgcaggg                                       327

<210> SEQ ID NO 153
<211> LENGTH: 328
<212> TYPE: DNA
<213> ORGANISM: Artificial Sequence
<220> FEATURE:
```

<223> OTHER INFORMATION: Synthetic Polynucleotide

<400> SEQUENCE: 153

```
atgaggctgg tggcaagagt aactgtgttt ctgacctttg aactataat tgatgctaag      60
accacccagc cccctccat ggattgcgct gaaggaagag ctgcaaacct gccttgtaat     120
cactctacca tcagtggaaa tgagtatgtg tattggtatc gacagattca ctcccagggg    180
ccacagtata tcattcatgg tctaaaaaac aatgaaacca atgaaatggc ctctctgatc    240
atcacagaag acagaaagtc cagcaccttg atcctgcccc acgctacgct gagagacact    300
gctgtgtact attgcatcgt cagagtcg                                       328
```

<210> SEQ ID NO 154
<211> LENGTH: 327
<212> TYPE: DNA
<213> ORGANISM: Artificial Sequence
<220> FEATURE:
<223> OTHER INFORMATION: Synthetic Polynucleotide

<400> SEQUENCE: 154

```
atgaagttgg tgacaagcat tactgtactc ctatctttgg gtattatggg tgatgctaag      60
accacacagc caaattcaat ggagagtaac gaagaagagc tgttcactt gccttgtaac     120
cactccacaa tcagtggaac tgattacata cattggtatc gacagcttcc ctcccagggt    180
ccagagtacg tgattcatgg tcttacaagc aatgtgaaca acagaatggc ctctctggca    240
atcgctgaag acagaaagtc cagtaccttg atcctgcacc gtgctacctt gagagatgct    300
gctgtgtact actgcatcct gagagac                                        327
```

<210> SEQ ID NO 155
<211> LENGTH: 328
<212> TYPE: DNA
<213> ORGANISM: Artificial Sequence
<220> FEATURE:
<223> OTHER INFORMATION: Synthetic Polynucleotide

<400> SEQUENCE: 155

```
atggtcctga aattctccgt gtccattctt tggattcagt ggcatgggt gagcacccag      60
ctgctggagc agagccctca gtttctaagc atccaagagg gagaaaatct cactgtgtac    120
tgcaactcct caagtgtttt ttccagctta caatggtaca gacaggagcc tggggaaggt    180
cctgtcctcc tggtgacagt agttacgggt ggagaagtga agaagctgaa gagactaacc    240
tttcagtttg gtgatgcaag aaaggacagt tctctccaca tcactgcagc ccagcctggt    300
gatacaggcc tctacctctg tgcaggag                                       328
```

<210> SEQ ID NO 156
<211> LENGTH: 323
<212> TYPE: DNA
<213> ORGANISM: Artificial Sequence
<220> FEATURE:
<223> OTHER INFORMATION: Synthetic Polynucleotide

<400> SEQUENCE: 156

```
atgaaggcat aataggaat cttgctgggc ttcctgtgga tacagatttg ctcgcaaatg      60
aaagtggagc agagtcctca ggtcctgatc ctccaagagg gaagaaattc attcctggtg    120
tgcagttgtt ctatttacat gatccgtgtg cagtggtttc atcaaaagcc tggaggaccc    180
ctcatgtcct tatttaacat taattcagga atacagcaaa aagaagact aaatccgca     240
gtcaaagctg aggaacttta tggccaccta tacatcagat tcccagcctg aggactcagc    300
```

-continued

```
tatttacttc tgtgctgtgg gga                                      323
```

<210> SEQ ID NO 157
<211> LENGTH: 358
<212> TYPE: DNA
<213> ORGANISM: Artificial Sequence
<220> FEATURE:
<223> OTHER INFORMATION: Synthetic Polynucleotide

<400> SEQUENCE: 157

```
atggccatgc tcctgggggc atcagtgctg attctgtggc ttcagccaga ctgggtaaac    60
agtcaacaga agaatgatga ccagcaagtt aagcaaaatt caccatccct gagcgtccag   120
gaaggaagaa tttctattct gaactgtgac tatactaaca gcatgtttga ttatttccta   180
tggtacaaaa ataccctgc tgaaggtcct acattcctga tatctataag ttccattaag   240
gataaaaatg aagatggaag attcactgtc ttcttaaaca aaagtgccaa gcacctctct   300
ctgcacattg tgccctccca gcctggagac tctgcagtgt acttctgtgc agcaagcg     358
```

<210> SEQ ID NO 158
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 158

```
atggagactc tcctgaaagt gctttcaggc accttgttgt ggcagttgac ctgggtgaga    60
agccaacaac cagtgcagag tcctcaagcc gtgatcctcc gagaagggga agatgctgtc   120
atcaactgca gttcctccaa ggctttatat tctgtacact ggtacaggca gaagcatggt   180
gaagcacccg tcttcctgat gatattactg aagggtggag aacagaaggg tcatgaaaaa   240
atatctgctt catttaatga aaaaaagcag caaagctccc tgtaccttac ggcctcccag   300
ctcagttact caggaaccta cttctgcggc acagaga                            337
```

<210> SEQ ID NO 159
<211> LENGTH: 342
<212> TYPE: DNA
<213> ORGANISM: Artificial Sequence
<220> FEATURE:
<223> OTHER INFORMATION: Synthetic Polynucleotide

<400> SEQUENCE: 159

```
atgactgttg gcagcatatt acgggcactc atggcctctg ccttccttgc atgtcacaga    60
gggtcattca atcccaacca gcaatatcta cgcaggaggg tgagaccgtg aaactggact   120
gtgcatacaa aactaatatt gtatattaca tattgtattg gtacaaaagg tctcccaatg   180
ggaagattat tttcctcatt tatcagcaaa cagatgcaga aaccaatgcg acacagggtc   240
aatattctgt gagcttccag aaaacaacta aaactattca gcttatcata tcatcatcac   300
agccagaaga cctgcaacat atttctgttg tctcaaagag cc                       342
```

<210> SEQ ID NO 160
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 160

| | |
|---|---|
| atggcaagaa gaatggaaaa gtccctggga gctttattca aattcagctg aagctggcca | 60 |
| agaaaaggat gtgatacaga gttattcaaa tctaaatgtc taggagagag aaatggccgt | 120 |
| tattaatgac agttatacag atggagcttt gaattatttc tgttggtaca agaagaaaac | 180 |
| ggggaaggcc ctaatatctt aatggagatt cattcaaatg tggatagaaa acaggacaga | 240 |
| aggctcactg tactgttgaa taaaaatgct aaacatgtct ccctgcatat tacagccacc | 300 |
| caaccaggag actcattcct gtacttctgt gcagtgagaa caca | 344 |

<210> SEQ ID NO 161
<211> LENGTH: 338
<212> TYPE: DNA
<213> ORGANISM: Artificial Sequence
<220> FEATURE:
<223> OTHER INFORMATION: Synthetic Polynucleotide

<400> SEQUENCE: 161

| | |
|---|---|
| atgctctgcc ctggcctgct gtgggcattc gtggtcccct ttggcttcag atccagcatg | 60 |
| gctcagaaag taacccaagt tcagaccaca gtaactaggc agaaaggagt agctgtgacc | 120 |
| ttggactgca catgtttgaaac cagatagaat tcgtacactt tatactggta caagcaacaa | 180 |
| gcaacctccc agtgaagaga tggttttcct tattcatcag ggttattcta agtcaaatgc | 240 |
| aaagcctgtg aactttgaaa aaagaaaaa gttcatcaac ctcaccatca attccttaaa | 300 |
| actgactcag ccaagtactt ctgtgctctc aggaatcc | 338 |

<210> SEQ ID NO 162
<211> LENGTH: 337
<212> TYPE: DNA
<213> ORGANISM: Artificial Sequence
<220> FEATURE:
<223> OTHER INFORMATION: Synthetic Polynucleotide

<400> SEQUENCE: 162

| | |
|---|---|
| atggagactg ttctgcaagt actcctaggg atattggggt tccaagcagc ctgggtcagt | 60 |
| agccaagaac tggagcagag tcctcagtcc ttgatcgtcc aagagggaaa gaatctcacc | 120 |
| ataaactgca cgtcatcaaa gacgttatat ggcttatact ggtataagca aaagtatggt | 180 |
| gaaggtctta tcttcttgat gatgctacag aaaggtgggg aagagaaaag tcatgaaaag | 240 |
| ataactgcca gttggatga aaaaagcag caaagttccc tgcatatcac agcctcccag | 300 |
| cccagccatg caggcatcta cctctgtgga gcagaca | 337 |

<210> SEQ ID NO 163
<211> LENGTH: 330
<212> TYPE: DNA
<213> ORGANISM: Artificial Sequence
<220> FEATURE:
<223> OTHER INFORMATION: Synthetic Polynucleotide

<400> SEQUENCE: 163

| | |
|---|---|
| atgctccttg aacatttatt aataatcttg tggatgcagc tgacatgggt cagtggtcaa | 60 |
| cagctgaatc agagtcctca atctatgttt atccaggaag agaagatgt ctccatgaac | 120 |
| tgcacttctt caagcatatt taacacctgg ctatggtaca agcaggaacc tgggaaggt | 180 |
| cctgtcctct tgatagcctt atataaggct ggtgaattga cctcaaatgg aagactgact | 240 |
| gctcagtttg gtataaccag aaaggacagc ttcctgaata tctcagcatc catacctagt | 300 |
| gatgtaggca tctacttctg tgctgggcag | 330 |

<210> SEQ ID NO 164
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 164

```
atgatgaagt gtccacaggc tttactagct atcttttggc ttctactgag ctgggtgagc    60
agtgaagaca aggtggtaca aagccctcta tctctggttg tccacgaggg agacaccgta   120
actctcaatt gcagttatga agtgactaac tttcgaagcc tactatggta caagcaggaa   180
aagaaagctc ccacatttct atttatgcta acttcaagtg gaattgaaaa gaagtcagga   240
agactaagta gcatattaga taagaaagaa ctttccagca tcctgaacat cacagccacc   300
cagaccggag actcggccat ctacctctgt gctgtggagg                         340
```

<210> SEQ ID NO 165
<211> LENGTH: 342
<212> TYPE: DNA
<213> ORGANISM: Artificial Sequence
<220> FEATURE:
<223> OTHER INFORMATION: Synthetic Polynucleotide

<400> SEQUENCE: 165

```
atggaaactc cactgagcac tctgctgctg ctcctctgtg tgcagctgac ctggtcaaat    60
ggacaactgc cagtggaaca gaatgctcct tccctgaaag tcaaggaagg tgacagcgtc   120
acactgaact gcagttacag agacagccct tcagatttct tcagtggttc aggcaggatc   180
ctgaggaagg cctcatttcc ctgatacaaa tgctatcaac tgtgagagag aagatcagtg   240
gaagattcac agccaggctt aaaaaaggag accagcacat ttccctgcac atacaggatt   300
cccagctcca tgactcaacc acattcttct gcgcagcaag ca                     342
```

<210> SEQ ID NO 166
<211> LENGTH: 350
<212> TYPE: DNA
<213> ORGANISM: Artificial Sequence
<220> FEATURE:
<223> OTHER INFORMATION: Synthetic Polynucleotide

<400> SEQUENCE: 166

```
atgacacgag ttagcttgct gtgggcagtc gtggtctcca cctgtcttga atccggcatg    60
gcccagacag tcactcagtc tcaaccagag atgtctgtgc aggaggcaga gactgtgacc   120
ctgagttgca catatgacac cagtgagaat aattattatt tgttctggta caagcagcct   180
cccagcaggc agatgattct cgttattcgc caagaagctt ataagcaaca gaatgcaacg   240
gagaatcgtt tctctgtgaa cttccagaaa gcagccaaat ccttcagtct caagatctca   300
gactcacagc tgggggacac tgcgatgtat ttctgtgctt tcatgaagca              350
```

<210> SEQ ID NO 167
<211> LENGTH: 349
<212> TYPE: DNA
<213> ORGANISM: Artificial Sequence
<220> FEATURE:
<223> OTHER INFORMATION: Synthetic Polynucleotide

<400> SEQUENCE: 167

```
atggcatgcc ctggcttcct gtgggcactt gtgatctcca cctgtcttga atttagcatg    60
gctcagacag tcactcagtc tcaaccagag atgtctgtgc aggaggcaga gaccgtgacc   120
```

```
ctgagctgca catatgacac cagtgagagt gattattatt tattctggta caagcagcct      180
cccagcaggc agatgattct cgttattcgc caagaagctt ataagcaaca gaatgcaaca      240
gagaatcgtt tctctgtgaa cttccagaaa gcagccaaat ccttcagtct caagatctca      300
gactcacagc tgggggatgc cgcgatgtat ttctgtgctt ataggagcg                  349
```

<210> SEQ ID NO 168
<211> LENGTH: 331
<212> TYPE: DNA
<213> ORGANISM: Artificial Sequence
<220> FEATURE:
<223> OTHER INFORMATION: Synthetic Polynucleotide

<400> SEQUENCE: 168

```
atgaagaagc tactagcaat gattctgtgg cttcaactag accggttaag tggagagctg       60
aaagtggaac aaaaccctct gttcctgagc atgcaggagg gaaaaaacta taccatctac      120
tgcaattatt caaccacttc agacagactg tattggtaca ggcaggatcc tgggaaaagt      180
ctggaatctc tgtttgtgtt gctatcaaat ggagcagtga agcaggaggg acgattaatg      240
gcctcacttg ataccaaagc ccgtctcagc accctccaca tcacagctgc cgtgcatgac      300
ctctctgcca cctacttctg tgccgtggac a                                     331
```

<210> SEQ ID NO 169
<211> LENGTH: 317
<212> TYPE: DNA
<213> ORGANISM: Artificial Sequence
<220> FEATURE:
<223> OTHER INFORMATION: Synthetic Polynucleotide

<400> SEQUENCE: 169

```
atgaactcct ctctggactt tctaattctg atcttaatgt ttggaggaac cagcagcaat       60
tcagtcaagc agacgggcca ataaccgtc tcggagggag catctgtgac tatgaactgc       120
acatacacat ccacggggta ccctacccctt ttctggtatg tggaataccc cagcaaacct     180
ctgcagcttc ttcagagaga gacaatggaa aacagcaaaa acttcggagg cggaaatatt      240
aaagacaaaa actccccccat tgtgaaatat tcagtccagg tatcagactc agccgtgtac    300
tactgtcttc tgggaga                                                     317
```

<210> SEQ ID NO 170
<211> LENGTH: 336
<212> TYPE: DNA
<213> ORGANISM: Artificial Sequence
<220> FEATURE:
<223> OTHER INFORMATION: Synthetic Polynucleotide

<400> SEQUENCE: 170

```
atggtgaaga tccggcaatt tttgttggct attttgtggc ttcagctaag ctgtgtaagt       60
gccgccaaaa atgaagtgga gcagagtcct cagaacctga ctgcccagga aggagaattt     120
atcacaatca actgcagtta ctcggtagga ataagtgcct acactggct gcaacagcat       180 ccaggaggag gcattgtttc cttgtttatg ctgagctcag ggaagaagaa gcatggaaga     240
ttaattgcca caataaacat acaggaaaag cacagctccc tgcacatcac agcctcccat     300
cccagagact ctgccgtcta catctgtgct gtcaga                                336
```

<210> SEQ ID NO 171
<211> LENGTH: 333
<212> TYPE: DNA
<213> ORGANISM: Artificial Sequence

```
<220> FEATURE:
<223> OTHER INFORMATION: Synthetic Polynucleotide

<400> SEQUENCE: 171
atgggctgaa gtctccactg tggtgtggtc cattgtctca ggctccatgg atactggaat      60
tacccagaca ccaaaatacc tggtcacagc aatggggagt aaaaggacaa tgaaacgtga     120
gcatctggga catgattcta tgtattggta cagacagaaa gctaagaaat ccctggagtt     180
catgttttac tacaactgta aggaattcat tgaaaacaag actgtgccaa atcacttcac     240
acctgaatgc cctgacagct ctcgcttata ccttcatgtg gtcgcactgc agcaagaaga     300
ctcagctgcg tatctctgca ccagcagcca aga                                  333

<210> SEQ ID NO 172
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 172
atggatacct ggctcgtatg ctgggcaatt tttagtctct tgaaagcagg actcacagaa      60
cctgaagtca cccagactcc cagccatcag gtcacacaga tgggacagga agtgatcttg     120
cgctgtgtcc ccatctctaa tcacttatac ttctattggt acagacaaat cttggggcag     180
aaagtcgagt ttctggtttc cttttataat aatgaaatct cagagaagtc tgaaatattc     240
gatgatcaat tctcagttga aaggcctgat ggatcaaatt tcactctgaa gatccggtcc     300
acaaagctgg aggactcagc catgtacttc tgtgccagca gtgaagc                   347

<210> SEQ ID NO 173
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 173
atgggctgca ggctcctctg ctgtgtggtc ttctgcctcc tccaagcagg tcccttggac      60
acagctgttt cccagactcc aaaatacctg gtcacacaga tgggaaacga caagtccatt     120
aaatgtgaac aaaatctggg ccatgatact atgtattggt ataaacagga ctctaagaaa     180
tttctgaaga taatgtttag ctacaataat aaggagctca ttataaatga aacagttcca     240
aatcgcttct cacctaaatc tccagacaaa gctcacttaa atcttcacat caattccctg     300
gagcttggtg actctgctgt gtatttctgt gccagcagcc aaga                      344

<210> SEQ ID NO 174
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 174
atgggctgca ggctcctctg ctatgtggcc ctctgcctcc tgcaagcagg atccactgga      60
cacagccgtt tcccagactc caaaatacct ggtcacacag atgggaaaaa aggagtctct     120
taaatgagaa caaatctggg ccataatgc tatgtattgg tataaacagg actctaagaa     180
atttctgaag acaatgttta tctacagtaa caaggagcca attttaaatg aaacagttcc     240
```

```
aaatcgcttc tcacctgact ctccagacaa agctcattta atcttcaca tcaattccct    300 ggagcttggt gactctgctg tgtatttctg tgccagcagc aaga                    345
```

<210> SEQ ID NO 175
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 175

```
atgggctgca ggctgctctg ctgtgcggtt ctctgtctcc tgggagcagt tcccatagac    60
actgaagtta cccagacacc aaaacacctg gtcatgggaa tgacaaataa gaagtctttg   120
aaatgtgaac acatatggg gcacagggct atgtattggt acaagcagaa agctaagaag   180
ccaccggagc tcatgtttgt ctacagctat gagaaactct ctataaatga agtgtgcca   240 agtcgcttct cacctgaatg ccccaacagc tctctcttaa accttcacct acacgccctg   300
cagccagaag actcagccct gtatctctgc gccagcagcc aaga                    344
```

<210> SEQ ID NO 176
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 176

```
atgggctgca ggctgctctg ctgtgcggtt ctctgtctcc tgggagcggt ccccatggaa    60
acgggagtta cgcagacacc aagacacctg gtcatgggaa tgacaaataa gaagtctttg   120
aaatgtgaac acatctggg gcataacgct atgtattggt acaagcaaag tgctaagaag   180
ccactggagc tcatgtttgt ctacaacttt aaagaacaga ctgaaaacaa cagtgtgcca   240
agtcgcttct cacctgaatg ccccaacagc tctcacttat tccttcacct acacaccctg   300
cagccagaag actcggccct gtatctctgt gccagcagcc aaga                    344
```

<210> SEQ ID NO 177
<211> LENGTH: 353
<212> TYPE: DNA
<213> ORGANISM: Artificial Sequence
<220> FEATURE:
<223> OTHER INFORMATION: Synthetic Polynucleotide

<400> SEQUENCE: 177

```
atgggctgca ggctgctctg ctgtgcggtt ctctgtctcc tgggagcggg tgagttggtc    60
cccatggaaa cgggagttac gcagacacca agacacctgg tcatgggaat gacaaataag   120
aagtctttga aatgtgaaca acatctgggt cataacgcta tgtattggta caagcaaagt   180
gctaagaagc cactggagct catgtttgtc tacagtcttg aagaacgggt tgaaaacaac   240
agtgtgccaa gtcgcttctc acctgaatgc cccaacagct ctcacttatt ccttcaccta   300
cacaccctgc agccagaaga ctcggccctg tatctctgcg ccagcagcca aga           353
```

<210> SEQ ID NO 178
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 178

```
atgggctcca ggctgctctg ttgggtgctg ctttgtctcc tgggagcagg cccagtaaag      60
gctggagtca ctcaaactcc aagatatctg atcaaaacga gaggacagca agtgacactg     120
agctgctccc ctatctctgg cataggagt gtatcctggt accaacagac cccaggacag     180
ggccttcagt tcctctttga atacttcagt gagacacaga gaaacaaagg aaacttccct     240
ggtcgattct cagggcgcca gttctctaac tctcgctctg agatgaatgt gagcaccttg     300
gagctggggg actcggccct ttatctttgc gccagcagct tgg                      343
```

<210> SEQ ID NO 179
<211> LENGTH: 331
<212> TYPE: DNA
<213> ORGANISM: Artificial Sequence
<220> FEATURE:
<223> OTHER INFORMATION: Synthetic Polynucleotide

<400> SEQUENCE: 179

```
atgggctccg gactcctctg ctggacgctg ctttgtttcc tgggagcagg cccagtggag      60
gctggaatca cccaagctcc aagacacctg atcaaaacaa gagaccagca agtgacactg     120
agatgctccc ctgcctctgg cataactgt gtgtcctggt acctacgaac tccaagtcag     180
cccctctagt tattgttaca atattgtaat aggttacaaa gagcaaaagg aaacttgcct     240
aattgattct cagctcacca cgtccataac tattactgag tcaaacacgg agctagggga     300
ctcagccctg tatctctgtg ccagcaactt g                                   331
```

<210> SEQ ID NO 180
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 180

```
atgggccccg ggctcctctg ctgggaactg ctttatctcc tgggagcagg cccagtggag      60
gctggagtca cccaaagtcc cacacacctg atcaaaacga gaggacagca agtgactctg     120
agatgctctc ctatctctgg cacagcagt gtgtcctggt accaacaggc cccgggtcag     180 gggcccagt ttatctttga atatgctaat gagttaagga gatcagaagg aaacttccct     240
aatcgattct cagggcgcca gttccatgac tgttgctctg agatgaatgt gagtgccttg     300
gagctggggg actcggccct gtatctctgt gccagaagct tgg                      343
```

<210> SEQ ID NO 181
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 181

```
atgggccctg ggctcctctg ctgggtgctg ctttgtctcc tgggagcagg ctcagtggag      60
actggagtca cccaaagtcc cacacacctg atcaaaacga gaggacagca agtgactctg     120
agatgctctt ctcagtctgg cacaacact gtgtcctggt accaacaggc cctgggtcag     180 gggcccagt ttatctttca gtattatagg gaggaagaga atggcagagg aaacttccct     240
cctagattct caggtctcca gttccctaat tatagctctg agctgaatgt gaacgccttg     300
gagctggacg actcggccct gtatctctgt gccagcagct tgg                      343
```

<210> SEQ ID NO 182
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 182

```
atgggccctg ggctcctctg ctgggtgctg ctttgtctcc tgggagcagg cccagtggac      60
gctggagtca cccaaagtcc cacacacctg atcaaaacga gaggacagca agtgactctg     120
agatgctctc ctatctctgg cacaagagt gtgtcctggt accaacaggt cctgggtcag     180
gggccccagt ttatctttca gtattatgag aaagaagaga gaggaagagg aaacttccct     240
gatcgattct cagctcgcca gttccctaac tatagctctg agctgaatgt gaacgccttg     300
ttgctggggg actcggccct gtatctctgt gccagcagct tgg                        343
```

<210> SEQ ID NO 183
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 183

```
atgggccccg ggctcctctg ctgggcactg ctttgtctcc tgggagcagg cttagtggac      60
gctggagtca cccaaagtcc cacacacctg atcaaaacga gaggacagca agtgactctg     120
agatgctctc ctaagtctgg gcatgacact gtgtcctggt accaacaggc cctgggtcag     180
gggccccagt ttatctttca gtattatgag gaggaagaga gacagagagg caacttccct     240
gatcgattct caggtcacca gttccctaac tatagctctg agctgaatgt gaacgccttg     300
ttgctggggg actcggccct ctatctctgt gccagcagct tgg                        343
```

<210> SEQ ID NO 184
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 184

```
atgggccccg ggctcctctg ctgggtgctg ctttgtcccc taggagaagg cccagtggac      60
gctggagtca cccaaagtcc cacacacctg atcaaaacga gaggacagca cgtgactctg     120
agatgctctc ctatctctgg cacaccagt gtgtcctcgt accaacaggc cctgggtcag     180
gggccccagt ttatctttca gtattatgag aaagaagaga gaggaagagg aaacttccct     240
gatcaattct caggtcacca gttccctaac tatagctctg agctgaatgt gaacgccttg     300
ttgctagggg actcggccct ctatctctgt gccagcagct tgg                        343
```

<210> SEQ ID NO 185
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 185

```
atgggaccca ggctcctctt ctgggcactg ctttgtctcc tcggaacagg cccagtggag      60
gctggagtca cacaaagtcc cacacacctg atcaaaacga gaggacagca agcgactctg     120
```

```
agatgctctc ctatctctgg gcacaccagt gtgtactggt accaacaggc cctgggtctg    180
ggcctccagt tcctcctttg gtatgacgag ggtgaagaga gaaacagagg aaacttccct    240
cctagatttt caggtcgcca gttccctaat tatagctctg agctgaatgt gaacgccttg    300
gagctggagg actcggccct gtatctctgt gccagcagct tgg                      343
```

<210> SEQ ID NO 186
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 186

```
atgagcatcg ggctcctgtg ctgtgtggcc ttttctctcc tgtgggcaag tccagtgaat     60
gctggtgtca ctcagacccc aaaattccag gtcctgaaga caggacagag catgacactg    120
cagtgtgccc aggatatgaa ccataactcc atgtactggt atcgacaaga cccaggcatg    180
ggactgaggc tgatttatta ctcagcttct gagggtacca ctgacaaagg agaagtcccc    240
aatggctaca atgtctccag attaaacaaa cgggagttct cgctcaggct ggagtcggct    300
gctccctccc agacatctgt gtacttctgt gccagcagtg aagc                     344
```

<210> SEQ ID NO 187
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 187

```
atgagcctcg ggctcctgtg ctgtggggcc ttttctctcc tgtgggcagg tccagtgaat     60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctggggtt ggagtcggct    300
gctccctccc aaacatctgt gtacttctgt gccagcagtt actc                     344
```

<210> SEQ ID NO 188
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 188

```
atgagcctcg ggctcctgtg ctgtggggcc ttttctctcc tgtgggcagg tccagtgaat     60
gctggtgtca ctcagacccc aaaattccgg gtcctgaaga caggacagag catgacactg    120
ctgtgtgccc aggatatgaa ccatgaatac atgtactggt atcgacaaga cccaggcatg    180
gggctgaggc tgattcatta ctcagttggt gagggtacaa ctgccaaagg agaggtccct    240
gatggctaca atgtctccag attaaaaaaa cagaatttcc tgctggggtt ggagtcggct    300
gctccctccc aaacatctgt gtacttctgt gccagcagtt actc                     344
```

<210> SEQ ID NO 189
<211> LENGTH: 344
<212> TYPE: DNA

<213> ORGANISM: Artificial Sequence
<220> FEATURE:
<223> OTHER INFORMATION: Synthetic Polynucleotide

<400> SEQUENCE: 189

```
atgagaatca ggctcctgtg ctgtgtggcc ttttctctcc tgtgggcagg tccagtgatt      60
gctgggatca cccaggcacc aacatctcag atcctggcag caggacggcg catgacactg     120
agatgtaccc aggatatgag acataatgcc atgtactggt atagacaaga tctaggactg     180
gggctaaggc tcatccatta ttcaaatact gcaggtacca ctggcaaagg agaagtccct     240
gatggttata gtgtctccag agcaaacaca gatgatttcc ccctcacgtt ggcgtctgct     300
gtaccctctc agacatctgt gtacttctgt gccagcagtg actc                      344
```

<210> SEQ ID NO 190
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 190

```
atgagcatcg gcctcctgtg ctgtgcagcc ttgtctctcc tgtgggcagg tccagtgaat      60
gctggtgtca ctcagacccc aaaattccag gtcctgaaga caggacagag catgacactg     120
cagtgtgccc aggatatgaa ccatgaatac atgtcctggt atcgacaaga cccaggcatg     180
gggctgaggc tgattcatta ctcagttggt gctggtatca ctgaccaagg agaagtcccc     240
aatggctaca atgtctccag atcaaccaca gaggatttcc cgctcaggct gctgtcggct     300
gctccctccc agacatctgt gtacttctgt gccagcagtt actc                      344
```

<210> SEQ ID NO 191
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 191

```
atgagcatca gcctcctgtg ctgtgcagcc tttcctctcc tgtgggcagg tccagtgaat      60
gctggtgtca ctcagacccc aaaattccgc atcctgaaga taggacagag catgacactg     120
cagtgtaccc aggatatgaa ccataactac atgtactggt atcgacaaga cccaggcatg     180
gggctgaagc tgatttatta ttcagttggt gctggtatca ctgataaagg agaagtcccg     240
aatggctaca acgtctccag atcaaccaca gaggattccc cgctcaggct ggagttggct     300
gctccctccc agacatctgt gtacttctgt gccagcagtt actc                      344
```

<210> SEQ ID NO 192
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 192

```
atgagcctcg ggctcctgtg ctgtgtggcc ttttctctcc tgtgggcagg tccaatgaat      60
gctggtgtca ctcagacccc aaaattccac gtcctgaaga caggacagag catgactctg     120
ctgtgtgccc aggatatgaa ccatgaatac atgtatcggt atcgacaaga cccaggcaag     180
gggctgaggc tgatttacta ctcagttgct gctgctctca ctgacaaagg agaagttccc     240
```

-continued

```
aatggctaca atgtctccag atcaaacaca gaggatttcc ccctcaagct ggagtcagct    300
gctccctctc agacttctgt ttacttctgt gccagcagtt actc                    344

<210> SEQ ID NO 193
<211> LENGTH: 341
<212> TYPE: DNA
<213> ORGANISM: Artificial Sequence
<220> FEATURE:
<223> OTHER INFORMATION: Synthetic Polynucleotide

<400> SEQUENCE: 193
atgagcctcg ggctcctgtg ctgtgcggcc ttttctctcc tgtgggcagg tcccgtgaat    60
gctggtgtca ctcagacccc aaaattccac atcctgaaga caggacagag catgacactg    120
cagtgtgccc aggatatgaa ccatggatac atgtcctggt atcgacaaga cccaggcatg    180
gggctgagac tgatttacta ctcagctgct gctggtacta ctgacaaaga agtccccaat    240
ggctacaatg tctctagatt aaacacagag gatttcccac tcaggctggt gtcggctgct    300
ccctcccaga catctgtgta cttgtgtgcc agcagttact c                       341

<210> SEQ ID NO 194
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 194
atgagcatcg ggctcctgtg ctgtgtggcc ttttctctcc tgtgggaggg tccagtgaat    60
gctggtgtca ctcagacccc aaaattccac atcctgaaga caggacagag catgacactg    120
cagtgtgccc aggatatgaa ccatggatac ttgtcctggt atcgacaaga cccaggcatg    180
gggctgaggc gcattcatta ctcagttgct gctggtatca ctgacaaagg agaagtcccc    240
gatggctaca atgtatccag atcaaacaca gaggatttcc cgctcaggct ggagtcagct    300
gctccctccc agacatctgt atacttctgt gccagcagtt attc                    344

<210> SEQ ID NO 195
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 195
atgggcacaa ggctcctctg ctgggcagcc atatgtctcc tggggcaga tcacacaggt     60 gctggagtct cccagtccct gagacacaag gtagcaaaga agggaaagga tgtagctctc    120
agatatgatc caatttcagg tcataatgcc ctttattggt accgacagag cctggggcag    180
ggcctggagt ttccaattta cttccaaggc aaggatgcag cagacaaatc ggggcttccc    240
cgtgatcggt tctctgcaca gaggtctgag ggatccatct ccactctgaa gttccagcgc    300
acacagcagg gggacttggc tgtgtatctc tgtgccagca gctcagc                 347

<210> SEQ ID NO 196
<211> LENGTH: 347
<212> TYPE: DNA
<213> ORGANISM: Artificial Sequence
<220> FEATURE:
<223> OTHER INFORMATION: Synthetic Polynucleotide
```

<400> SEQUENCE: 196

```
atgggcacca ggctcctctt ctgggtggcc ttctgtctcc tgggggcaga tcacacagga      60
gctggagtct cccagtcccc cagtaacaag gtcacagaga agggaaagga tgtagagctc     120
aggtgtgatc caatttcagg tcatactgcc ctttactggt accgacagag cctggggcag     180
ggcctggagt ttttaattta cttccaaggc aacagtgcac cagacaaatc agggctgccc     240
agtgatcgct ctctgcaga gaggactggg ggatccgtct ccactctgac gatccagcgc      300
acacagcagg aggactcggc cgtgtatctc tgtgccagca gcttagc                   347
```

<210> SEQ ID NO 197
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 197

```
atgggcacca ggctcctctg ctgggcagcc ctgtgcctcc tgggggcaga tcacacaggt      60
gctggagtct cccagacccc cagtaacaag gtcacagaga agggaaaata tgtagagctc     120
aggtgtgatc caatttcagg tcatactgcc ctttactggt accgacaaag cctggggcag     180
ggcccagagt ttctaattta cttccaaggc acgggtgcgg cagatgactc agggctgccc     240
aacgatcggt tctttgcagt caggcctgag ggatccgtct ctactctgaa gatccagcgc     300
acagagcggg gggactcagc cgtgtatctc tgtgccagca gcttaac                   347
```

<210> SEQ ID NO 198
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 198

```
atgggcacca ggctcctctg ctgggtggtc ctgggtttcc tagggacaga tcacacaggt      60
gctggagtct cccagtcccc aaggtacaaa gtcgcaaaga ggggacggga tgtagctctc     120
aggtgtgatt caatttcggg tcatgtaacc ctttattggt accgacagac cctggggcag     180
ggctcagagg ttctgactta ctcccagagt gatgctcaac gagacaaatc agggcggccc     240
agtggtcggt tctctgcaga gaggcctgag agatccgtct ccactctgaa gatccagcgc     300
acagagcagg gggactcagc tgtgtatctc tgtgccagca gcttagc                   347
```

<210> SEQ ID NO 199
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 199

```
atgggcacca ggctcctctg ctgggtggtc ctgggtttcc tagggacaga tcacacaggt      60
gctggagtct cccagtcccc aaggtacgaa gtcacacaga ggggacagga tgtagctccc     120
aggtgtgatc caatttcggg tcaggtaacc ctttattggt accgacagac cctggggcag     180
ggccaagagt ttctgacttc cttccaggat gaaactcaac aagataaatc agggctgctc     240
agtgatcaat tctccacaga gaggtctgag gatctttctc cacctgaaga tccagcgcac     300
agagcaaggg cgactcggct gtgtatctct gtgccagaag cttag                     345
```

<210> SEQ ID NO 200
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 200

```
atgggcacca gtctcctatg ctgggtggtc ctgggtttcc tagggacaga tcacacaggt      60
gctggagtct cccagtctcc caggtacaaa gtcacaaaga ggggacagga tgtagctctc     120
aggtgtgatc caatttcggg tcatgtatcc ctttattggt accgacaggc cctggggcag     180
ggcccagagt ttctgactta cttcaattat gaagcccaac aagacaaatc agggctgccc     240
aatgatcggt tctctgcaga gaggcctgag ggatccatct ccactctgac gatccagcgc     300
acagagcagc gggactcggc catgtatcgc tgtgccagca gcttagc                   347
```

<210> SEQ ID NO 201
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 201

```
atgggtacca gtctcctatg ctgggtggtc ctgggtttcc tagggacaga tcacacaggt      60
gctggagtct cccagtctcc caggtacaaa gtcacaaaga ggggacagga tgtaactctc     120
aggtgtgatc caatttcgag tcatgcaacc ctttattggt atcaacaggc cctggggcag     180
ggcccagagt ttctgactta cttcaattat gaagctcaac cagacaaatc agggctgccc     240
agtgatcggt tctctgcaga gaggcctgag ggatccatct ccactctgac gattcagcgc     300
acagagcagc gggactcagc catgtatcgc tgtgccagca gcttagc                   347
```

<210> SEQ ID NO 202
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 202

```
atgggcacca ggctcctctg ctgggtggtc ctgggtttcc tagggacaga tcacacaggt      60
gctggagtct cccagtcccc taggtacaaa gtcgcaaaga gaggacagga tgtagctctc     120
aggtgtgatc caatttcggg tcatgtatcc cttttttggt accaacaggc cctggggcag     180
gggccagagt ttctgactta tttccagaat gaagctcaac tagacaaatc ggggctgccc     240
agtgatcgct tctttgcaga aaggcctgag ggatccgtct ccactctgaa gatccagcgc     300
acacagcagg aggactccgc cgtgtatctc tgtgccagca gcttagc                   347
```

<210> SEQ ID NO 203
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 203

```
atgggcacca gcctcctctg ctggatggcc ctgtgtctcc tgggggcaga tcacgcagat      60
```

```
actggagtct cccagaaccc cagacacaag atcacaaaga ggggacagaa tgtaactttc      120
aggtgtgatc caatttctga acacaaccgc ctttattggt accgacagac cctggggcag      180
ggcccagagt ttctgactta cttccagaat gaagctcaac tagaaaaatc aaggctgctc      240
agtgatcggt tctctgcaga gaggcctaag ggatctttct ccaccttgga gatccagcgc      300
acagagcagg gggactcggc catgtatctc tgtgccagca gcttagc                   347

<210> SEQ ID NO 204
<211> LENGTH: 279
<212> TYPE: DNA
<213> ORGANISM: Artificial Sequence
<220> FEATURE:
<223> OTHER INFORMATION: Synthetic Polynucleotide

<400> SEQUENCE: 204
gaggcaggga tcagccagat accaagatat cacagacaca cagggaaaaa gatcatcctg       60
aaatatgctc agattaggaa ccattattca gtgttctgtt atcaataaga ccaagaatag      120
gggctgaggc tgatccatta ttcaggtagt attggcagca tgaccaaagg cggtgccaag      180
gaagggtaca atgtctctgg aaacaagctc aagcattttc cctcaaccct ggagtctact      240
agcaccagcc agacctctgt acctctgtgg cagtgcatc                             279

<210> SEQ ID NO 205
<211> LENGTH: 325
<212> TYPE: DNA
<213> ORGANISM: Artificial Sequence
<220> FEATURE:
<223> OTHER INFORMATION: Synthetic Polynucleotide

<400> SEQUENCE: 205
atgaacccca aactcttctg tgtgacccct tgtctcctgg gagcaggctc tattgatgct       60
gggatcaccc agatgccaag atatcacatt gtacagaaga aagagatgat cctggaatgt      120
gctcaggtta ggaacagtgt tctgatatcg acaggaccca gacgggggc tgaagcttat      180 ccactattca ggcagtggtc acagcaggac caaagttgat gtcacagagg ggtactgtgt      240
ttcttgaaac aagcttgagc atttccccaa tcctggcatc caccagcacc agccagacct      300
atctgtacca ctgtggcagc acatc                                            325

<210> SEQ ID NO 206
<211> LENGTH: 343
<212> TYPE: DNA
<213> ORGANISM: Artificial Sequence
<220> FEATURE:
<223> OTHER INFORMATION: Synthetic Polynucleotide

<400> SEQUENCE: 206
atgggcttca ggctcctctg ctgtgtggcc ttttgtctcc tgggagcagg cccagtggat       60
tctggagtca cacaaacccc aaagcacctg atcacagcaa ctggacagcg agtgacgctg      120
agatgctccc ctaggtctgg agacctctct gtgtactggt accaacagag cctggaccag      180
ggcctccagt tcctcattca gtattataat ggagaagaga gagcaaaagg aaacattctt      240
gaacgattct ccgcacaaca gttccctgac ttgcactctg aactaaacct gagctctctg      300
gagctggggg actcagcttt gtatttctgt gccagcagcg tag                        343

<210> SEQ ID NO 207
<211> LENGTH: 344
<212> TYPE: DNA
<213> ORGANISM: Artificial Sequence
```

```
<220> FEATURE:
<223> OTHER INFORMATION: Synthetic Polynucleotide

<400> SEQUENCE: 207
atgggcacga ggctcttctt ctatgtggcc ctttgtctgc tgtgggcagg acacagggat      60
gctgaaatca cccagagccc aagacacaag atcacagaga caggaaggca ggtgaccttg     120
gcgtgtcacc agacttggaa ccacaacaat atgttctggt atcgacaaga cctgggacat     180
gggctgaggc tgatccatta ctcatatggt gttcaagaca ctaacaaagg agaagtctca     240
gatggctaca gtgtctctag atcaaacaca gaggacctcc ccctcactct ggagtctgct     300
gcctcctccc agacatctgt atatttctgc gccagcagtg agtc                      344

<210> SEQ ID NO 208
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 208
atgggcacca ggctcttctt ctatgtggcc ctttgtctgc tgtgggcagg acacagggat      60
gctggaatca cccagagccc aagatacaag atcacagaga caggaaggca ggtgaccttg     120
atgtgtcacc agacttggag ccacagctat atgttctggt atcgacaaga cctgggacat     180
gggctgaggc tgatctatta ctcagcagct gctgatatta cagataaagg agaagtcccc     240
gatggctatg ttgtctccag atccaagaca gagaatttcc ccctcactct ggagtcagct     300
acccgctccc agacatctgt gtatttctgc gccagcagtg agtc                      344

<210> SEQ ID NO 209
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 209
atgggcacaa ggttgttctt ctatgtggcc ctttgtctcc tgtggacagg acacatggat      60
gctggaatca cccagagccc aagacacaag gtcacagaga caggaacacc agtgactctg     120
agatgtcacc agactgagaa ccaccgctat atgtactggt atcgacaaga cccggggcat     180
gggctgaggc tgatccatta ctcatatggt gttaaagata ctgacaaagg agaagtctca     240
gatggctata gtgtctctag atcaaagaca gaggatttcc tcctcactct ggagtccgct     300
accagctccc agacatctgt gtacttctgt gccatcagtg agtc                      344

<210> SEQ ID NO 210
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 210
atgagcacca ggcttctctg ctggatggcc ctctgtctcc tggggcaga actctcagaa       60 gctgaagttg cccagtcccc cagatataag attacagaga aagccaggc tgtggctttt      120 tggtgtgatc ctatttctgg ccatgctacc ctttactggt accggcagat cctgggacag     180
ggcccggagc ttctggttca atttcaggat gagagtgtag tagatgattc acagttgcct     240
```
aaggatcgat tttctgcaga gaggctcaaa ggagtagact ccactctcaa gatccagcct    300
gcagagcttg gggactcggc catgtatctc tgtgccagca gcttagc                 347

<210> SEQ ID NO 211
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 211
atgggcacca ggctcctctg ctgggcggcc ctctgtctcc tgggagcaga actcacagaa    60
gctggagttg cccagtctcc cagatataag attatagaga aaaggcagag tgtggctttt    120
tggtgcaatc ctatatctgg ccatgctacc ctttactggt accagcagat cctgggacag    180
ggcccaaagc ttctgattca gtttcagaat aacggtgtag tggatgattc acagttgcct    240
aaggatcgat tttctgcaga gaggctcaaa ggagtagact ccactctcaa gatccagcct    300
gcaaagcttg aggactcggc cgtgtatctc tgtgccagca gcttaga                 347

<210> SEQ ID NO 212
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 212
atgggtacca ggctcctctg ctgggtggcc ttctgtctcc tggtggaaga actcatagaa    60
gctggagtgg ttcagtctcc cagatataag attatagaga aaaacagcc tgtggctttt    120 tggtgcaatc ctatttctgg ccacaatacc ctttactggt acctgcagaa cttgggacag    180
ggcccggagc ttctgattcg atatgagaat gaggaagcag tagacgattc acagttgcct    240
aaggatcgat tttctgcaga gaggctcaaa ggagtagact ccactctcaa gatccagcct    300
gcagagcttg gggactcggc cgtgtatctc tgtgccagca gcttaga                 347

<210> SEQ ID NO 213
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 213
atgggctctt ggaccctctg tgtgtcccct tatatcctgg tagcgacaca cacagatgct    60
ggtgttatcc agtcacccag gcacaaagtg acagagatgg gacaatcagt aactctgaga    120
tgcgaaccaa tttcaggcca caatgatctt ctctggtaca gacagacctt gtgcaggga    180 ctggaattgc tgaattactt ctgcagctgg accctcgtag atgactcagg agtgtccaag    240
gattgattct cagcacagat gcctgatgta tcattctcca ctctgaggat ccagcccatg    300
gaacccaggg acttgggcct atatttctgt gccagcagct ttgc                    344

<210> SEQ ID NO 214
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 214

```
atggactcct ggaccctctg tgtgtccctt tgtatcctgg tagcgacatg cacagatgct    60
ggcattatcc agtcacccaa gcatgaggtg acagaaatgg acaaacagt gactctgaga    120 tgtgagccaa tttttggcca caatttcctt ttctggtaca gagatacctt cgtgcaggga   180
ctggaattgc tgagttactt ccggagctga tctattatag ataatgcagg tatgcccaca   240
gagcgattct cagctgagag gcctgatgga tcattctcta ctctgaagat ccagcctgca   300 gagcagggg actcggccgt gtatgtctgt gcaagtcgct agc                       344
```

<210> SEQ ID NO 215
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 215

```
atggactcct ggaccttctg ctgtgtgtcc ctttgcatcc tggtagcgaa gcatacagat    60
gctggagtta tccagtcacc ccgccatgag gtgacagaga tgggacaaga agtgactctg   120
agatgtaaac caatttcagg ccacaactcc cttttctggt acagacagac catgatgcgg   180
ggactggagt tgctcattta ctttaacaac aacgttccga tagatgattc agggatgccc   240
gaggatcgat tctcagctaa gatgcctaat gcatcattct ccactctgaa gatccagccc   300
tcagaaccca gggactcagc tgtgtacttc tgtgccagca gtttagc                  347
```

<210> SEQ ID NO 216
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 216

```
atgggctcct ggaccctctg ctgtgtgtcc ctttgcatcc tggtagcaaa gcacacagat    60
gctggagtta tccagtcacc ccggcacgag gtgacagaga tgggacaaga agtgactctg   120
agatgtaaac caatttcagg acacgactac cttttctggt acagacagac catgatgcgg   180
ggactggagt tgctcattta ctttaacaac aacgttccga tagatgattc agggatgccc   240
gaggatcgat tctcagctaa gatgcctaat gcatcattct ccactctgaa gatccagccc   300
tcagaaccca gggactcagc tgtgtacttc tgtgccagca gtttagc                  347
```

<210> SEQ ID NO 217
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 217

```
atggccacca ggctcctctg ctgtgtggtt ctttgtctcc tgggagaaga gcttatagat    60
gctagagtca cccagacacc aaggcacaag gtgacagaga tgggacaaga agtaacaatg   120
agatgtcagc caatttagg ccacaatact gttttctggt acagacagac catgatgcaa    180
ggactggagt tgctggctta cttccgcaac cgggctcctc tagatgattc ggggatgccg    240
aaggatcgat tctcagcaga gatgcctgat gcaactttag ccactctgaa gatccagccc    300
tcagaaccca gggactcagc tgtgtatttt tgtgctagtg gtttggt                  347
```

<210> SEQ ID NO 218
<211> LENGTH: 374
<212> TYPE: DNA
<213> ORGANISM: Artificial Sequence
<220> FEATURE:
<223> OTHER INFORMATION: Synthetic Polynucleotide

<400> SEQUENCE: 218

```
atgcttagtc ctgacctgcc tgactctgcc tggaacacca ggctcctctg ccatgtcatg      60
ctttgtctcc tgggagcagt ttcagtggct gctggagtca tccagtcccc aagacatctg     120
atcaaagaaa agagggaaac agccactctg aaatgctatc ctatccctag acacgacact     180
gtctactggt accagcaggg tccaggtcag accccagt tcctcatttc gttttatgaa       240
aagatgcaga gcgataaagg aagcatccct gatcgattct cagctcaaca gttcagtgac     300
tatcattctg aactgaacat gagctccttg gagctggggg actcagccct gtacttctgt     360
gccagcagct tagg                                                       374
```

<210> SEQ ID NO 219
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 219

```
atggtttcca ggcttctcag tttagtgtcc ctttgtctcc tgggagcaaa gcacatagaa      60
gctggagtta ctcagttccc cagccacagc gtaatagaga agggccagac tgtgactctg     120
agatgtgacc caatttctgg acatgataat ctttattggt atcgacgtgt tatgggaaaa     180
gaaataaaat ttctgttaca ttttgtgaaa gagtctaaac aggatgagtc cggtatgccc     240
aacaatcgat tcttagctga aaggactgga gggacgtatt ctactctgaa ggtgcagcct     300
gcagaactgg aggattctgg agtttatttc tgtgccagca gccaaga                   347
```

<210> SEQ ID NO 220
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 220

```
atgggtcctg ggcttctcca ctggatggcc ctttgtctcc ttggaacagg tcatgggat       60 gccatggtca tccagaaccc aagataccag gttacccagt ttggaaagcc agtgaccctg     120
agttgttctc agactttgaa ccataacgtc atgtactggt accagcagaa gtcaagtcag     180
gccccaaagc tgctgttcca ctactatgac aaagatttta acaatgaagc agacaccct     240 gataacttcc aatccaggag gccgaacact tctttctgct tcttgacat ccgctcacca      300 ggcctggggg acacagccat gtacctgtgt gccaccagca gaga                      344
```

<210> SEQ ID NO 221
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 221

```
atgagcccaa tattcacctg catcacaatc ctttgtctgc tggctgcagg ttctcctggt      60
```

```
gaagaagtcg cccagactcc aaaacatctt gtcagagggg aaggacagaa agcaaaatta      120
tattgtgccc aataaaagg acacagttat gttttttggt accaacaggt cctgaaaaac       180
gagttcaagt tcttgatttc cttccagaat gaaaatgtct ttgatgaaac aggtatgccc      240
aaggaaagat tttcagctaa gtgcctccca aattcaccct gtagccttga gatccaggct      300
acgaagcttg aggattcagc agtgtatttt tgtgccagca gccaatc                   347

<210> SEQ ID NO 222
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 222
atggatatct ggctcctctg ctgggtgacc ctgtgtctct tggcggcagg acactcggag       60
cctggagtca gccagacccc cagacacaag gtcaccaaca tgggacagga ggtgattctg      120
aggtgcgatc catcttctgg tcacatgttt gttcactggt accgacagaa tctgaggcaa      180
gaaatgaagt tgctgatttc cttccagtac caaaacattg cagttgattc agggatgccc      240
aaggaacgat tcacagctga agacctaacg gaacgtctt ccacgctgaa gatccatccc       300
gcagagccga gggactcagc cgtgtatctc tacagtagcg gtgg                       344

<210> SEQ ID NO 223
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 223
atggacacca gagtactctg ctgtgcggtc atctgtcttc tgggggcagg tctctcaaat       60
gccggcgtca tgcagaaccc aagacacctg gtcaggagga ggggacagga ggcaagactg      120
agatgcagcc caatgaaagg acacagtcat gtttactggt atcggcagct cccagaggaa      180
ggtctgaaat tcatggttta tctccagaaa gaaaatatca tagatgagtc aggaatgcca      240
aaggaacgat tttctgctga atttcccaaa gagggcccca gcatcctgag gatccagcag      300
gtagtgcgag gagattcggc agcttatttc tgtgccagct caccacc                    347

<210> SEQ ID NO 224
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 224
atgagcaacc aggtgctctg ctgtgtggtc ctttgtttcc tgggagcaaa caccgtggat       60
ggtggaatca ctcagtcccc aaagtacctg ttcagaaagg aaggacagaa tgtgaccctg      120
agttgtgaac agaatttgaa ccacgatgcc atgtactggt accgacagga cccagggcaa      180
gggctgagat tgatctacta ctcacagata gtaaatgact ttcagaaagg agatatagct      240
gaagggtaca gcgtctctcg ggagaagaag gaatcctttc ctctcactgt gacatcggcc      300
caaaagaacc cgacagcttt ctatctctgt gccagtagta taga                       344

<210> SEQ ID NO 225
```

```
<211> LENGTH: 368
<212> TYPE: DNA
<213> ORGANISM: Artificial Sequence
<220> FEATURE:
<223> OTHER INFORMATION: Synthetic Polynucleotide

<400> SEQUENCE: 225
atgctgctgc ttctgctgct tctggggcca ggtataagcc tccttctacc tgggagcttg      60
gcaggctccg ggcttggtgc tgtcgtctct caacatccga gctgggttat ctgtaagagt     120
ggaacctctg tgaagatcga gtgccgttcc ctggactttc aggccacaac tatgttttgg     180
tatcgtcagt tcccgaaaca gagtctcatg ctgatggcaa cttccaatga gggctccaag     240
gccacatacg agcaaggcgt cgagaaggac aagtttctca tcaaccatgc aagcctgacc     300
ttgtccactc tgacagtgac cagtgcccat cctgaagaca gcagcttcta catctgcagt     360
gctagaga                                                              368

<210> SEQ ID NO 226
<211> LENGTH: 348
<212> TYPE: DNA
<213> ORGANISM: Artificial Sequence
<220> FEATURE:
<223> OTHER INFORMATION: Synthetic Polynucleotide

<400> SEQUENCE: 226
atgtgcctca gacttctctg ctgtgtggcc atttctttct ggggagccag gctccacgga      60
caccaaggtc acccagagac ctagacttct ggtcaaagca agtgaacaga aagcaaagat     120
ggattgtgtt cctataaaag cacatagtta tgtttactgg tatcgtaaga agctggaaga     180
agagctcaag ttttggtttt actttcagaa tgaagaactt attcagaaag cagaaataat     240
caatgagcga tttttagccc aatgctccaa aaactcatcc tgtaccttgg agatccagtc     300
cacggagtca ggggacacag cactgtattt ctgtgccagc agcaaagc                  348

<210> SEQ ID NO 227
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 227
atggggagct gggtcctctg ctatgtgacc ctgtgtctcc tgggagcagg acccttggat      60
gctgacatct atcagatgcc attccagctc actggggctg gatgggatgt gactctggag     120
tggaaacgga atttgagaca caatgacatg tactgctact ggtactggca ggacccaaag     180
caaaatctga gactgatcta ttactcaagg gttgaaaagg atattcagag aggagatcta     240
actgaaggct acgtgtctgc caagaggaga agggctatt tcttctcagg gtgaagttgg      300
cccacaccag ccaaacagct ttgtacttct gtcctgggag cgcac                     345

<210> SEQ ID NO 228
<211> LENGTH: 347
<212> TYPE: DNA
<213> ORGANISM: Artificial Sequence
<220> FEATURE:
<223> OTHER INFORMATION: Synthetic Polynucleotide

<400> SEQUENCE: 228
atgggcacca ggctcctcgg ctgtgcagcc ctgtgtctcc tggcagcaga ctcttttcat      60
gccaaagtca cacagactcc aggacatttg gtcaaaggaa aaggacagaa aacaaagatg     120
```

```
gattgtaccc ccgaaaaagg acatactttt gtttattggt atcaacagaa tcagaataaa    180
gagtttatgc ttttgatttc ctttcagaat gaacaagttc ttcaagaaac ggagatgcac    240
aagaagcgat tctcatctca atgccccaag aacgcaccct gcagcctggc aatcctgtcc    300
tcagaaccgg agacacggc actgtatctc tgcgccagca gtcaatc                    347
```

<210> SEQ ID NO 229
<211> LENGTH: 345
<212> TYPE: DNA
<213> ORGANISM: Artificial Sequence
<220> FEATURE:
<223> OTHER INFORMATION: Synthetic Polynucleotide

<400> SEQUENCE: 229

```
atggcctccc tgctcttctt ctgtggggcc ttttatctcc tgggaacagg gtccatggat     60
gctgatgtta cccagacccc aaggaatagg atcacaaaga caggaaagag gattatgctg    120
gaatgttctc agactaaggg tcatgataga atgtactggt atcgacaaga cccaggactg    180
ggcctacggt tgatctatta ctcctttgat gtcaaagata taaacaaagg agagatctct    240
gatggataca gtgtctctcg acaggcacag gctaaattct ccctgtccct agagtctgcc    300
atccccaacc agacagctct ttacttctgt gccaccagtg atttg                    345
```

<210> SEQ ID NO 230
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 230

```
atgactatca ggctcctctg ctacatgggc ttttattttc tggggcagg cctcatggaa      60 gctgacatct accagacccc aagataccct gttataggga caggaaagaa gatcactctg    120
gaatgttctc aaaccatggg ccatgacaaa atgtactggt atcaacaaga tccaggaatg    180
gaactacacc tcatccacta ttcctatgga gttaattcca cagagaaggg agatctttcc    240
tctgagtcaa cagtctccag aataaggacg gagcattttc ccctgaccct ggagtctgcc    300
aggccctcac atacctctca gtacctctgt gccagcagtg aata                     344
```

<210> SEQ ID NO 231
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 231

```
atgagcaaca ggcttctctg ctgtgtgatc atttgtctcc taagagcagg cctcaaggat      60
gctgtagtta cacaattccc aagacacaga atcattggga caggaaagga attcattcta    120
cagtgttccc agaatatgaa tcatgttaca atgtactggt atcgacagga cccaggactt    180
ggactgaagc tggtctatta ttcacctggc actgggagca ctgaaaaagg agatatctct    240
gaggggtatc atgtttcttg aaatactata gcatctttc ccctgaccct gaagtctgcc    300
agcaccaacc agacatctgt gtatctctat gccagcagtt catc                     344
```

<210> SEQ ID NO 232
<211> LENGTH: 344
<212> TYPE: DNA

```
<213> ORGANISM: Artificial Sequence
<220> FEATURE:
<223> OTHER INFORMATION: Synthetic Polynucleotide

<400> SEQUENCE: 232
atgggccccc agctccttgg ctatgtggtc ctttgccttc taggagcagg ccccctggaa      60
gcccaagtga cccagaaccc aagatacctc atcacagtga ctggaaagaa gttaacagtg     120
acttgttctc agaatatgaa ccatgagtat atgtcctggt atcgacaaga cccagggctg     180
ggcttaaggc agatctacta ttcaatgaat gttgaggtga ctgataaggg agatgttcct     240
gaagggtaca aagtctctcg aaaagagaag aggaatttcc ccctgatcct ggagtcgccc     300
agccccaacc agacctctct gtacttctgt gccagcagtt tatc                      344

<210> SEQ ID NO 233
<211> LENGTH: 344
<212> TYPE: DNA
<213> ORGANISM: Artificial Sequence
<220> FEATURE:
<223> OTHER INFORMATION: Synthetic Polynucleotide

<400> SEQUENCE: 233
atgggaatca ggctcctgtg tcgtgtggcc ttttgtttcc tggctgtagg cctcgtagat      60
gtgaaagtaa cccagagctc gagatatcta gtcaaaagga cgggagagaa agttttttctg   120 gaatgtgtcc aggatatgga ccatgaaaat atgttctggt atcgacaaga cccaggtctg     180
gggctacggc tgatctattt ctcatatgat gttaaaatga agaaaaagg agatattcct      240 gagggggtaca gtgtctctag agagaagaag gagcgcttct ccctgattct ggagtccgcc   300
agcaccaacc agacatctat gtacctctgt gccagcagtt tatg                      344

<210> SEQ ID NO 234
<211> LENGTH: 335
<212> TYPE: DNA
<213> ORGANISM: Artificial Sequence
<220> FEATURE:
<223> OTHER INFORMATION: Synthetic Polynucleotide

<400> SEQUENCE: 234
atgctgagtc ttctgctcct tctcctggga ctaggctctg tgttcagtgc tgtcatctct      60
caaaagccaa gcagggatat ctgtcaacgt ggaacctccc tgacgatcca gtgtcaagtc     120
gatagccaag tcaccatgat gttctggtac cgtcagcaac ctggacagag cctgacactg     180
atcgcaactg caaatcaggg ctctgaggcc acatatgaga gtggatttgt cattgacaag     240
tttcccatca gccgcccaaa cctaacattc tcaactctga ctgtgagcaa catgagccct     300
gaagacagca gcatatatct ctgcagcgtt gaaga                                335

<210> SEQ ID NO 235
<211> LENGTH: 335
<212> TYPE: DNA
<213> ORGANISM: Artificial Sequence
<220> FEATURE:
<223> OTHER INFORMATION: Synthetic Polynucleotide

<400> SEQUENCE: 235
atgctctgct ctctccttgc ccttctcctg ggcactttct ttggggtcag atctcagact      60
attcatcaat ggccagcgac cctggtgcag cctgtgggca gccgctctc tctggagtgc     120 actgtgagg gaacatcaaa ccccaaccta tactggtacc gacaggctgc aggcaggggc     180
ctccagctgc tcttctactc cgttggtatt ggccagatca gctctgaggt gccccagaat    240
```

```
ctctcagcct ccagacccca ggaccggcag ttcatcctga gttctaagaa gctccttctc    300
agtgactctg gcttctatct ctgtgcctgg agtgt                               335
```

<210> SEQ ID NO 236
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 236

```
Thr Glu Asp Tyr Met Ile His Ile Ile
1               5
```

<210> SEQ ID NO 237
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 237

```
Cys Ala Ser Ser Arg His Val Gly Gly Val Pro Glu Ala Phe Phe Gly
1               5                   10                  15
```

<210> SEQ ID NO 238
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 238

```
Cys Ala Ser Ser Ile Gly Arg Gly Ser Glu Gln Tyr Phe Gly
1               5                   10
```

<210> SEQ ID NO 239
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 239

```
Cys Ala Ser Ser Asp Val Leu Ser Gly Glu Ala Phe Phe Gly
1               5                   10
```

<210> SEQ ID NO 240
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 240

```
Cys Ala Ser Gln Gly His Lys Asn Thr Glu Ala Phe Phe Gly
1               5                   10
```

<210> SEQ ID NO 241
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 241

Cys Ala Ser Ser Leu Gly Pro Gly Gly Val Lys Thr Asn Glu Lys Leu
1               5                   10                  15

Phe Phe Gly

<210> SEQ ID NO 242
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 242

Cys Ala Ser Ser Leu Gly Pro Gly Gly Val Lys Thr Asn Glu Lys Leu
1               5                   10                  15

Phe Phe Gly

<210> SEQ ID NO 243
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 243

Cys Ala Ser Ser Asp Val Leu Ser Gly Glu Ala Phe Phe Gly
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 244

Cys Ala Ser Gln Gly His Lys Asn Thr Glu Ala Phe Phe Gly
1               5                   10

<210> SEQ ID NO 245
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 245

Cys Ala Ser Ser Leu Gly Pro Gly Gly Val Lys Thr Asn Glu Lys Leu
1               5                   10                  15

Phe Phe Gly

<210> SEQ ID NO 246
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 246

Cys Ala Ser Ser Ile Gly Arg Gly Ser Glu Gln Tyr Phe Gly
1               5                   10

<210> SEQ ID NO 247
<211> LENGTH: 16
<212> TYPE: PRT

```
<213> ORGANISM: Artificial Sequence
<220> FEATURE:
<223> OTHER INFORMATION: Synthetic Polypeptide

<400> SEQUENCE: 247

Cys Ala Ser Ser Arg His Val Gly Gly Val Pro Glu Ala Phe Phe Gly
1               5                   10                  15

<210> SEQ ID NO 248
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 248

Cys Ala Ser Ser Ala Ser Lys Gly Gln Pro Gln His Phe Gly
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 249

Cys Ala Ser Gln Gly His Lys Asn Thr Glu Ala Phe Phe Gly
1               5                   10

<210> SEQ ID NO 250
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 250

Cys Ala Ser Ser Leu Gly Pro Gly Gly Val Lys Thr Asn Glu Lys Leu
1               5                   10                  15

Phe Phe Gly

<210> SEQ ID NO 251
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 251
aaacgacggc cagtgaattg taatacgact cactataggc gct                    43

<210> SEQ ID NO 252
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 252
ggccagtgaa ttgtaatacg actcactata gggaggcggt                        40

<210> SEQ ID NO 253
<211> LENGTH: 27
<212> TYPE: DNA
<213> ORGANISM: Artificial Sequence
```

```
<220> FEATURE:
<223> OTHER INFORMATION: Synthetic Polynucleotide

<400> SEQUENCE: 253
taatacgact cactataggg aggcggt                                              27

<210> SEQ ID NO 254
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 254
ggtaatacga ctcactatag ggagaagagt                                           30

<210> SEQ ID NO 255
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 255
aattaatacg actcactata gggagat                                              27

<210> SEQ ID NO 256
<211> LENGTH: 14
<212> TYPE: DNA
<213> ORGANISM: Artificial Sequence
<220> FEATURE:
<223> OTHER INFORMATION: Synthetic polynucleotide

<400> SEQUENCE: 256
tcgtcggcag cgtc                                                            14

<210> SEQ ID NO 257
<211> LENGTH: 58
<212> TYPE: DNA
<213> ORGANISM: Artificial Sequence
<220> FEATURE:
<223> OTHER INFORMATION: Synthetic polynucleotide

<400> SEQUENCE: 257
gtctcgtggg ctcggagatg tgtataagag acaggaatca aaatcggtga ataggcag            58

<210> SEQ ID NO 258
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 258
gtctcgtggg ctcggagatg tgtataagag acaggccagg cacaccagtg tggcctttt          59

<210> SEQ ID NO 259
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 259
caagcagaag acggcatacg agatgtctcg tgggctc                                   37
```

<210> SEQ ID NO 260
<211> LENGTH: 41
<212> TYPE: DNA
<213> ORGANISM: Artificial Sequence
<220> FEATURE:
<223> OTHER INFORMATION: Synthetic polynucleotide

<400> SEQUENCE: 260
aatgatacgg cgaccaccga gatctacact cgtcggcagc g           41

<210> SEQ ID NO 261
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 261
tcgtcggcag cgtcagatgt gtataagaga caghhhhhnn nncttctaca ggagctccag    60
atgaaag                                                              67

<210> SEQ ID NO 262
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 262
tcgtcggcag cgtcagatgt gtataagaga caghhhhhnn ncttttgaa ggagctccag     60 atgaaag                                                              67

<210> SEQ ID NO 263
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 263
tcgtcggcag cgtcagatgt gtataagaga caghhhhhnn nntgctcatc ctccaggtgc    60
ggga                                                                 64

<210> SEQ ID NO 264
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 264
tcgtcggcag cgtcagatgt gtataagaga caghhhhhnn nngaagaaac catctgccct    60
tgtga                                                              65

<210> SEQ ID NO 265
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 265
tcgtcggcag cgtcagatgt gtataagaga caghhhhhnn nncctgcccc gggtttccct    60
gagcgac                                                            67

<210> SEQ ID NO 266
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 266
tcgtcggcag cgtcagatgt gtataagaga caghhhhhnn nntctctgcg cattgcagac    60
accca                                                              65

<210> SEQ ID NO 267
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 267
tcgtcggcag cgtcagatgt gtataagaga caghhhhhnn nnttgtttca tatcacagcc    60
tccca                                                              65

<210> SEQ ID NO 268
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 268
tcgtcggcag cgtcagatgt gtataagaga caghhhhhnn nngcttgtac attacagccg    60
tgca                                                               64

<210> SEQ ID NO 269

```
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 269
tcgtcggcag cgtcagatgt gtataagaga caghhhhhnn nnatctgagg aaaccctctg      60
tgca                                                                  64

<210> SEQ ID NO 270
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 270
tcgtcggcag cgtcagatgt gtataagaga caghhhhhnn nnacctgacg aaaccctcag      60
cccat                                                                 65

<210> SEQ ID NO 271
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 271
tcgtcggcag cgtcagatgt gtataagaga caghhhhhnn nncctatgcc tgtctttact      60
ttaatc                                                                66

<210> SEQ ID NO 272
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 272
tcgtcggcag cgtcagatgt gtataagaga caghhhhhnn nncttgagga aaccctcagt      60
ccatat                                                                66

<210> SEQ ID NO 273
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
```

<222> LOCATION: (39)..(42)
<223> OTHER INFORMATION: n is a, c, g, or t

<400> SEQUENCE: 273
tcgtcggcag cgtcagatgt gtataagaga caghhhhhnn nngaaaccat caacccatgt    60
gagtga    66

<210> SEQ ID NO 274
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 274
tcgtcggcag cgtcagatgt gtataagaga caghhhhhnn nnacttggag aaagactcag    60
ttcaa    65

<210> SEQ ID NO 275
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 275
tcgtcggcag cgtcagatgt gtataagaga caghhhhhnn nnacttggag aaaggctcag    60
ttcaa    65

<210> SEQ ID NO 276
<211> LENGTH: 62
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 276
tcgtcggcag cgtcagatgt gtataagaga caghhhhhnn nnctgcacat cacagcctcc    60
ca    62

<210> SEQ ID NO 277
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 277
tcgtcggcag cgtcagatgt gtataagaga caghhhhhnn nngtttggaa tatcgcagcc    60

-continued tctcat                                                             66

<210> SEQ ID NO 278
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 278
tcgtcggcag cgtcagatgt gtataagaga caghhhhhnn nnccctgctc atcagagact    60
ccaag                                                              65

<210> SEQ ID NO 279
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 279
tcgtcggcag cgtcagatgt gtataagaga caghhhhhnn nnctctgctc atcagagact    60
cccag                                                              65

<210> SEQ ID NO 280
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 280
tcgtcggcag cgtcagatgt gtataagaga caghhhhhnn nnccttgttc atcagagact    60
cacag                                                              65

<210> SEQ ID NO 281
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 281
tcgtcggcag cgtcagatgt gtataagaga caghhhhhnn nntccctgca catcacagag    60
acccaa                                                             66

<210> SEQ ID NO 282
<211> LENGTH: 66
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 282
tcgtcggcag cgtcagatgt gtataagaga caghhhhhnn nntctctgca aattgcagct    60
actcaa                                                               66

<210> SEQ ID NO 283
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 283
tcgtcggcag cgtcagatgt gtataagaga caghhhhhnn nnttgtcatc tccgcttcac    60
aactgg                                                               66

<210> SEQ ID NO 284
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 284
tcgtcggcag cgtcagatgt gtataagaga caghhhhhnn nngttttgaa tatgctggtc    60
tctcat                                                               66

<210> SEQ ID NO 285
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 285
tcgtcggcag cgtcagatgt gtataagaga caghhhhhnn nncctgaaga aaccatttgc    60
tcaaga                                                               66

<210> SEQ ID NO 286
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t
```

<400> SEQUENCE: 286
tcgtcggcag cgtcagatgt gtataagaga caghhhhhnn nntccttgtt gatcacggct    60
tcccgg    66

<210> SEQ ID NO 287
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 287
tcgtcggcag cgtcagatgt gtataagaga caghhhhhnn nnacctggag aagccctcgg    60
tgca    64

<210> SEQ ID NO 288
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 288
tcgtcggcag cgtcagatgt gtataagaga caghhhhhnn nncaccatca cagcctcaca    60
agtcgt    66

<210> SEQ ID NO 289
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 289
tcgtcggcag cgtcagatgt gtataagaga caghhhhhnn nntttctgca catcacagcc    60
ccta    64

<210> SEQ ID NO 290
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 290
tcgtcggcag cgtcagatgt gtataagaga caghhhhhnn nnctttatac attgcagctt    60
ctcagcc    67

```
<210> SEQ ID NO 291
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 291
tcgtcggcag cgtcagatgt gtataagaga caghhhhhnn nngtacattt cctcttccca    60
gaccac                                                                66

<210> SEQ ID NO 292
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 292
tcgtcggcag cgtcagatgt gtataagaga caghhhhhnn nncattgcat atcatggatt    60
cccagc                                                                66

<210> SEQ ID NO 293
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 293
tcgtcggcag cgtcagatgt gtataagaga caghhhhhnn nngctatttg tacatcaaag    60
gatccc                                                                66

<210> SEQ ID NO 294
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 294
tcgtcggcag cgtcagatgt gtataagaga caghhhhhnn nncagctccc tgcacatcac    60
agcca                                                                 65

<210> SEQ ID NO 295
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
```

<221> NAME/KEY: misc_feature
<222> LOCATION: (39)..(42)
<223> OTHER INFORMATION: n is a, c, g, or t

<400> SEQUENCE: 295
tcgtcggcag cgtcagatgt gtataagaga caghhhhhnn nnttgatcct gccccacgct    60
acgctga    67

<210> SEQ ID NO 296
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 296
tcgtcggcag cgtcagatgt gtataagaga caghhhhhnn nnttgatcct gcaccgtgct    60
accttga    67

<210> SEQ ID NO 297
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 297
tcgtcggcag cgtcagatgt gtataagaga caghhhhhnn nngttctctc cacatcactg    60
cagcc    65

<210> SEQ ID NO 298
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 298
tcgtcggcag cgtcagatgt gtataagaga caghhhhhnn nngccaccta tacatcagat    60
tccca    65

<210> SEQ ID NO 299
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 299
tcgtcggcag cgtcagatgt gtataagaga caghhhhhnn nntctctgca cattgtgccc    60
tccca                                                              65

<210> SEQ ID NO 300
<211> LENGTH: 67
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 300
tcgtcggcag cgtcagatgt gtataagaga caghhhhhnn nnccctgtac cttacggcct     60
cccagct                                                              67

<210> SEQ ID NO 301
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 301
tcgtcggcag cgtcagatgt gtataagaga caghhhhhnn nncttatcat atcatcatca     60
cagcca                                                               66

<210> SEQ ID NO 302
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 302
tcgtcggcag cgtcagatgt gtataagaga caghhhhhnn nntccctgca tattacagcc     60
acccaa                                                               66

<210> SEQ ID NO 303
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 303
tcgtcggcag cgtcagatgt gtataagaga caghhhhhnn nnacctcacc atcaattcct     60
taaaac                                                               66

<210> SEQ ID NO 304
<211> LENGTH: 66
<212> TYPE: DNA

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 304
tcgtcggcag cgtcagatgt gtataagaga caghhhhhnn nntccctgca tatcacagcc      60
tcccag                                                                 66

<210> SEQ ID NO 305
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 305
tcgtcggcag cgtcagatgt gtataagaga caghhhhhnn nncttcctga atatctcagc      60
atccat                                                                 66

<210> SEQ ID NO 306
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 306
tcgtcggcag cgtcagatgt gtataagaga caghhhhhnn nntcctgaac atcacagcca      60
cccag                                                                  65

<210> SEQ ID NO 307
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 307
tcgtcggcag cgtcagatgt gtataagaga caghhhhhnn nntccctgca catacaggat      60
tcccag                                                                 66

<210> SEQ ID NO 308
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t
```

<400> SEQUENCE: 308
tcgtcggcag cgtcagatgt gtataagaga caghhhhhnn nncaagatct cagactcaca    60
gctgg    65

<210> SEQ ID NO 309
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 309
tcgtcggcag cgtcagatgt gtataagaga caghhhhhnn nnccgtctca gcaccctcca    60
catca    65

<210> SEQ ID NO 310
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 310
tcgtcggcag cgtcagatgt gtataagaga caghhhhhnn nnccattgtg aaatattcag    60
tccagg    66

<210> SEQ ID NO 311
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 311
tcgtcggcag cgtcagatgt gtataagaga caghhhhhnn nngtggtcgc actgcagcaa    60
gaaga    65

<210> SEQ ID NO 312
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 312
tcgtcggcag cgtcagatgt gtataagaga caghhhhhnn nngatccggt ccacaaagct    60
ggagga    66

<210> SEQ ID NO 313
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 313
tcgtcggcag cgtcagatgt gtataagaga caghhhhhnn nncatcaatt ccctggagct    60
tggtga    66

<210> SEQ ID NO 314
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 314
tcgtcggcag cgtcagatgt gtataagaga caghhhhhnn nnttcaccta cacgccctgc    60
agccag    66

<210> SEQ ID NO 315
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 315
tcgtcggcag cgtcagatgt gtataagaga caghhhhhnn nnttcaccta cacaccctgc    60
agccag    66

<210> SEQ ID NO 316
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 316
tcgtcggcag cgtcagatgt gtataagaga caghhhhhnn nngaatgtga gcaccttgga    60
gctgg    65

<210> SEQ ID NO 317
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 317
tcgtcggcag cgtcagatgt gtataagaga caghhhhhnn nntactgagt caaacacgga    60
gctagg    66

<210> SEQ ID NO 318
<211> LENGTH: 66
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 318
tcgtcggcag cgtcagatgt gtataagaga caghhhhhnn nngctctgag atgaatgtga    60
gtgcct    66

<210> SEQ ID NO 319
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 319
tcgtcggcag cgtcagatgt gtataagaga caghhhhhnn nnctgagctg aatgtgaacg    60
cctt    64

<210> SEQ ID NO 320
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 320
tcgtcggcag cgtcagatgt gtataagaga caghhhhhnn nngagttctc gctcaggctg    60
gagt    64

<210> SEQ ID NO 321
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 321
tcgtcggcag cgtcagatgt gtataagaga caghhhhhnn nnctggggtt ggagtcggct    60
gctc    64

<210> SEQ ID NO 322
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 322
tcgtcggcag cgtcagatgt gtataagaga caghhhhhnn nnccctcac gttggcgtct    60 gctg    64

<210> SEQ ID NO 323
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 323
tcgtcggcag cgtcagatgt gtataagaga caghhhhhnn nntcccgctc aggctgctgt    60
cggc    64

<210> SEQ ID NO 324
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 324
tcgtcggcag cgtcagatgt gtataagaga caghhhhhnn nngatttccc gctcaggctg    60
gagt    64

<210> SEQ ID NO 325
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 325
tcgtcggcag cgtcagatgt gtataagaga caghhhhhnn nntcccctc aagctggagt    60 cagct    65

<210> SEQ ID NO 326
<211> LENGTH: 64

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 326
tcgtcggcag cgtcagatgt gtataagaga caghhhhhnn nntcccactc aggctggtgt    60
cggc                                                                64

<210> SEQ ID NO 327
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 327
tcgtcggcag cgtcagatgt gtataagaga caghhhhhnn nnctctgaag ttccagcgca    60
caca                                                                64

<210> SEQ ID NO 328
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 328
tcgtcggcag cgtcagatgt gtataagaga caghhhhhnn nngatccagc gcacacagca    60
ggag                                                                64

<210> SEQ ID NO 329
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 329
tcgtcggcag cgtcagatgt gtataagaga caghhhhhnn nnactctgaa gatccagcgc    60
acaga                                                               65

<210> SEQ ID NO 330
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
```

<223> OTHER INFORMATION: n is a, c, g, or t

<400> SEQUENCE: 330
tcgtcggcag cgtcagatgt gtataagaga caghhhhhnn nnagatccag cgcacagagc    60
aagg    64

<210> SEQ ID NO 331
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 331
tcgtcggcag cgtcagatgt gtataagaga caghhhhhnn nncagcgcac agagcagcgg    60
gact    64

<210> SEQ ID NO 332
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 332
tcgtcggcag cgtcagatgt gtataagaga caghhhhhnn nngagatcca gcgcacagag    60
cagg    64

<210> SEQ ID NO 333
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 333
tcgtcggcag cgtcagatgt gtataagaga caghhhhhnn nnccctcaac cctggagtct    60
acta    64

<210> SEQ ID NO 334
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 334
tcgtcggcag cgtcagatgt gtataagaga caghhhhhnn nntccccaat cctggcatcc    60
acca    64

<210> SEQ ID NO 335
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 335
tcgtcggcag cgtcagatgt gtataagaga caghhhhhnn nnctaaacct gagctctctg    60
gagct                                                               65

<210> SEQ ID NO 336
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 336
tcgtcggcag cgtcagatgt gtataagaga caghhhhhnn nncctcact ctggagtctg     60 ctgc                                                                64

<210> SEQ ID NO 337
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 337
tcgtcggcag cgtcagatgt gtataagaga caghhhhhnn nncctcact ctggagtcag     60 ctac                                                                64

<210> SEQ ID NO 338
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 338
tcgtcggcag cgtcagatgt gtataagaga caghhhhhnn nntcctcact ctggagtccg    60
ctac                                                                64

<210> SEQ ID NO 339
<211> LENGTH: 65
<212> TYPE: DNA
<213> ORGANISM: Artificial Sequence
<220> FEATURE:

<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 339
tcgtcggcag cgtcagatgt gtataagaga caghhhhhnn nnccactctc aagatccagc    60
ctgca                                                                65

<210> SEQ ID NO 340
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 340
tcgtcggcag cgtcagatgt gtataagaga caghhhhhnn nngaggatcc agcccatgga    60
accca                                                                65

<210> SEQ ID NO 341
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 341
tcgtcggcag cgtcagatgt gtataagaga caghhhhhnn nnctgaagat ccagcctgca    60
gagc                                                                 64

<210> SEQ ID NO 342
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 342
tcgtcggcag cgtcagatgt gtataagaga caghhhhhnn nncagccctc agaacccagg    60
gact                                                                 64

<210> SEQ ID NO 343
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 343
tcgtcggcag cgtcagatgt gtataagaga caghhhhhnn nngagctcct tggagctggg    60
ggact                                                               65

<210> SEQ ID NO 344
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 344
tcgtcggcag cgtcagatgt gtataagaga caghhhhhnn nngtgcagc ctgcagaact     60 ggag                                                                64

<210> SEQ ID NO 345
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 345
tcgtcggcag cgtcagatgt gtataagaga caghhhhhnn nngacatccg ctcaccaggc    60
ctgg                                                                64

<210> SEQ ID NO 346
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 346
tcgtcggcag cgtcagatgt gtataagaga caghhhhhnn nntgagatcc aggctacgaa    60
gctt                                                                64

<210> SEQ ID NO 347
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 347
tcgtcggcag cgtcagatgt gtataagaga caghhhhhnn nngaagatcc atcccgcaga    60
gccg                                                                64

<210> SEQ ID NO 348

<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 348
tcgtcggcag cgtcagatgt gtataagaga caghhhhhnn nnggatccag caggtagtgc    60
gagg    64

<210> SEQ ID NO 349
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 349
tcgtcggcag cgtcagatgt gtataagaga caghhhhhnn nncactgtga catcggccca    60
aaag    64

<210> SEQ ID NO 350
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 350
tcgtcggcag cgtcagatgt gtataagaga caghhhhhnn nnctgacagt gaccagtgcc    60
catc    64

<210> SEQ ID NO 351
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 351
tcgtcggcag cgtcagatgt gtataagaga caghhhhhnn nngagatcca gtccacggag    60
tcag    64

<210> SEQ ID NO 352
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 352
tcgtcggcag cgtcagatgt gtataagaga caghhhhhnn nngtgaagtt ggcccacacc    60
agcca    65

<210> SEQ ID NO 353
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 353
tcgtcggcag cgtcagatgt gtataagaga caghhhhhnn nncctggcaa tcctgtcctc    60
agaa    64

<210> SEQ ID NO 354
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 354
tcgtcggcag cgtcagatgt gtataagaga caghhhhhnn nngagtctgc catcccaac    60 caga    64

<210> SEQ ID NO 355
<211> LENGTH: 63
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 355
tcgtcggcag cgtcagatgt gtataagaga caghhhhhnn nnggagtctg ccaggccctc    60
aca    63

<210> SEQ ID NO 356
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 356
tcgtcggcag cgtcagatgt gtataagaga caghhhhhnn nngaagtctg ccagcaccaa    60

```
                                                                       -continued ccag                                                              64

<210> SEQ ID NO 357
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 357
tcgtcggcag cgtcagatgt gtataagaga caghhhhhnn nnggagtcgc ccagccccaa       60
ccag                                                              64

<210> SEQ ID NO 358
<211> LENGTH: 64
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 358
tcgtcggcag cgtcagatgt gtataagaga caghhhhhnn nnggagtccg ccagcaccaa       60
ccag                                                              64

<210> SEQ ID NO 359
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 359
tcgtcggcag cgtcagatgt gtataagaga caghhhhhnn nngtgagcaa catgagccct       60
gaaga                                                             65

<210> SEQ ID NO 360
<211> LENGTH: 65
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(42)
<223> OTHER INFORMATION: n is a, c, g, or t

<400> SEQUENCE: 360
tcgtcggcag cgtcagatgt gtataagaga caghhhhhnn nnagttcta agaagctcct        60 tctca                                                             65
```